(12) United States Patent
Kim et al.

(10) Patent No.: US 11,464,344 B2
(45) Date of Patent: Oct. 11, 2022

(54) BED

(71) Applicant: LG ELECTRONICS INC., Seoul (KR)

(72) Inventors: Daewoong Kim, Seoul (KR); Minkyu Oh, Seoul (KR); Deukwon Lee, Seoul (KR); Yongnam Kim, Seoul (KR); Seongwoo An, Seoul (KR); Yanghwan No, Seoul (KR); Bodeung Hwang, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 49 days.

(21) Appl. No.: 17/090,062

(22) Filed: Nov. 5, 2020

(65) Prior Publication Data

US 2021/0307525 A1 Oct. 7, 2021

(30) Foreign Application Priority Data

| Apr. 7, 2020 | (KR) | ................ | KR10-2020-0042008 |
| Apr. 7, 2020 | (KR) | ................ | KR10-2020-0042009 |
| Apr. 7, 2020 | (KR) | ................ | KR10-2020-0042010 |
| Apr. 7, 2020 | (KR) | ................ | KR10-2020-0042012 |
| Apr. 7, 2020 | (KR) | ................ | KR10-2020-0042015 |
| Apr. 7, 2020 | (KR) | ................ | KR10-2020-0042018 |
| Apr. 7, 2020 | (KR) | ................ | KR10-2020-0042019 |
| Apr. 7, 2020 | (KR) | ................ | KR10-2020-0042020 |
| Apr. 7, 2020 | (KR) | ................ | KR10-2020-0042021 |

(51) Int. Cl.
*A47C 21/04* (2006.01)
*A47C 20/04* (2006.01)
(Continued)

(52) U.S. Cl.
CPC .......... *A47C 21/044* (2013.01); *A47C 20/041* (2013.01); *A47C 23/002* (2013.01); *A47C 23/34* (2013.01); *A47C 27/053* (2013.01); *A47C 27/064* (2013.01); *A47C 27/065* (2013.01); *A47C 31/008* (2013.01); *A47C 31/12* (2013.01); *D06F 60/00* (2013.01); *A47C 21/048* (2013.01); *A47C 23/043* (2013.01); *A47C 27/05* (2013.01); *A47C 27/10* (2013.01); *A47C 27/14* (2013.01);
(Continued)

(58) Field of Classification Search
CPC ..... A47C 21/044; A47C 21/048; A47C 27/10; F24F 8/108; A61G 7/018
See application file for complete search history.

(56) References Cited

U.S. PATENT DOCUMENTS

| 7,908,693 B2 | 3/2011 | DeMoss |
| 8,256,043 B2 | 9/2012 | Fromme-Ruthmann |

(Continued)

*Primary Examiner* — Peter M. Cuomo
*Assistant Examiner* — George Sun
(74) *Attorney, Agent, or Firm* — KED & Associates LLP

(57) ABSTRACT

A bed includes a mattress set on which a user's body is placed, an adjustable bedframe to adjust a position or orientation of the mattress set for various sitting and sleeping positions, and a dryer to dry the mattress set. The dryer includes a fan, a filter, and a heater to discharge filtered hot air toward the dryer to reduce mildew and mites. A humidity sensing sheet may be provided to sense a humidity level at different regions or areas of the bed, and the dryer may be controlled to supply hot air to regions of the bed having a higher humidity level than a predetermined humidity level or humidity range.

20 Claims, 45 Drawing Sheets

(51) Int. Cl.
*A47C 27/06* (2006.01)
*A47C 23/00* (2006.01)
*D06F 60/00* (2009.01)
*A47C 31/00* (2006.01)
*A47C 23/34* (2006.01)
*A47C 27/05* (2006.01)
*A47C 31/12* (2006.01)
*A61G 7/018* (2006.01)
*F24F 8/108* (2021.01)
*A47C 27/10* (2006.01)
*A47C 27/14* (2006.01)
*A47C 23/043* (2006.01)

(52) U.S. Cl.
CPC ..... *A47C 31/123* (2013.01); *A61B 2562/0247* (2013.01); *A61G 7/018* (2013.01); *A61G 2203/12* (2013.01); *A61G 2203/34* (2013.01); *F24F 8/108* (2021.01)

(56) References Cited

U.S. PATENT DOCUMENTS

| | | | | |
|---|---|---|---|---|
| 8,402,579 | B2* | 3/2013 | Marquette | A47C 7/74 5/652.2 |
| 9,119,478 | B2 | 9/2015 | DeFranks et al. | |
| 2003/0140418 | A1* | 7/2003 | Klamm | A47C 21/048 5/423 |
| 2009/0000031 | A1* | 1/2009 | Feher | A47C 7/74 5/423 |
| 2014/0201909 | A1* | 7/2014 | Weyl | A61G 7/05784 5/423 |
| 2015/0208814 | A1* | 7/2015 | Alletto, Jr. | A61G 7/05784 5/423 |
| 2015/0272338 | A1* | 10/2015 | Greener | A47C 31/00 5/423 |
| 2016/0128487 | A1* | 5/2016 | Eskridge, III | A47C 7/744 5/423 |
| 2017/0325595 | A1* | 11/2017 | DeFranks | A47C 21/048 |
| 2017/0360212 | A1* | 12/2017 | Rawls-Meehan | A47C 27/14 |
| 2018/0027981 | A1* | 2/2018 | Sherman | A47C 21/044 |
| 2018/0242753 | A1* | 8/2018 | Ghanei | A47C 21/044 |
| 2018/0271300 | A1* | 9/2018 | Wang | A47C 27/121 |
| 2019/0320808 | A1* | 10/2019 | Chapin | A47C 21/044 |
| 2020/0000241 | A1* | 1/2020 | Jansen | A47C 17/04 |
| 2020/0214459 | A1* | 7/2020 | Venditto | A47C 19/22 |

* cited by examiner

FIG. 13
FIG. 14
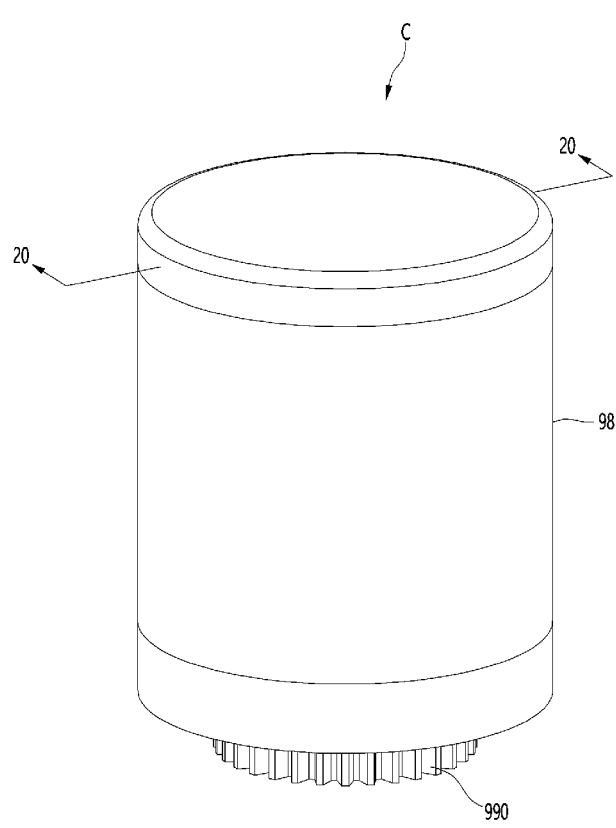
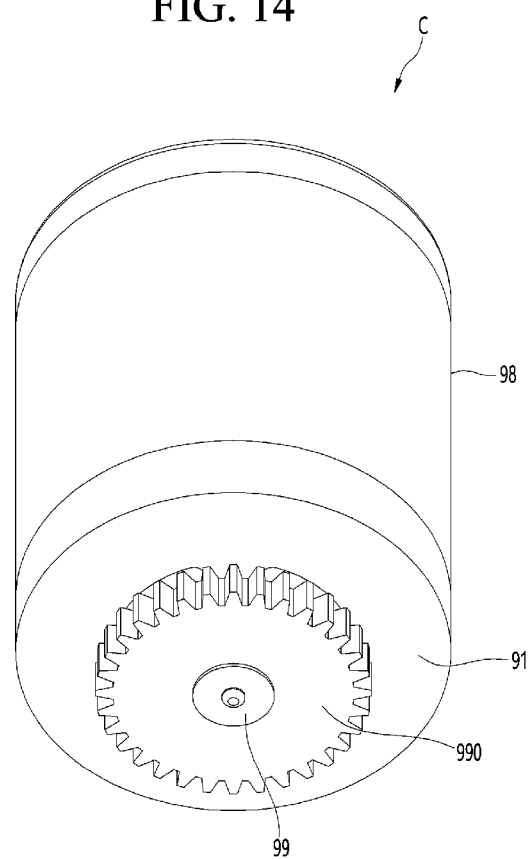

C

98

97

96

95

94

92

93

91

99
990

FIG. 16
FIG. 17
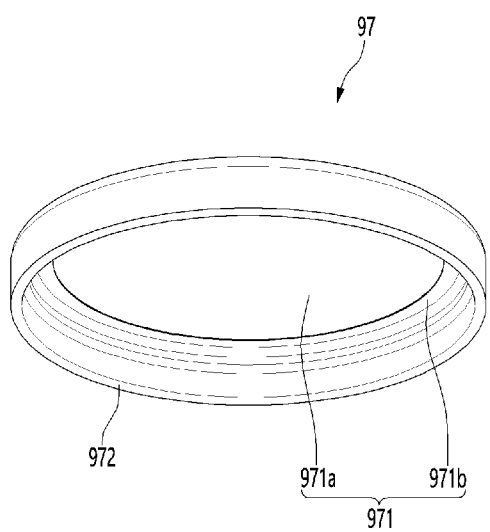
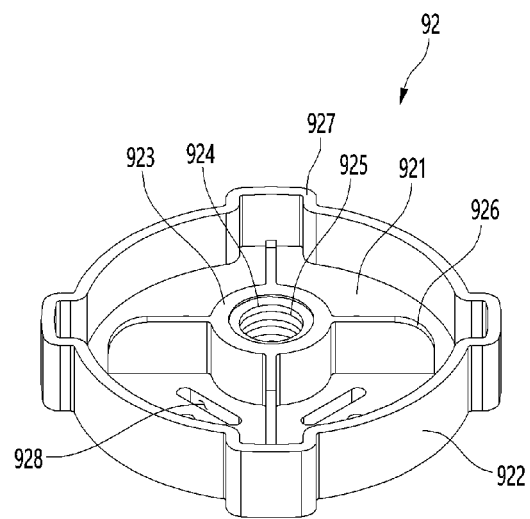
FIG. 18
FIG. 19
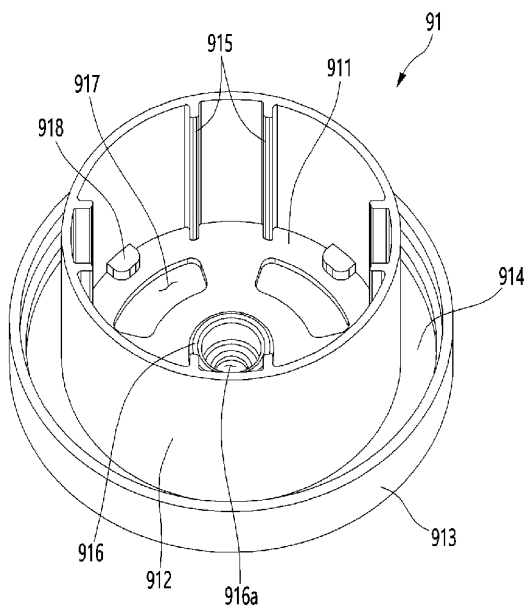
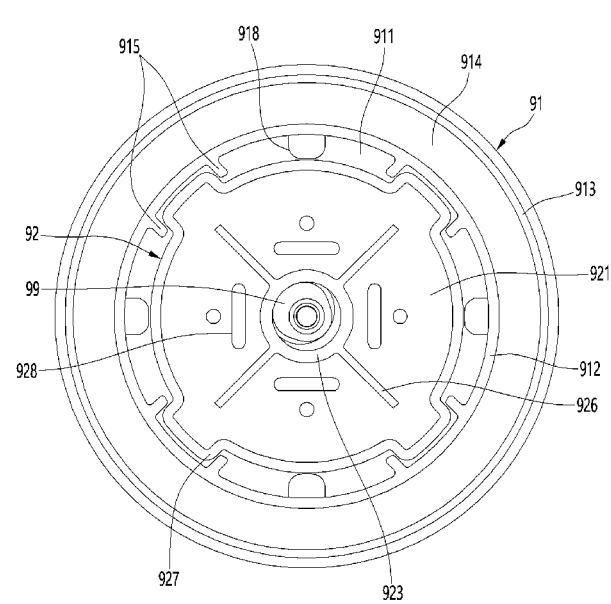

FIG. 70
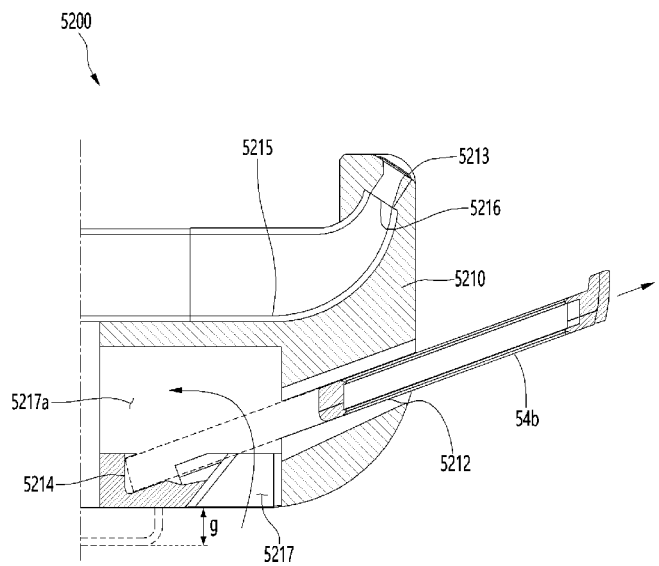
FIG. 71
FIG. 72
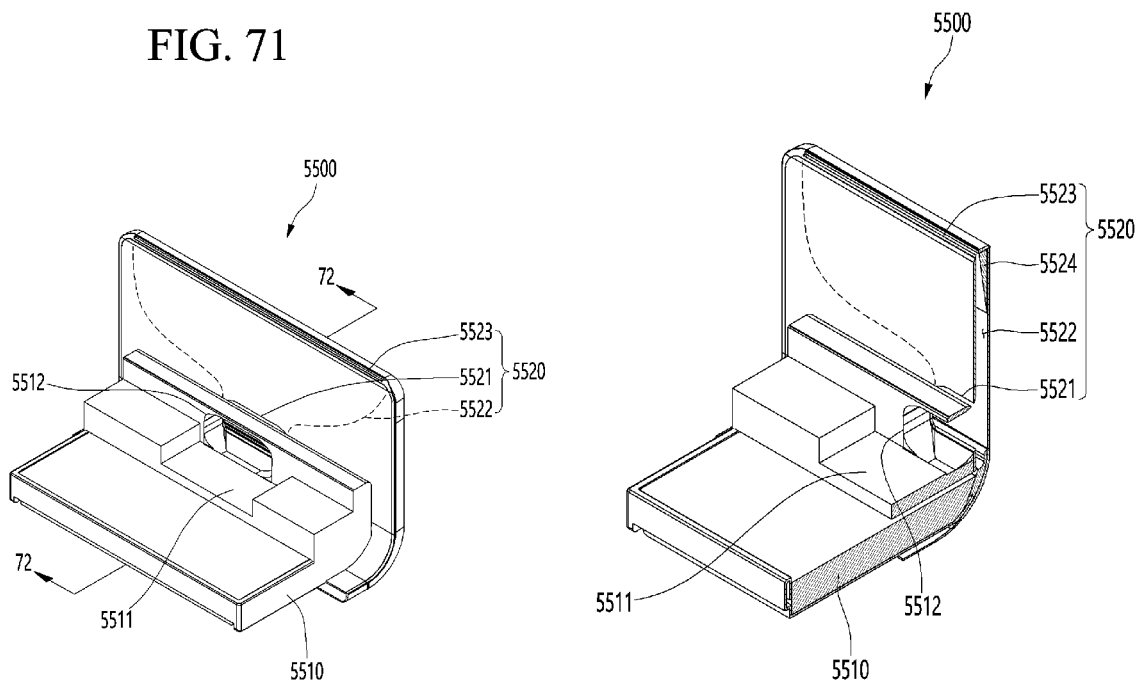

BED

CROSS-REFERENCE TO RELATED APPLICATIONS

This application claims priority under 35 U.S.C. § 119 to Korean Application 10-2020-0042008, 10-2020-0042009, 10-2020-0042010, 10-2020-0042012, 10-2020-0042015, 10-2020-0042018, 10-2020-0042019, 10-2020-0042020, and 10-2020-0042021, all filed on Apr. 7, 2020, whose entire disclosures are hereby incorporated by reference.

TECHNICAL FIELD

The present invention relates to a bed.

TECHNICAL BACKGROUND OF THE INVENTION

Mattresses provide cushioning for a bed and may be a spring mattress, a sponge mattress, a memory foam mattress, or include some other elastic material. Traditionally, most modern mattresses are spring mattresses, though memory foam mattresses or toppers are increasing in popularity. Mattresses may also use a combination of elastic materials, such as a hybrid coil spring and memory foam mattress.

In a spring mattress, coil springs may be complicatedly entangled to form a single cushion member. However, complicated coil spring mattresses have a disadvantage in that vibrations from an elastic force of one spring are easily transmitted to another spring such that, when one person lies down on a side of the mattress, vibration or movement may be felt by another person sitting or lying on another side of the mattress, causing discomfort. Some coil spring mattresses may have a plurality of spring modules arranged in a pocket to reduce an amount of vibrations or movement propagating from one side of the mattress to another.

However, such a spring mattresses, including the pocket type mattress, is not readily adjustable in firmness or cushion strength. A desired firmness of the mattress may vary according to a user's gender, age, and physical condition. When two or more users use the same mattress, the users may have to compromise on a firmness, as different sides or portions of the conventional spring mattress cannot be easily adjusted or customized.

Various studies and efforts have been made to implement a bed in which firmness may be set differently according to a position of where the user lies down or based on a point or portion where a user's body touches the mattress.

U.S. Pat. No. 7,908,693 (granted Mar. 22, 2011) discloses a coil-in-coil spring for a mattress. The coil-in-coil spring has an inner spring having a weaker elastic strength and an outer spring having a larger elastic strength. The outer spring is longer than the inner spring, and the inner and outer springs are provided in a pocket. Since the length and elastic strength of the inner spring and the outer spring are set differently, the firmness differs depending on the magnitude of the load acting on the upper surface of the coil-in-coil. Accordingly, when the user lies on the mattress, the amount of contraction or compression of the spring varies for each body part where the load acts differently. However, the firmness is the same or similar for every user at a certain weight. The user may not adjust the firmness of the mattress according to his particular desire; rather his weight is what determines the firmness.

U.S. Pat. No. 9,119,478 (granted Sep. 1, 2015) discloses a plunger matrix mattress having a plurality of dual-spring plungers, which have inner and outer tension springs. The firmness of the mattress may be freely set at different predetermined "zones" or positions according to the user's selection. However, from the contents disclosed in FIGS. 3A to 6 of U.S. Pat. No. 9,119,478, a number of zones is limited, and a variable range of the elastic strength is narrow. In addition, since the firmness is adjusted by hand, the firmness at multiple positions or zones cannot be simultaneously adjusted.

U.S. Pat. No. 8,256,043 (granted Sep. 4, 2012) discloses a base plate and a support plate rotatably coupled to the base plate. An elastic strength of a support element is adjusted by a rotation of the support plate. A firmness may be set within a range by a user in rotating, by hand, the support plate.

In the case of the disclosed coil-in-coil mattress, plunger matrix mattress, and base plate and support plate mattress, sweat or other bodily fluids may permeate a surface of the mattress that the skin touches, and in summer, when the humidity is high, not only the mattress but also the sheets may be moist or wet, causing discomfort. If the mattress is kept moist or wet for a long time, the mattress is very likely to be contaminated with mold or mites.

U.S. Pat. No. 8,402,579 (granted Mar. 26, 2013) discloses a climate controlled bed having a thermoelectric device and air distribution device to supply hot or cold air to the mattress. However, there is a disadvantage in that hot or cold air is not smoothly or evenly supplied to the mattress.

The above references are incorporated by reference herein where appropriate for appropriate teachings of additional or alternative details, features and/or technical background.

BRIEF DESCRIPTION OF THE DRAWINGS

The embodiments will be described in detail with reference to the following drawings in which like reference numerals refer to like elements wherein:

FIG. 13 is a front perspective view of a cushion according to an embodiment;

FIG. 14 is a bottom perspective view of the cushion;

FIG. 16 is a bottom perspective view of an upper cover constituting a cushion according to an embodiment;

FIG. 17 is a perspective view of an inner case constituting a cushion according to an embodiment;

FIG. 18 is a perspective view of an outer case constituting a cushion according to an embodiment;

FIG. 19 is a plan view showing a coupled state of an outer case, an inner case, and a lead screw constituting a cushion according to an embodiment;

FIG. 70 is an enlarged cross-sectional view of portion A in FIG. 69;

FIG. 71 is a perspective view of an air dispenser constituting a drying module according to an embodiment;

FIG. 72 is a cut-away perspective view of the air dispenser cut along 72-72 of FIG. 71;

DETAILED DESCRIPTION OF THE INVENTION

Figure 1:
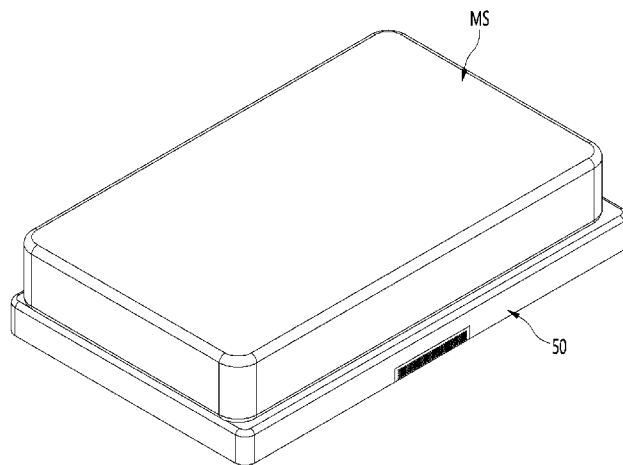
FIG. 1 is a perspective view of a bed according to an embodiment.
Figure 2:
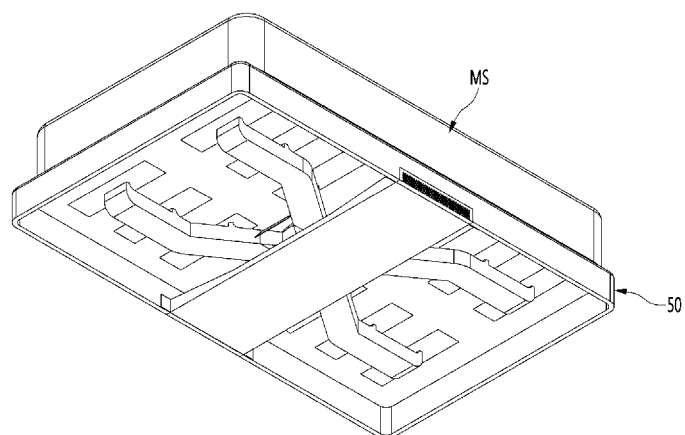
FIG. 2 is a bottom perspective view of the bed according to an embodiment.

Referring to FIGS. 1 and 2, a bed 10 according to an embodiment may include a mattress set MS and a drying module or dryer 50 on which the mattress set MS is placed. The drying module 50 may be configured to blow air, which may be optionally heated, to the mattress set MS to dry the mattress set MS. The mattress set MS may be lifted and separated from the drying module 50, and at least a part of the mattress set MS may be tilted or angled to be adjustable.

Figure 3:
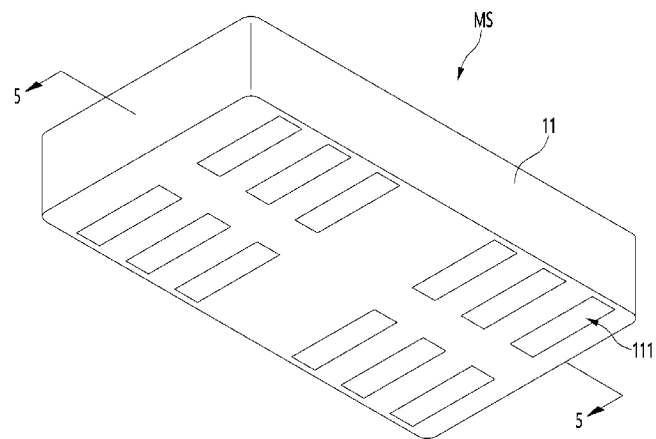
FIG. 3 is a bottom perspective view of a mattress set according to an embodiment.
Figure 4:
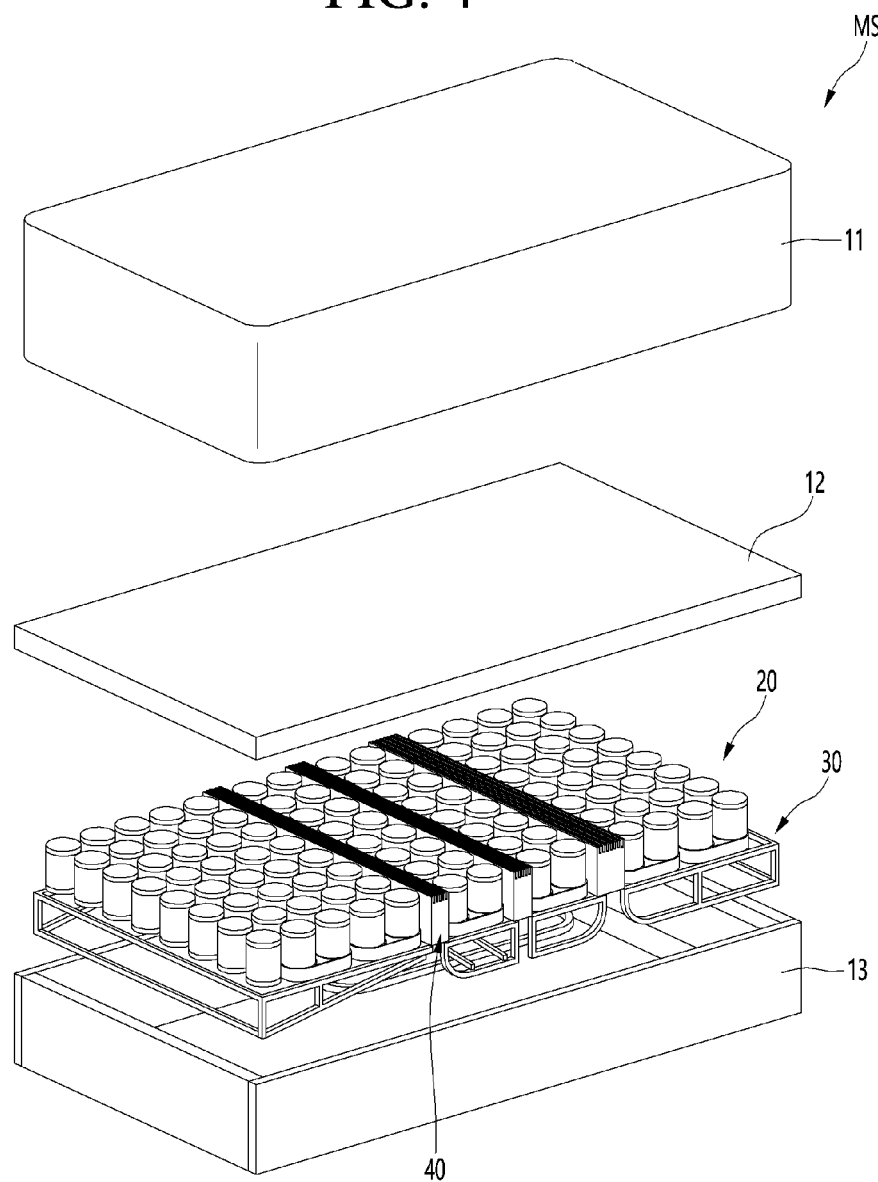
FIG. 4 is an exploded perspective view of the mattress set.
Figure 5:
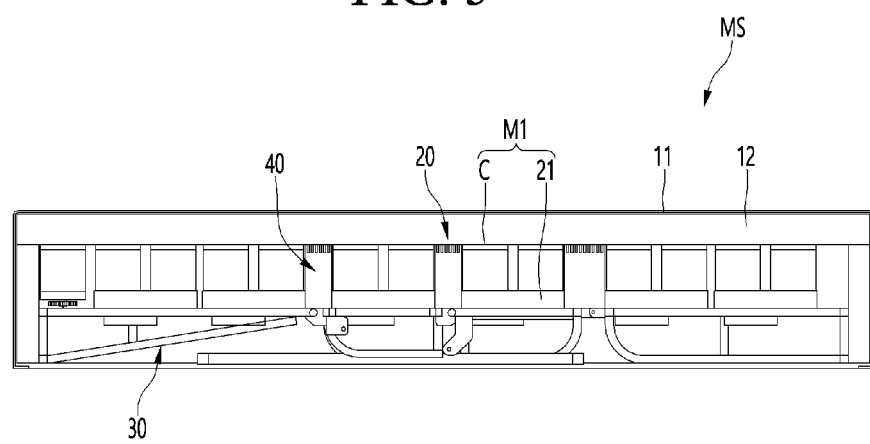
FIG. 5 is a longitudinal cross-sectional view of a mattress set cut along 4-4 of FIG. 3.

Referring to FIGS. 3 to 5, the mattress set MS may include at least one topper 12 (e.g., an elastic foam layer such as memory or latex foam or mattress) on which a user may lie and may further include a cushion module or firmness module 20 on which the topper 12 is provided. The cushion module 20 may have a plurality of cushions C arranged in separate sections or firmness adjusters M1. A firmness of the cushions C in a same firmness adjuster M1 may be the same or similar, and a user may adjust a firmness of a desired area on the bed 10 by controlling the firmness adjuster M1 corresponding to the desired area. When the user controls the firmness of a particular firmness adjuster M1, a firmness of all of the cushions C in the particular firmness adjuster M1 may be simultaneously adjusted.

The cushion module 20 may be provided on top of a bedframe 30, which may have an adjustable orientation or posture. The mattress set MS may further include a partition 40 provided between certain adjacent firmness adjusters M1 where an orientation of the bedframe 30 may be adjusted.

A safe guard 13 may surround an edge of the bedframe 30. The mattress set MS may further include a bed cover or cover sheet 11 (e.g., a fitted sheet or mattress protector) surrounding at least the topper 12 and optionally the safe guard 13, as shown. The cushion module 20 and topper 12 may collectively be referred to as a mattress, while the cushion module 20, topper 12, bedframe 30, and safe guard 13 may be bundled together by the bed cover 11 to be referred to as a mattress set MS. A size of the bed cover 11 may be large enough to completely surround the cushion module 20, topper 12, bedframe 30, and safe guard 13, including the bottom of the mattress set MS.

The bed cover 11 may completely surround a bottom surface of the bedframe 30, and a plurality of guide holes 111 may be formed on the bottom surface of the bed cover 11 so as to allow air blown by the dryer module 50 to pass through to the cushion module 20 and topper 12. Embodiments disclosed herein are not limited to an arrangement of the mattress set MS and/or bedframe 30. Other arrangements are described in co-pending U.S. application Ser. No. 17/089,910 filed on Nov. 5, 2020, the entire contents of which are incorporated by reference herein.

Hereinafter, "firmness," "strength", or "cushion strength" may be understood to mean a degree of softness or hardness of the bed 10. The firmness of the bed that a user prefers may vary depending on a user's age, physical condition, or simply taste or preference. For this reason, the bed 10 according to embodiments disclosed herein is characterized in that a user may adjust the firmness of the bed through manipulation of the cushion module 20.

The bed cover 11 may be made of or include a soft or elastic material (e.g., a fitted sheet) and may maintain a taut state when wrapped around the topper 12, cushion module 20, bedframe 30, and safe guard 13. When the bed 10 is inclined or bent according to an operation of the bedframe 30, the bed cover 11 may be stretched, and when the bedframe 30 returns to a flat or default state, the bed cover 11 may be contracted back to a previous state. The user's body may be placed on the bed cover 11 and/or the topper 12. The topper 12 may include a memory foam mattress or layer that is depressed by the user's weight and returns to an original state when the weight is removed.

The cushion module 20 may be an assembly or array of cushions C arranged in a grid form from a head of the bed 10 to a foot of the bed 10. The cushions C may extend vertically from a bottom of the bed 10 toward a top of the bed 10. The cushions C may have a cylindrical shape, but embodiments disclosed herein are not limited. A set of cushions C may be provided in a cushion case 21, and such a set, along with a drive device described later, may define the firmness adjuster M1. The firmness adjusters M1 may be arranged in an array or grid form and each firmness adjuster M1 may define an area or region of the bed 10 whose firmness may be independently adjusted.

As an optional alternative, there may be some cushions C not provided in a cushion case 21 and coupled to the bedframe 30 (e.g., at a head or foot of the bedframe 30). In such an embodiment, a tension of the cushions C may be independently adjustable by hand, or each individual cushion C may have its own drive or motor. Embodiments disclosed herein are not limited.

The partition 40 may be interposed between certain adjacent firmness adjusters M1 and placed at a hinge point of the bedframe 30. A distance between adjacent cushions C on opposite sides of the hinge point may be larger than a distance between adjacent cushions C elsewhere to minimize interference between cushions C at the hinge point during an operation of the bedframe 30. When a user's body part is placed at or near the hinge point, the partition 40 may provide support so that the user may feel more comfortable while lying down.

The safe guard 13 may prevent a user's leg or knee from colliding with the cushion module 20 or bedframe 30, which may cause pain or injury. The safe guard 13 may be formed of a soft or elastic material such as a sponge, latex foam, or memory foam.

Figure 6:
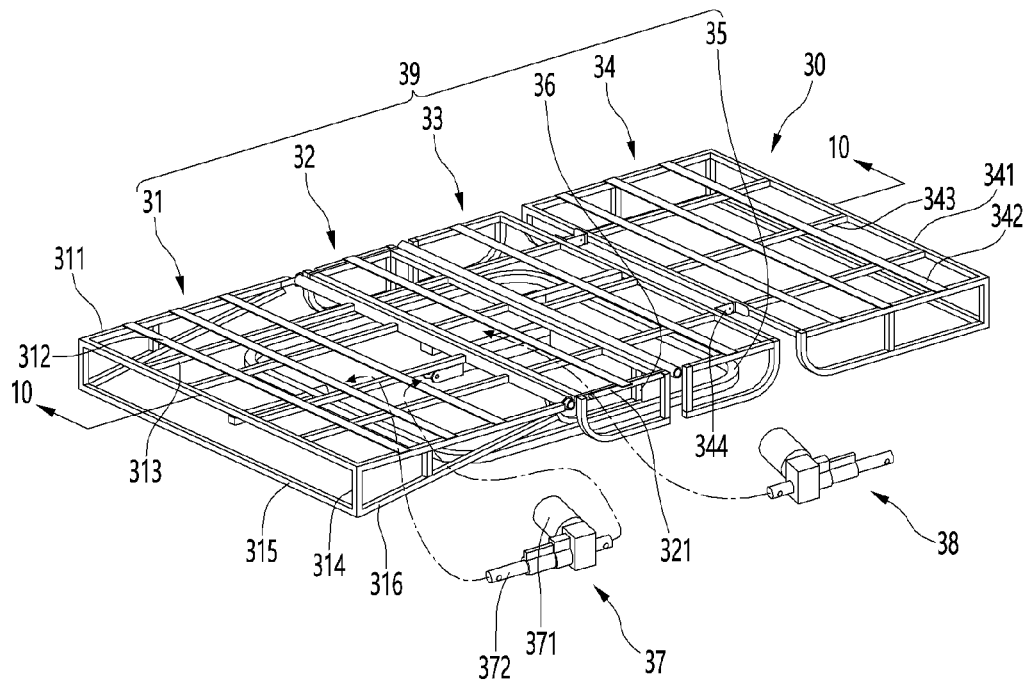
FIG. 6 is a perspective view from above of a bedframe constituting a mattress set.
Figure 7:
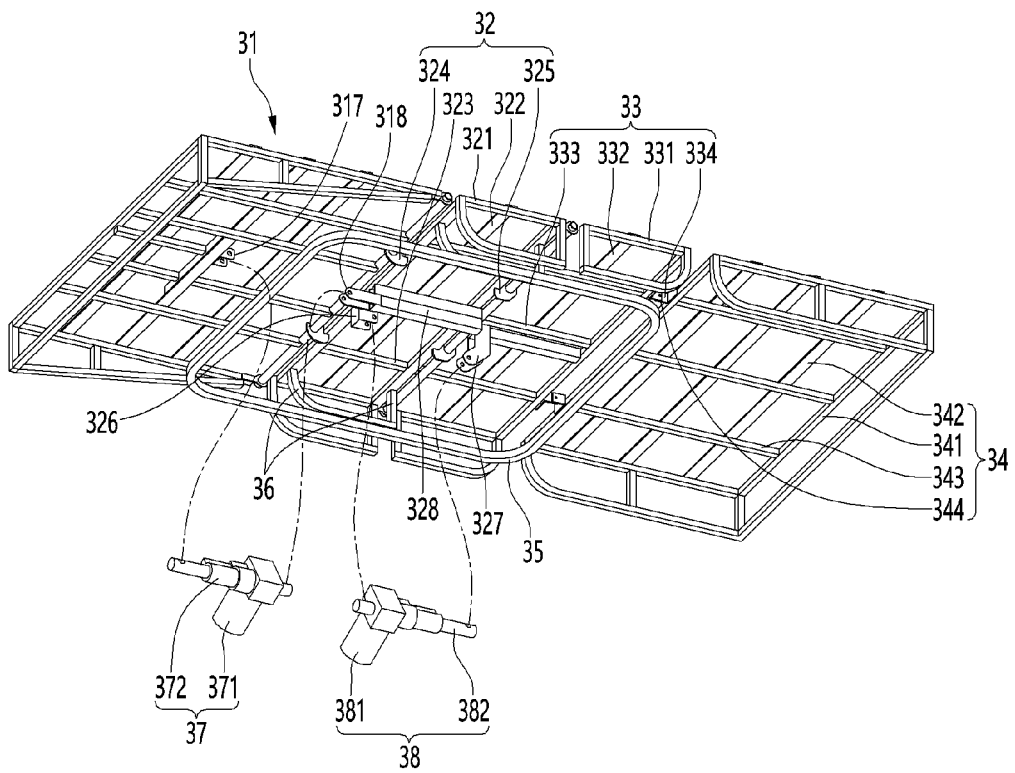
FIG. 7 is a perspective view of the bedframe as viewed from below.

Referring to FIGS. 6 and 7, the bedframe 30 may include a base or bottom frame 35 placed on an installation surface (e.g., a floor, box spring, platform, or larger bed frame), and a seating frame 39 on which the cushion module 20 is placed. Alternatively, the base frame 35 may be a plate. A support frame or connection bar 36 may connect the base frame 35 and the seating frame 39.

The seating frame 39 may include a plurality of frames or supports configured to move, pivot, and/or incline relative to each other. The plurality of frames may be hinged to each other, but embodiments disclosed herein are not limited. For example, the seating frame 39 may include an upper body or main frame 31 configured to support a user's upper body or torso, a hip or bottom frame 32 configured to support a user's hip area, a thigh or upper leg frame 33 configured to support a user's thigh or upper leg, and a calf or lower leg frame 34 configured to support a user's calf or lower leg.

The upper body, hip, thigh, and calf frames 31, 32, 33, and 34 may alternatively be referred to as upper body, hip, thigh, and calf supports. The upper body frame 31 may alternatively be referred to as a torso frame 31.

The seating frame 39 is not limited to upper body, hip, thigh, and calf frames 31, 32, 33, and 24. For example, there may be an optional headrest or neck and shoulder support configured to support a user's head, neck, and/or shoulders. Such an optional headrest may move, pivot, or incline with respect to the upper body frame 31. As another optional addition, there may be a lumber or lower torso support configured to support a user's lumbar and which may move, pivot, or incline relative to the upper body frame 31 and the hip frame 32.

A front or upper end of the upper body frame 31 (at a head of the bed 10) may be defined as a head of the bedframe 30, and a rear or lower end of the calf frame 34 (at a foot of the bed 10) may be defined as a foot of the bedframe 30. Here, a front-rear direction may be a direction extending between the head and foot of the bed 10. A rear end of the upper body frame 31 may be tiltably or rotatably connected (e.g., hinged) to a front end of the hip frame 32, and a front end of the thigh frame 33 may be tilted or rotatably connected (e.g., hinged) to a rear end of the hip frame 32. A rear end of the thigh frame 33 and a front end of the calf frame 34 may be connected to be relatively rotatable (e.g., via a shaft, pin, or hinge structure).

The upper body frame 31 may include an outer frame 311, a plurality of first plates or bars 312, and a plurality of second plates or bars 313. The first bars 312 may alternatively be referred to as left-right bars, upper bars, or cushion seating plates. The second bars 313 may alternatively be referred to as front-rear bars, lower bars, or connection bars.

The outer frame 311 may have a rectangular shape, a stadium shape, or a curved rectangular shape, and may define a front end (or head), a rear end, and both side ends (i.e., left and right ends corresponding to left and right sides of a lying human body) of the upper body frame 31. The plurality of second bars 313 may connect the front end and the rear end of the outer frame 311 and may be spaced apart from each other in the left-right direction of the outer frame 311. The plurality of first bars 312 may connect the left end and the right end of the outer frame 311 and may be spaced apart from each other in the front-rear direction of the outer frame 311. Accordingly, the plurality of second bars 313 and the plurality of first bars 312 may be arranged to be perpendicular to each other in a grid or lattice structure.

At the left and right corners of the front end of the outer frame 311, a pair of vertical bars 314 may extend in the vertical direction, and the pair of vertical bars 314 may be attached to the horizontal bar 315. An inclined bar 316 may extend from the lower end of each of the pair of vertical bars 314 to the rear end of the outer frame 311.

The pair of vertical bars 314 may transmit a vertical load applied to the outer frame 311 to the installation surface, thereby preventing the outer frame 311 from bending due to the vertical load. The vertical load may be a combined load or weight of a user's upper body, firmness modules M1 seated on the first bars 312, and a partial load of the topper 12.

The horizontal bar 315 may prevent the lower ends of the pair of vertical bars 314 from being bent in a direction away from each other or in a direction closer to each other due to the vertical load. The inclined bar 316 may prevent the pair of vertical bars 314 from bending forward or backward of the bedframe 30 due to the vertical load.

A frame portion or bar may function as a hinge axis or rotation center of the outer frame 311. A rotation center of the upper body frame 31 may be defined as an upper hinge axis. The upper hinge axis may be defined by a bar at a rear end of the outer frame 311 of the upper body frame 31.

An upper or front drive or actuator 37 may be mounted on a bottom surface of the outer frame 311 to rotate the upper body frame 31 around the upper hinge axis. The upper actuator 37 may include a drive 371 (e.g., a motor or linear actuator) and a plunger 372 that is extended or contracted by the drive 371. When the plunger 372 extends forward toward a front end of the upper body frame 31, the upper body frame 31 may rotate upward, and when the plunger 372 is retracted backward toward the rear end of the upper body frame 31, the upper body frame 31 may rotate downward.

A fastening flange may fix the upper actuator 37 to a bottom of the seating frame 39. The fastening flange may include a plunger fastening flange 317 to which a front end of the plunger 372 may be rotatably connected, and a driving fastening flange 318 to which a rear end of the drive 371 is rotatably connected.

The plunger fastening flange 317 may be formed on the bottom surface of the upper body frame 31, and the driving fastening flange 318 may be formed on the bottom surface of the hip frame 32. The plunger fastening flange 317 may be formed at a higher position than the driving fastening flange 318. A horizontal line (or horizontal plane) passing through the plunger fastening flange 317 and a horizontal line (or horizontal plane) passing through the driving fastening flange 318 may be spaced apart by a predetermined distance in the vertical direction.

The plunger 372 may be provided to be inclined while the seating frame 39 may extend horizontally. When the plunger 372 is extended, the upper body frame 31 may rotate upward so as to bend with respect to the hip frame 32. If the plunger 372 is retracted in a horizontal state, the upper body frame 31 may not rotate smoothly upward.

The hip frame 32, like the upper body frame 31, may include an outer frame 321, at least one first bar or cushion seating plates 322, and a plurality of second bars or connection bars 323. The outer frame 321 may have a rectangular shape by four bars. A plurality of upper hinge shaft brackets 324 may be spaced apart from each other in the left and right directions on a bottom surface of a front end of the outer frame 321 (FIG. 7). A rear end of the upper body frame 31 may be rotatably connected to the front end of the hip frame 32 via the plurality of upper hinge shaft brackets 324.

The hip frame 32 may further include a load support bar 328 connecting a bottom of the front end and a bottom of the rear end of the outer frame 321. The driving fastening flange 318 may be connected to the front end of the load support bar 328. When the upper body frame 31 is tilted upward, the load support bar 328 may transmit a vertical load to the upper actuator 37 to prevent the driving fastening flange 318 from being pushed backward.

A lower or rear drive or actuator 38 may be provided on the lower side of the hip frame 32 so that the rear end of the thigh frame 33 may be pivoted. Like the upper actuator 37, the lower actuator 38 may include a drive 381 and a plunger 382. A drive fastening flange 326 to which the drive 381 of the lower actuator 38 is rotatably connected may be provided at a bottom surface of the front end of the hip frame 32. A plunger fastening flange 327 to which an end of the plunger 382 of the lower actuator 38 is rotatably connected may be provided at the bottom surface of the front end portion of the thigh frame 33.

The drive fastening flange 326 may be positioned higher than the plunger fastening flange 327. The upper actuator 37 may be mounted on the bottom of the seating frame 29 such that the plunger 372 is inclined upward, and the lower actuator 38 may be mounted on the bottom of the seating frame 39 such that the plunger 382 is inclined downward.

The support frame 36 may extend to the bottom of the hip frame 32, and the lower end of the support frame 36 may be connected to the base frame 35. The base frame 35 may have a substantially rectangular shape and may have rounded corners, but a shape of the base frame 35 is not limited.

The support frame 36 may include a pair of frames extending downward at left and right sides (or alternatively front and rear sides) of the hip frame 32. The pair of frames of the support frame 36 may be referred to as a left support frame and a right support frame. The lower end of the left support frame may be connected to the left side of the base frame 35, and the lower end of the right support frame may be connected to the right side of the base frame 35. The support frame 36 and the base frame 35 may be formed integrally as one body, but embodiments disclosed herein are not limited.

The bottom surface of the support frame 36 may pass through or lie along a same horizontal surface as the bottom surface of the base frame 35. When the bedframe 30 is placed on the installation surface, the support frame 36 and base frame 35 may prevent the bedframe 30 from shaking in the left-right direction. The support frame 36 may be further provided on the bottom of the hip frame 32 corresponding to the inner space of the base frame 35.

An optional frame having the same shape as the support frame 36 may be provided on the left edge and the right edge of the hip frame 32, respectively. When a support frame having the same shape as the support frame 36 is further provided at the left and right edges of the hip frame 32, a vertical load acting from the topper 12 and the cushion module 20 may be transmitted to the installation surface, and bending or sagging of the left and right ends of the hip frame 32 may be reduced or prevented. An optional support frame having the same or similar shape as the support frame 36 may be formed at the left and right side ends of the thigh frame 33 and the left and right side ends of the calf frame 34, respectively.

A support structure defined by the vertical bar 314 and the horizontal bar 315 formed at the front end of the upper body frame 31 may be formed in the same manner at the rear end of the calf frame 34. A plurality of lower hinge shaft brackets 325 may be formed on the bottom surface of the front end of the hip frame 32. Like the plurality of upper hinge shaft brackets 324, the plurality of lower hinge shaft brackets 325 may be spaced apart from each other in the left and right direction of the hip frame 32.

A frame or bar defining a front end of the thigh frame 33 may pass through the lower hinge shaft bracket 325 so that the front end of the thigh frame 33 is at the rear end of the hip frame 32. The bar of the front end of the thigh frame 33 may be a rotation center of the thigh frame 33 and define as a lower hinge axis.

The thigh frame 33 may have a shape substantially symmetrical with the hip frame 32, but a shape of the thigh frame 33 is not limited. Front-rear lengths of the hip frame 32 and thigh frame 33 may be configured based on lengths of a human thigh and hip. For example, the thigh frame 33 may be longer than the hip frame 32 in the front-rear direction.

The thigh frame 33, like the hip frame 32, may have a rectangular outer frame 331, at least one first bar or cushion seating plate 332 extending across left and right ends of the outer frame 331, and a plurality of second or connection bars 333 connecting the front end and the rear end of the outer frame 331.

The plunger fastening flange 327 may be provided on the bottom of the front end of the thigh frame 33, and the plunger fastening flange 327 may be provided with the end of the plunger 382 of the lower actuator 38. A plurality of connection flanges 334 may be formed on the left and the right sides of the rear end of the thigh frame 33.

Like the upper body frame 31, the calf frame 34 may include an outer frame 341, at least one first bar or cushion seating plate 342, and at least one second or connection bar 343. The outer frame 341 may have a substantially rectangular shape, and one or more cushion member seating plates 342 may be provided.

A plurality of first bars 342 may be provided on upper surfaces of left and right ends of the outer frame 341, and may be spaced apart in the front-rear direction of the calf frame 34. A plurality of second bars 343 may connect a front end and a rear end of the outer frame 341 and may be spaced apart in the left-right direction of the calf frame 34.

A connection flange 344 having the same shape as the connection flange 334 formed on the rear end of the thigh frame 33 may be formed at the front end of the calf frame 34. The connection flange 334 of the thigh frame 33 and the connection flange 344 of the calf frame 34 may be rotatably connected.

Figure 8:
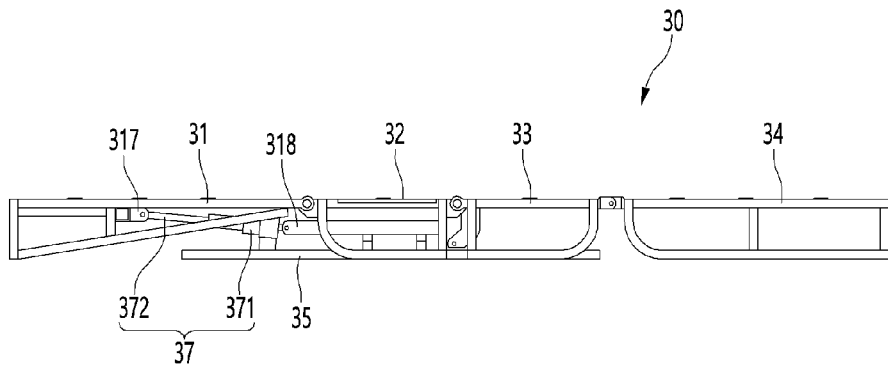
FIG. 8 is a side view of the bedframe in a horizontal state.
Figure 9:
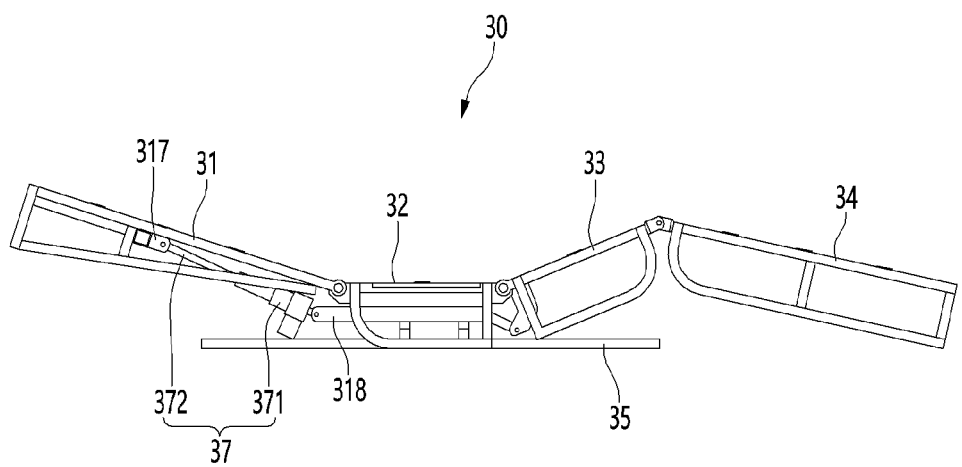
FIG. 9 is a side view of the bedframe in which an upper body frame and a thigh frame are lifted or tilted upward.
Figure 10:
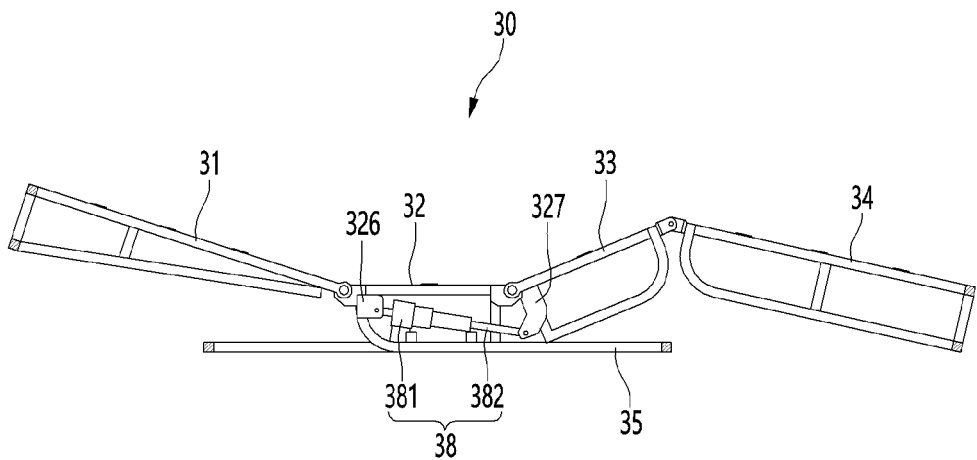
FIG. 10 is a side cross-sectional view of the bedframe cut along 10-10 of FIG. 6 in a tilted state.

Referring to FIGS. 8-10, FIG. 8 shows a flat or default state of the bed 10 where all of the upper body frame 31, the hip frame 32, the thigh frame 33, and the calf frame 34 lie along a same horizontal plane, while FIGS. 9-10 show an adjusted state where both the upper body frame 31 and the calf frame 33 are pivoted relative to the hip frame 43. FIG. 9 shows a state in which the plunger 372 of the upper actuator 37 is extended or elongated, while FIG. 10 shows the plunger 382 of the lower actuator 38 is extended or elongated.

The hip frame 32 may be maintained in a horizontal state, and a load (or rotational moment) transmitted from the upper body frame 31 to the upper actuator 37, in addition to a load transmitted from the thigh frame 33 to the lower actuator 38, may be transmitted to the hip frame 32. Two symmetrical rotational moments transmitted to the hip frame 32 may be countered or balanced by the base frame 35, which may reduce a possibility of the front or rear end of the base frame 35 being lifted up off the installation surface. A length of the base frame 35 may be configured to prevent the base frame 35 and thus the bed 10 from falling or tilting.

Figure 11:
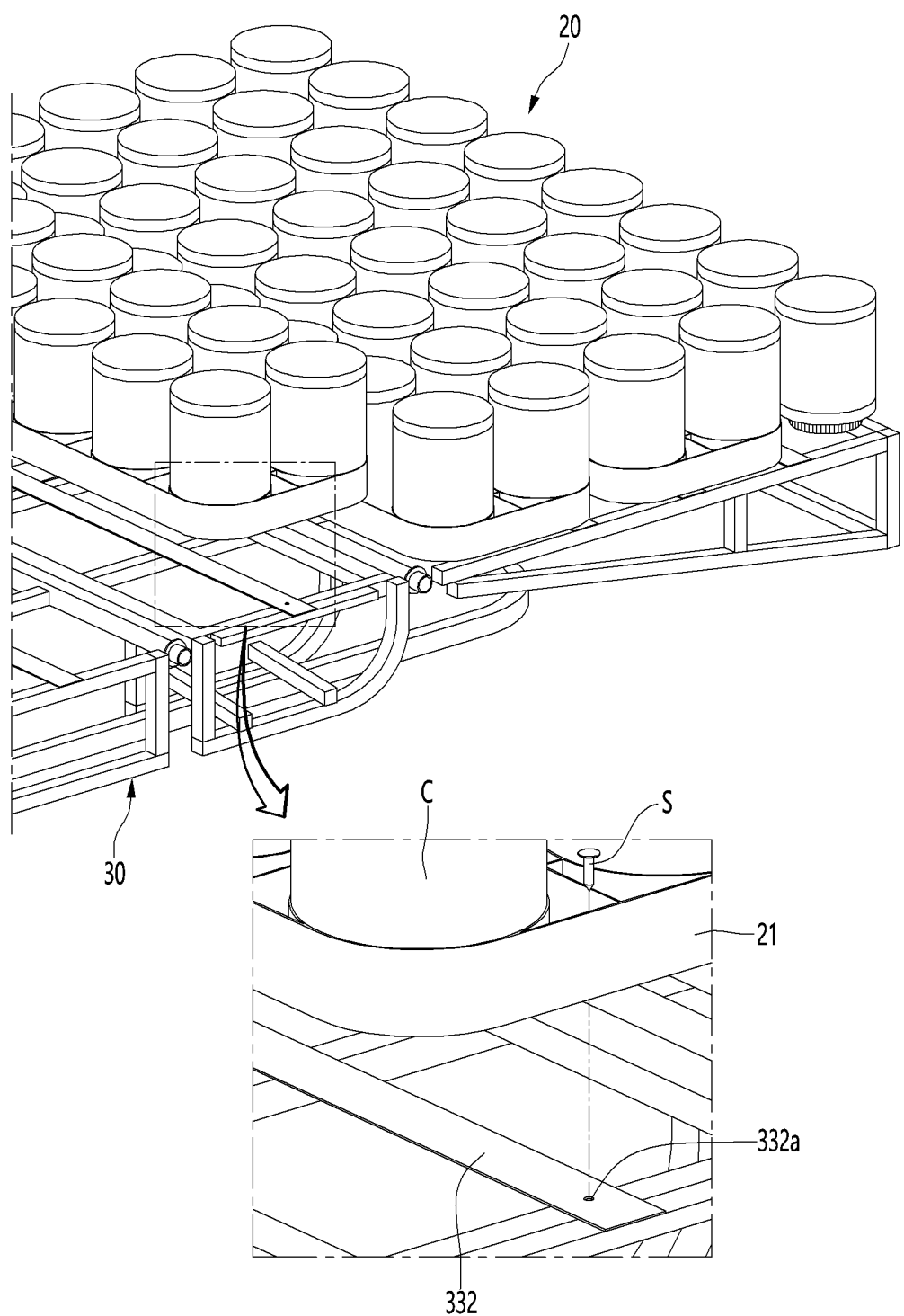
FIG. 11 is a view showing a coupling relationship between a firmness adjuster or cushion module and the bedframe constituting the mattress set according to an embodiment.

Referring to FIG. 11, the cushion module 20 may be an assembly of firmness adjusters M1, each firmness adjuster M1 having an array of cushions C arranged in a cushion case 21. The cushion cases 21 may be placed on the first bars (also referred to as cushion seating plates) 312, 322, 332 and 342 provided on the upper surface of the bedframe 30. The first bars 312, 322, 332, and 342 may be provided at a center of the bottom of the cushion cases 21, but embodiments disclosed herein are not limited.

A fastening member S (e.g., screw or bolt) may be inserted into the first bars 312, 322, 332, 342 through a bottom of the cushion case 21 so that the cushion case 21 and cushions C may be coupled to the bedframe 30. A through hole through which the fastening member S passes may be formed in a center of a bottom of both side ends of the cushion case 21. In addition, a fastening hole 332a through which the fastening member S passes may be formed at left and right edges of the first bars 312,322,332,342, so that both ends of the cushion case 21 may be fixed to the first bars 312, 322, 332, and 342. In addition, an optional adhesive member (e.g., double-sided tape) may be provided on the upper surface of first bars 312,322,332,342 so that a bottom of the cushion case 21 may be further secured to the first bars 312,322,332,342.

Figure 12:
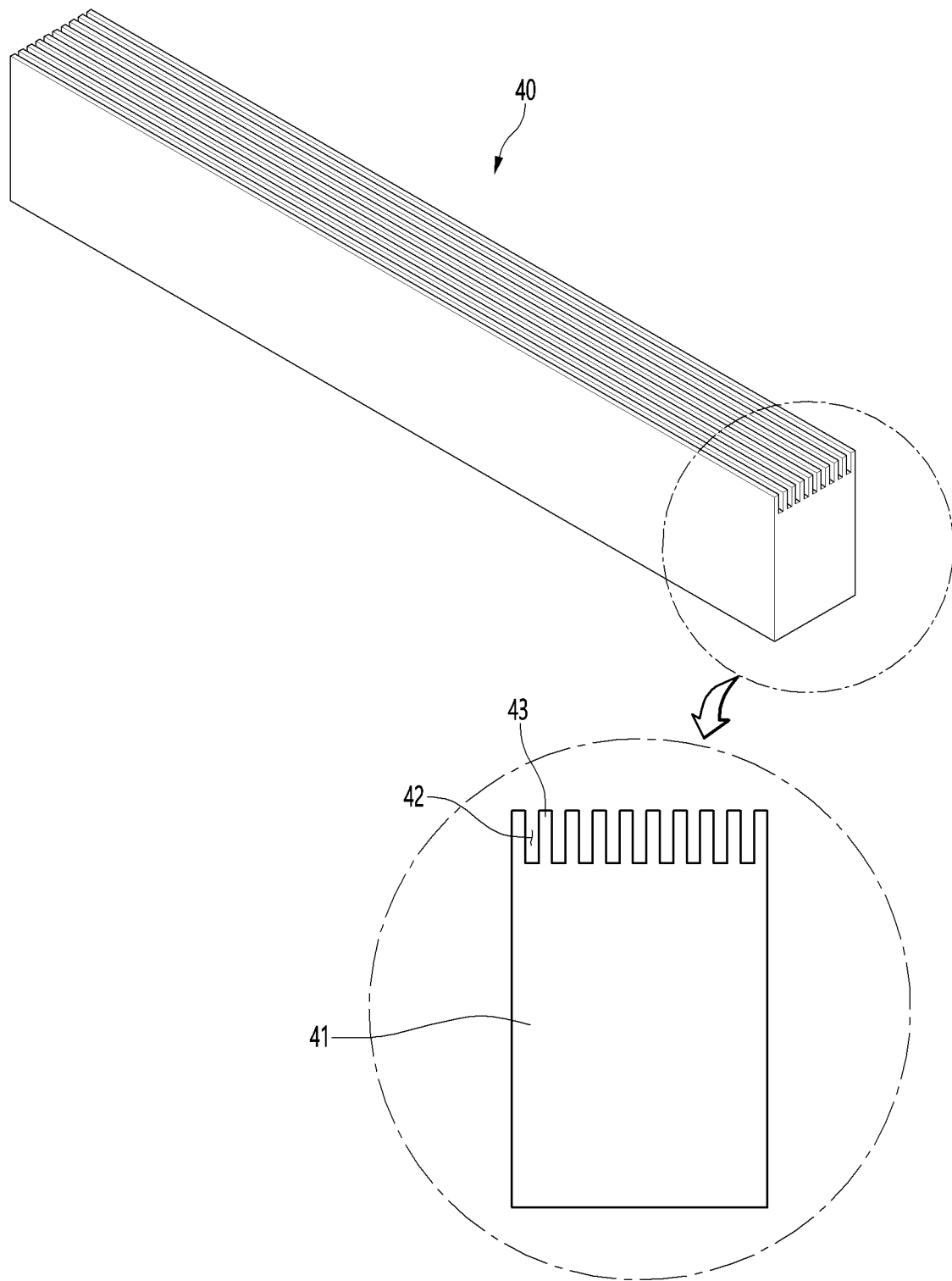
FIG. 12 is a perspective view of a partition constituting a mattress set according to an embodiment.

Referring to FIG. 12, at least one partition or elongated cushion 40 according to an embodiment may be interposed between adjacent firmness modules M1 to prevent interference between adjacent cushions C on opposite sides of a hinge axis of the bedframe 30 during an operation of the bedframe 30. The partition 40 may be provided at a hinge axis between adjacent frames of the bedframe 30.

There may be a plurality of partitions 40 at an upper hinge axis serving as a rotation center of the upper body frame 31, a lower hinge axis serving as a rotation center of the thigh frame 33, and at a calf hinge axis serving as a rotation center of the calf frame 34. Alternatively or in addition thereto, the calf frame 34 may rest on the relative rotating connection flanges 334, 344 (FIG. 7).

The partition 40 provided between the upper body frame 31 and the hip frame 32 may be defined as a first partition. The partition 40 provided between the hip frame 32 and the thigh frame 33 may be defined as a second partition. The partition 40 provided between the thigh frame 33 and the calf frame 34 may be defined as a third partition.

When the upper body frame 31 is tilted upward, the cushion C at the rear end of the upper body frame 31 may approach an upper portion of the cushion C at the front end of the hip frame 32, and without a partition 40 therebetween, may contact the cushion C such that the cushions C become deformed and compressed. Similarly, when the thigh frame 33 is tilted upward, adjacent cushions C (one at the front end of the thigh frame 33 and one at the rear end of the hip frame 32) may approach each other, and, without a partition 40 therebetween, may contact each other to be compressed. By providing the first partition 40 between the upper body frame 31 and the hip frame 32 and the second partition 40 between the hip frame 32 and the thigh frame 33, during a bending motion of the upper body frame 31 and/or the thigh frame 33, the cushions C may contact, press, and deform the partitions 40 instead of other cushions C.

The third partition 40 may have a thickness greater in the front-rear direction than a gap between a cushion C at a rear end of the thigh frame 33 and a cushion C at a front end of the calf frame 34. When the third partition 40 is sandwiched between the thigh frame 33 and the calf frame 34, the third partition 40 may be maintained in a compressed state when no external force is applied and/or the bedframe 30 is in the default state (i.e., a horizontal or flat state).

As the thigh frame 33 is tilted upward, the distance between the cushions C adjacent to the front and rear ends of the third partition 40 may increase. As a result, the third partition 40 may expand by a restoring force such that a front-rear thickness increases toward a natural thickness of the third partition 40. Since the rear end of the thigh frame 33 and the front end of the calf frame 34 may rotate relative to each other, a shape of the third partition 40 may be transformed or extended into a fan or wedge shape having a larger thickness at an upper end than at a lower end.

Each partition 40 may be made of the same material as the topper 12 or the safe guard 13 (e.g., memory foam or latex foam), and thus a shape deformation may occur when an external force is applied. The partition 40 may return to an original state when the external force is removed.

The partition 40 may include a body 41, a plurality of slits 42 formed on an upper end of the body 41, and a plurality of fins 32 defined between the plurality of slits 42. The plurality of slits 42 may be formed at the upper end of the body 41 to facilitate a deformation of the upper end of the partition 40. The plurality of slits 42 and fins 43 may extend in the longitudinal direction of the partition 40 (a width direction or left-right direction of the bedframe 30), and the slits 42 and fins 43 may alternate with each other along a thickness direction of the partition 40 (a length direction or front-rear direction of the bedframe 30).

Figure 15:
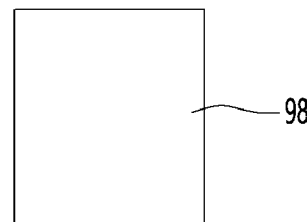
FIG. 15 is an exploded perspective view of the cushion.
Figure 15:
Figure 15:
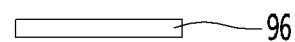
Figure 15:
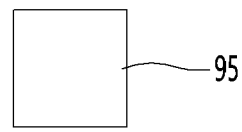
Figure 15:
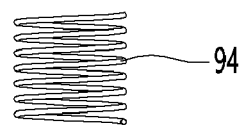
Figure 15:
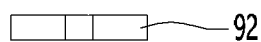
Figure 15:
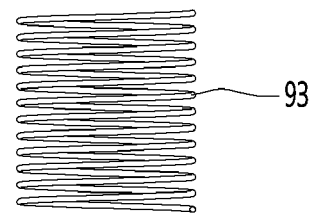
Figure 15:
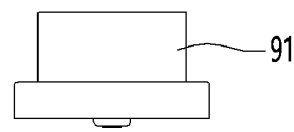
Figure 15:
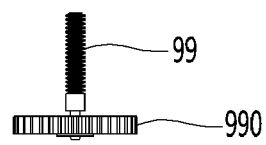

Referring to FIGS. 13 to 15, the cushions C may have a cylindrical or round shape, but embodiments disclosed herein are not limited to a shape of the cushions C. For example, the cushions C may alternatively be rectangular or have polygonal cross-sections. Each cushion C may include an outer case 91, an inner case 92, an outer spring 93, an inner spring 94, an upper cover 97, a lead screw 99, and a transmission gear 990. The cushion C may further include an inner spring cover 95, an outer spring cover 98, and a buffer or inner cover 96.

The outer and inner springs 93 and 94 may each be or include a coil spring wound in a spiral or helix shape, but embodiments disclosed herein are not limited. For example, the outer and inner springs 93 and 94 may alternatively be accordion springs or made of a cushion or other elastic material.

The inner spring 94 may have a diameter smaller than that of the outer spring 93 and may have an elastic modulus or a spring constant smaller than that of the outer spring 93. An elastic strength of the inner spring 94 may be set or predetermined to be smaller than an elastic strength of the outer spring 93. The elastic strength or spring constant may be inversely proportional to an amount of deformation. For example, an amount of deformation of the inner spring 94 may be greater than that of the outer spring 93 with respect to a same applied axial force. As an alternative, the elastic strength or spring constant of the inner spring 94 and the outer spring 93 may be set or predetermined to be equal to each other.

A thread may be formed on an outer circumferential surface of the lead screw 99, and the transmission gear 990 may be coupled to a lower end of the lead screw 99. The lead screw 99 may be rotatably coupled to a center of a bottom of the outer case 91, and the inner case 92 may be screwed onto the outer peripheral surface of the lead screw 99. An inner surface of the inner case 92 may be optionally formed with threads to facilitate coupling to the lead screw 99. By a rotation of the lead screw 99, the inner case 92 may rise or descend along the lead screw 99.

The inner spring cover 95 may surround the inner spring 94 and may include a thin fabric or an elastic material, but is not limited thereto. A shape of the inner spring cover 95 may be deformed according to an elastic deformation of the inner spring 94 and restored based on a restoration of the inner spring 94.

The outer spring cover 98 may surround the outer spring 93 and may be made of a same material as the inner spring cover 95, but embodiments disclosed herein are not limited to materials of the inner and outer spring covers 98 and 95. Like the inner spring cover 95, the outer spring cover 98 may be deformed or restored based on a deformation or restoration of the outer spring 93.

The buffer 96 may be mounted on a bottom surface of the upper cover 92, and an upper end of the inner spring 94 may contact a bottom surface of the buffer 96 to absorb shock and noise. For example, when the inner case 92 is lowered to a point where the upper end of the inner spring 94 is spaced apart from a bottom surface of the upper cover 97, when a vertical force acts or changes on the cushion C, the buffer 96 may absorb noise generated when the inner spring 94 hits a bottom surface of the upper cover 97.

Referring to FIG. 16, the upper cover 97 may have a circular or polygonal cover plate or top plate 971, and a cover sleeve 972 extending downward from an edge of the cover plate 971. A buffer seating recess 971a may be formed on the lower surface of the cover plate 971 to be stepped upward. A bottom surface of the cover plate 971 corresponding to an edge of a buffer seating portion or recess 971a and an inner edge of the cover sleeve 972 may be defined as a spring seating portion or recess 971b. The upper end of the outer spring 93 may be seated on the spring seating recess 971b.

Referring to FIG. 17, the inner case 92 may include a base plate 921 having a circular or polygonal shape. A base sleeve 922 may extend upward from an edge of the base plate 921, and a screw boss 923 may extend upward from a center of the upper surface of the base plate 921.

The base sleeve 922 may have a plurality of guide protrusions 927 protruding in a radial direction, and the plurality of guide protrusions 927 may be spaced apart in a circumferential direction of the base sleeve 922. Each guide protrusion 927 may be formed by bending and extending the base sleeve 922. The guide protrusion 927 may include a pair of side surfaces or walls extending in a radial direction of the base plate 921 and facing each other, and a front surface or wall connecting the pair of side portions.

A screw hole 924 may be formed inside the screw boss 923, and a screw thread 925 may be formed on an inner circumferential surface of the screw hole 924. A plurality of reinforcing ribs 926 may extend radially outward from an outer circumferential surface of the screw boss 923. A lower end of the inner spring 94 may be provided in a space between outer ends of the plurality of reinforcing ribs 926 and an inner circumferential surface of the base sleeve 922. The plurality of reinforcing ribs 926 may reinforce a strength of the screw boss 923 and also reduce or prevent a movement of the inner spring 94 in the radial direction.

One or more holes or slits 928 may be formed in the base plate 921 at positions circumferentially between sides of the reinforcing ribs 926. The holes 928 may be formed to be closer to an outer surface of the screw boss 923 than outer ends of the reinforcing ribs 926, but embodiments disclosed herein are not limited.

Referring to FIG. 18, the outer case 91 may include a bottom plate 911 having a circular or polygonal shape and a case sleeve 912 extending upward from an upper surface of the bottom plate 911. The case sleeve 912 may have a diameter smaller than a diameter of the bottom plate 911.

A spring flange 913 may be bent and extended upward from an outer edge of the bottom plate 911, and the spring flange 913 may radially surround the case sleeve 912. The upper surface of the bottom plate 911 between the spring flange 913 and the case sleeve 912 may be defined as a spring mounting space or recess 914 in which a lower end of the outer sleeve 93 may be seated or mounted.

A pair of guide ribs 915 may extend radially inward from an inner circumferential surface of the case sleeve 912 to define a guide space. The guide ribs 915 in the pair of guide ribs 915 may be spaced apart in a circumferential direction of the case sleeve 912. A plurality of pairs of guide ribs 915 may further be spaced apart from each other along the circumferential direction.

The guide protrusions 927 of the inner case 92 (FIG. 18) may be fitted in the guide space between the pair of guide ribs 915. A position and number of guide spaces formed by the pair of guide ribs 915 may correspond to a position and a number of the guide protrusions 927.

A screw hole 916a may be formed in a center of the bottom plate 911. A support sleeve 916 may extend upward at an edge of the screw hole 916a. The lead screw 99 may pass through the screw hole 916a.

A plurality of air holes or slots 917 may be spaced apart from each other in a circumferential direction in the bottom plate 911. Each of the plurality of air holes 917 may be formed in a long hole or arc shape that curves to be round in the circumferential direction of the bottom plate 911, but a size or shape of the air hole 917 is not limited thereto. The air holes 917 may be provided at positions that are circumferentially between adjacent pairs of guide ribs 915 and/or at positions radially inward from the guide ribs 915, but embodiments disclosed herein are not limited. Air discharged upward from a dryer module 50 described later may pass through the air holes 917 to dry the cushions C and/or the topper 12.

A plurality of vibration preventing ribs 918 may protrude from an upper surface of the bottom plate 911 at an inner edge of the case sleeve 912. The vibration prevention ribs 918 may protrude radially inward from an inner peripheral surface of the case sleeve 912 toward a center of the bottom plate 911. A side of the vibration prevention rib 918 facing the center of the bottom plate 911 may be curved or rounded, and the vibration prevention rib 918 may have a semicircle or elliptical shape, but embodiments disclosed herein are not limited.

Referring to FIG. 19, the pair of guide ribs 915 may contact both side surfaces of the guide protrusions 927 formed on the inner case 92. The guide protrusion 927 may be supported by the guide rib 915 to prevent or reduce a spinning movement of the inner case 92 in the circumferential direction when the inner case 92 is raised or lowered. When the inner case 92 descends to a bottom surface of the outer case 91, the vibration prevention rib 918 may contact an outer circumferential surface of the inner case 92 to prevent or reduce rattling of the inner case 92 along the radial direction and reduce or prevent noise.

Figure 20:
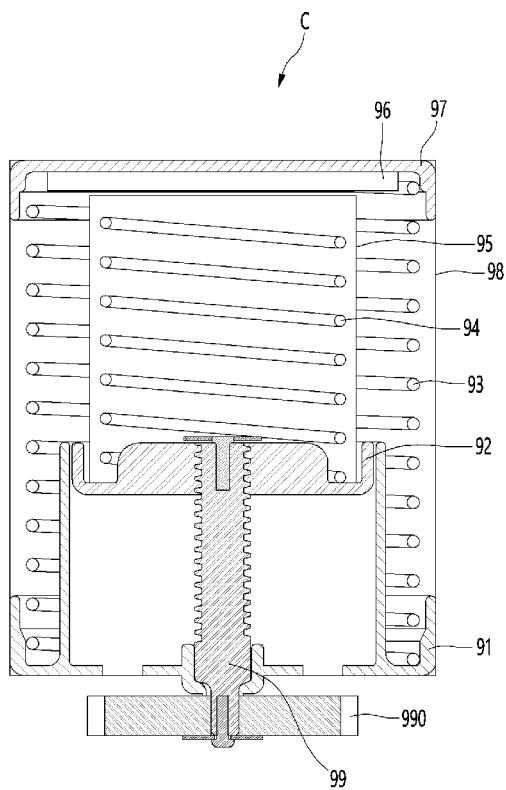
FIG. 20 is a longitudinal sectional view of a cushion according to an embodiment cut along 20-20 of FIG. 13 in a state in which no external force is applied.
Figure 21:
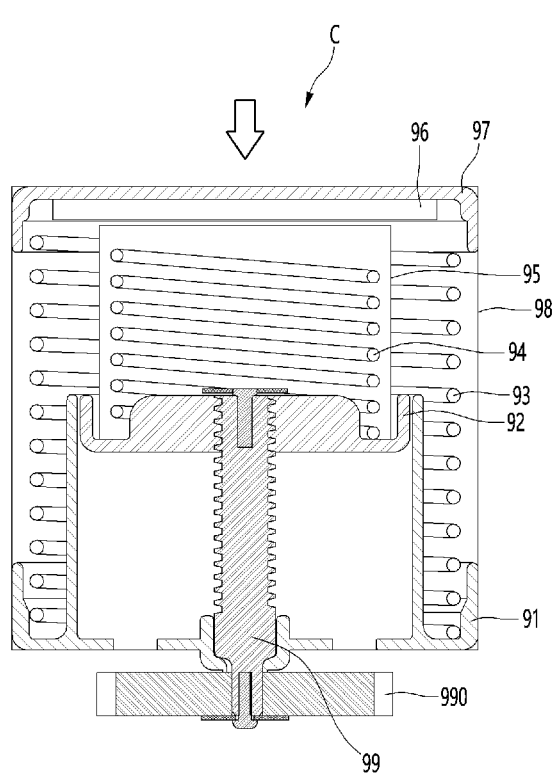
FIG. 21 is a longitudinal sectional view of a cushion according to an embodiment cut along 20-20 of FIG. 13 in a state in which an external force is applied.

Referring to FIGS. 20 and 21, the lead screw 99 may be rotated in a clockwise or counterclockwise direction to adjust a height of the inner case 92. In a basic state in which no external force is applied, the upper end of the inner spring 94 may or may not touch the buffer 96 depending on the height of the inner case 92.

When an external force in the vertical direction acts on the upper surface of the cushion C, the outer cover 97 may descend and compress the outer spring 93 and the inner spring 94 simultaneously, or, the outer spring 93 may be first compressed before the inner spring 94 and outer spring 93 are compressed together.

A firmness or cushion strength of the cushion C may be adjusted by adjusting a height of the inner spring 94. When the lead screw 99 is rotated so as to raise the inner spring 94 to have a height similar to a height of the outer spring 93, when a user sits on the bed, both the outer and inner springs 93 and 94 may be compressed. As a weight of the user acts on both the outer and inner springs 93 and 94, a deformation amount of each of the outer and inner springs 93 and 94 may be less than if all of the weight of the user acted on only one of the outer or inner springs 93 and 94. When the outer and inner springs 93 and 94 are compressed at a same time, the user may perceive an increased firmness. When the lead screw 99 is rotated so as to lower the inner spring 93 so that a height of a top of the inner spring 94 is significantly below a height of the top of the outer spring 93, the weight of the user may act on the outer spring 93, a deformation amount of the outer spring 93 may be greater, and the user may perceive a decreased firmness. The upper cover 97 and/or inner cover 96 may prevent or reduce an uncomfortable feeling from a protruding end of the lead screw 99 when the inner spring 94 is lowered.

Figure 22:
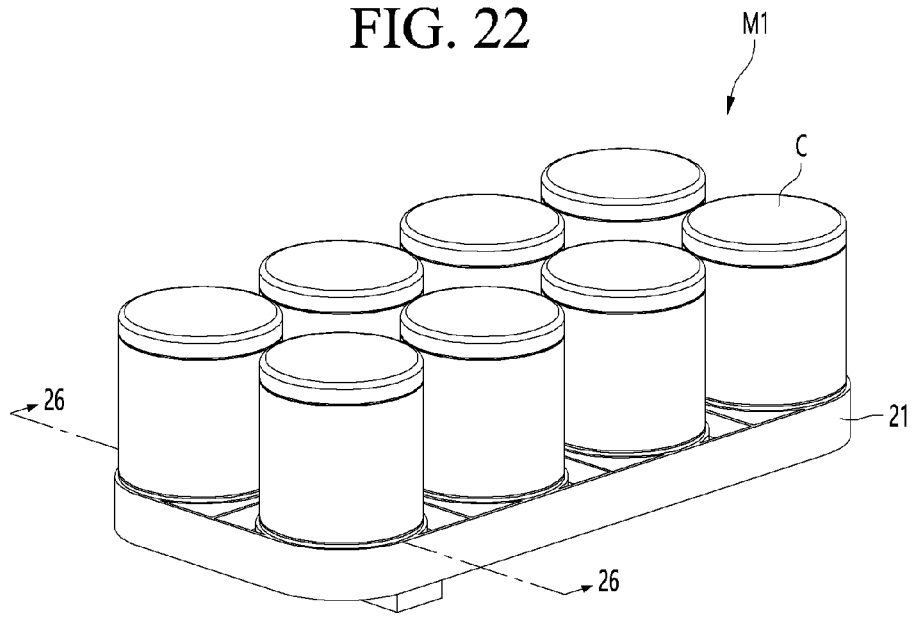
FIG. 22 is a side perspective view of the firmness adjuster according to an embodiment.
Figure 23:
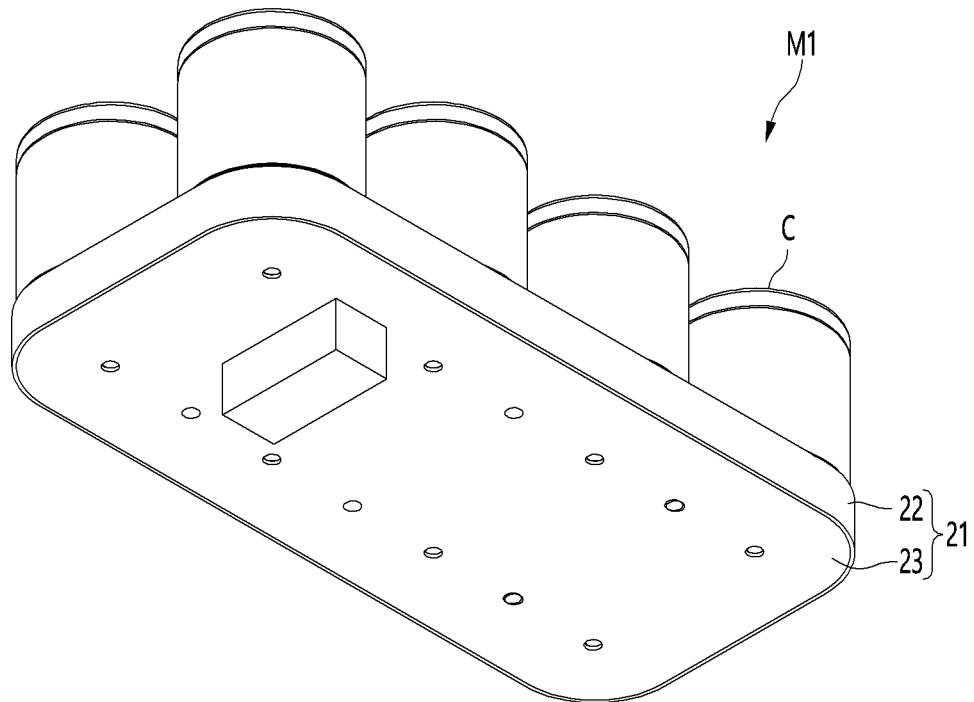
FIG. 23 is a bottom perspective view of the firmness adjuster.

Referring to FIGS. 22 and 23, the cushion module 20 may include a plurality of firmness adjusters M1 each having a cushion case 21 and a plurality of cushions C arranged in the cushion case 21. The Figures show that one firmness adjuster M1 may have eight cushions C, but embodiments disclosed herein are not limited to eight cushions C per firmness adjuster M1. The firmness adjuster M1 may include a drive 24 (e.g., motor or actuator) (See FIG. 25) to collectively and equally adjust an elastic strength of the cushions C.

There may be a plurality of firmness adjusters M1 corresponding to various areas of the bed. For example, there may be one firmness adjuster M1 for each of the upper frame 31, hip frame 32, thigh frame 33, and calf frame 34. As another example, there may be two firmness adjusters M1 for each of the upper, hip, thigh, and calf frames 31-34, one for each of the left and right sides of the upper, hip, thigh, and calf fames 31-34. Embodiments disclosed herein are not limited to an arrangement of firmness adjusters M1.

Figure 24:
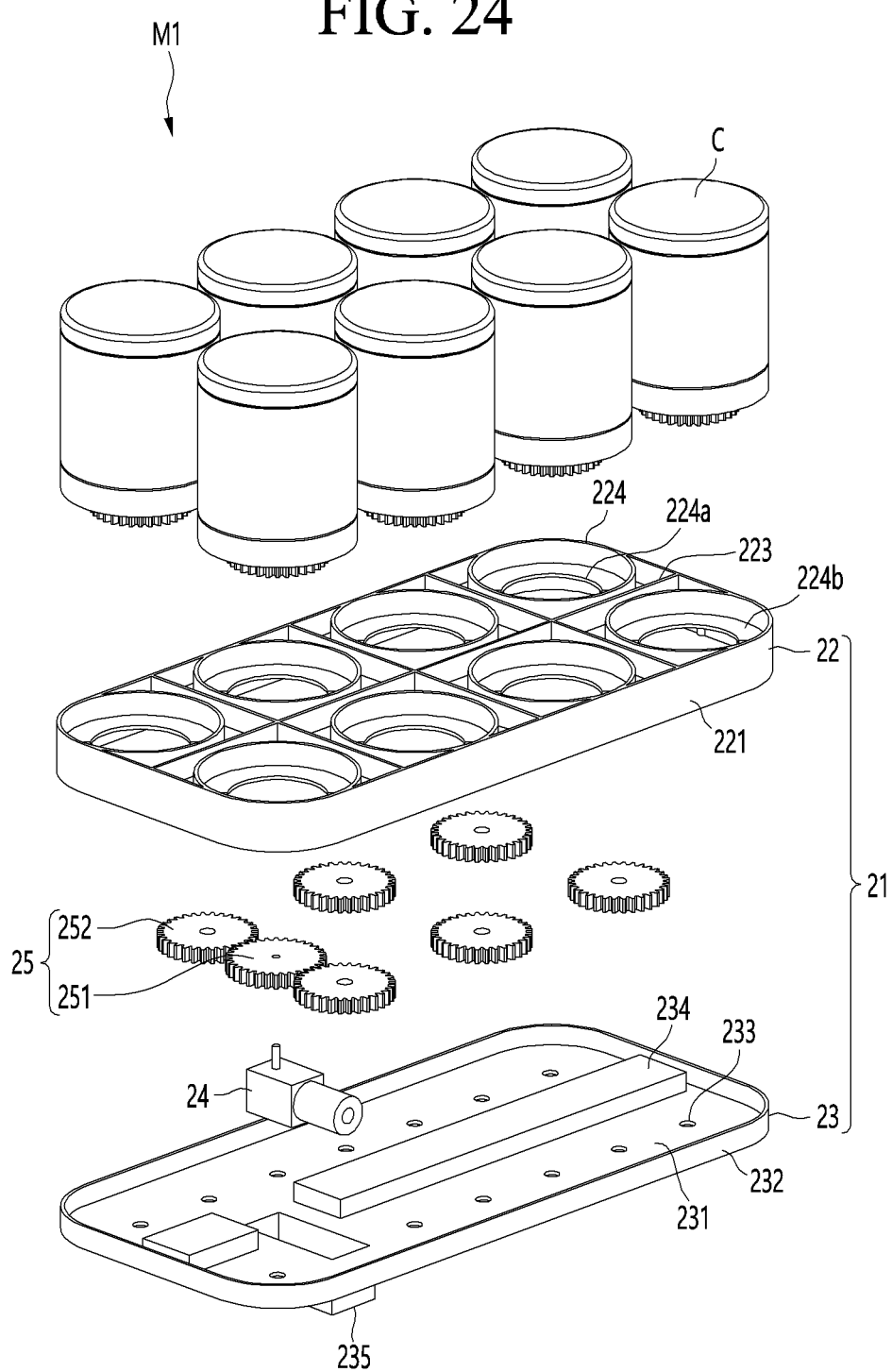
FIG. 24 is an exploded perspective view of a firmness adjuster according to an embodiment.

The cushion case 21 may include a bottom or outer case 23 and an upper or inner case 22. The drive 24 may be provided in a motor or drive housing 235, which may be a recess or cavity formed in a bottom of the bottom case 23 (FIG. 24). The drive 24 may be provided between an upper surface of the bottom case 23 and a bottom surface of the upper case 22.

Figure 25:
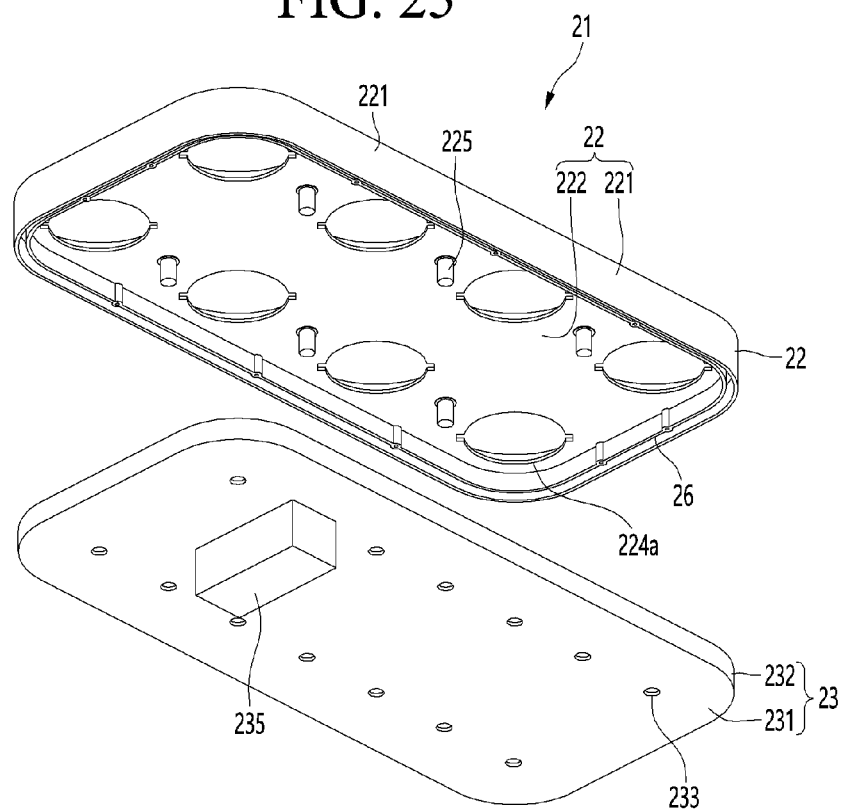
FIG. 25 is an exploded perspective view showing a bottom structure of a cushion case constituting the firmness adjuster.

Referring to FIGS. 24 and 25, the drive 24 may include a drive motor. For convenience of description, the drive 24 will be hereinafter referred to as a motor 24. A gear assembly 25 may be rotatably moveable via the motor 24. For example, FIG. 25 shows that a rotation shaft may extend from the motor 24 to couple to the gear assembly 25 so that a rotation force of the motor 24 is transmitted to the gear assembly 25.

The upper case 22 may include an outer frame or wall 221 formed in a rectangular shape with a predetermined height, and an inner plate 222 formed inside the outer wall 221. The inner plate 222 may be provided a predetermined distance upward from a lower end of the outer wall 221 to divide the inner space of the upper case 22 into an upper space and a lower space. The gear assembly 25 may be provided in the lower space of the upper case 22, and the plurality of cushions C may be provided in the upper space of the upper case 22.

A plurality of gear shafts 225 may protrude from the bottom surface of the inner plate 222 so that gears G to be described later may be rotatably mounted. A plurality of partition plates or walls 223 may protrude from the upper surface of the inner plate 222 to divide the upper space of the outer frame 221 into a plurality of small spaces in which the cushions C may be provided.

The plurality of partition plates 223 may include a plurality of horizontal or first partition plates 223 extending in the width direction of the upper case 22 and arranged at equal intervals in the length direction, and at least one vertical or second partition plate 223 extending in the length direction of the upper case 22. The second partition plate 223 may divide the upper space of the outer frame 221 into left and right sides.

A number of second partition plates 223 may be determined according to a number of rows (extending in the front-rear direction) in which the plurality of cushions C are arranged, and the number of first partition plates 223 may be determined according to a number of rows or columns (extending in the left-right direction) in which the plurality of cushions C are arranged.

A support sleeve or flange 224 may extend in each of a plurality of small spaces partitioned by the first and second partition plates 223, and a through hole 224a may be provided in the inner plate 222 at an inner side of the support sleeve 224. The support sleeve 224 and the partition plates 223 may have a same or similar height, and an inner diameter of the support sleeve 224 may correspond to an outer diameter of the cushion C.

The through hole 224a may have a diameter smaller than an inner diameter of the support sleeve 224. A seating surface 224b may be formed on the upper surface of the inner plate 222 at an inner bottom of the support sleeve 224 to support an outer edge of the cushion C.

A diameter of the through hole 224a may have a size corresponding to or slightly bigger than that of an outer diameter of the transmission gear 990 so that when the cushion C is seated inside the support sleeve 224 on the seating surface 224b, the transmission gear 990 may be exposed through or pass through the through hole 224a to the lower space of the outer frame 221.

A seal or a gasket 26 may be provided at an edge of the lower space of the upper case 22 to reduce or prevent an inflow of foreign matter through a coupling portion or area between the bottom case 23 and the upper case 22. The seal 26 may also reduce or prevent noise (e.g., noise of the gear assembly 25) generated in the lower space of the outer frame 221.

The bottom case 23 may include a bottom plate 231 and a side wall 232 extending upward from an edge of the bottom plate 231. The side wall 232 may contact the inner circumferential surface of the outer frame 21 defining a lower space of the upper case 22. The seal 26 may contact an upper end of the side wall 232 and/or may be fitted between an outer circumferential surface of the upper end of the side wall 232 and the inner circumferential surface of the outer wall 221. Alternatively, the side wall 232 may fit in a space between the seal 26 and the outer wall 221.

The seal 26 may be made of an elastic, rubber, or plastic material, and may extend downward from the bottom surface of the upper case 22. The seal 26 may be provided at an inner side of the outer wall 221 and extend along an outer side or perimeter of the bottom surface of the upper case 22.

A plurality of shaft holes 233 may be formed in the bottom plate 231 at positions directly below or aligning with the plurality of gear shafts 225. Alternatively, the shaft holes 223 may be omitted, and a length of the gear shaft 225 may correspond to a depth of the lower space of the upper case 22 (i.e., a distance between the bottom surface of the inner plate 222 and the bottom plate 231). As another alternative, the shaft holes 223 may instead be formed by recessing an upper surface of the bottom case 23 downward.

A motor housing 235 to house the motor 24 may protrude from a bottom surface of the bottom plate 231. The motor housing 235 may be formed such that a portion of the bottom plate 231 is recessed or stepped downward by a predetermined depth. Alternatively, a communication hole may be formed in the bottom plate 231, and a separate housing may be coupled to a bottom of the bottom plate 231 at a position directly below the communication hole to define the motor housing 235.

The gear assembly 25 may include a drive gear 251 driven by the motor 24 and at least one driven gear 252 configured to engage with and be driven by the drive gear 251. The transmission gears 990 of the cushions C may be adjacent to the driven gears 252. There may be idle gears not part of the cushions C that are provided between adjacent transmission gears 990 so as to transmit a rotational force to the transmission gears 990 that are part of the same firmness adjuster M1. Alternatively, when there is a plurality of driven gears 252, all of the plurality of driven gears 252 may be defined as idle gears. As another alternative, there may be one driven gear 252 and a plurality of idle gears. Embodiments disclosed herein are not limited to an arrangement of the gear assembly 25 and the transmission gears 990. The gear shaft 225 may extend from the bottom surface of the inner plate 222, but alternatively, the gear shaft 225 may extend upward from the top surface of the bottom plate 231.

A spacer 234 may be provided in a center of the bottom plate 231 in a space between two rows of transmission gears 990 that extend in a length direction of the cushion case 21. The spacer 234 may be a panel or frame extending in the length direction, but embodiments disclosed herein are not limited.

The spacer 234 may prevent the driven gears 252 or idle gears from being moved in a width direction of the module case 21 and disrupting a gear coupling of the gear assembly 25 and the transmission gears 990. The spacer 234 may have a height corresponding to a gap between the inner plate 222 and the bottom plate 231, and may prevent or reduce sagging of the inner plate 222 The spacer 234 may optionally be configured to add structural rigidity to the cushion case 21.

Figure 26:
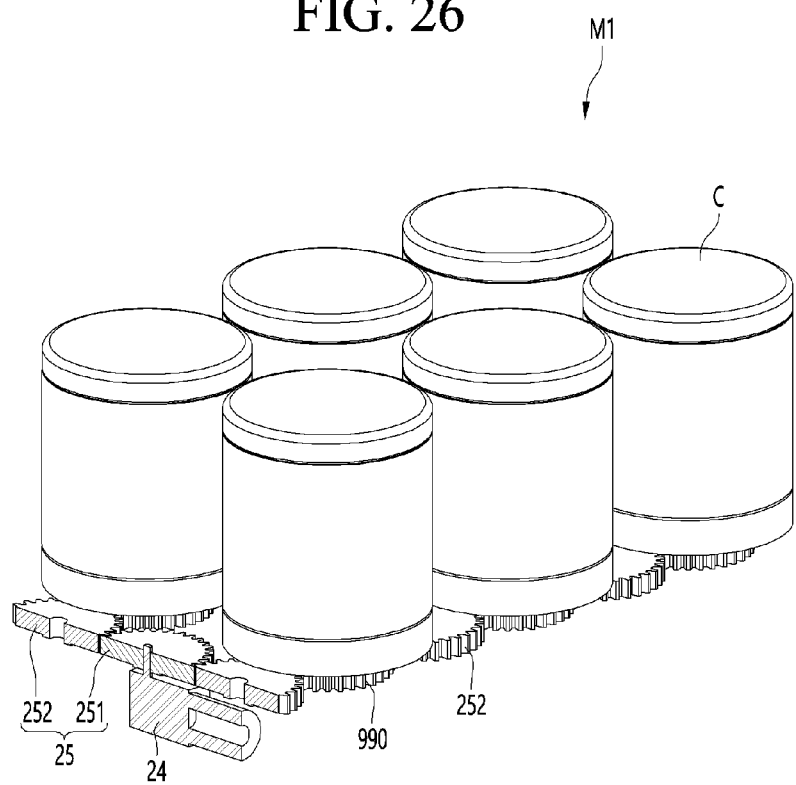
FIG. 26 is a perspective view of the firmness adjuster according to the embodiment cut along 26-26 of FIG. 22.
Figure 27:
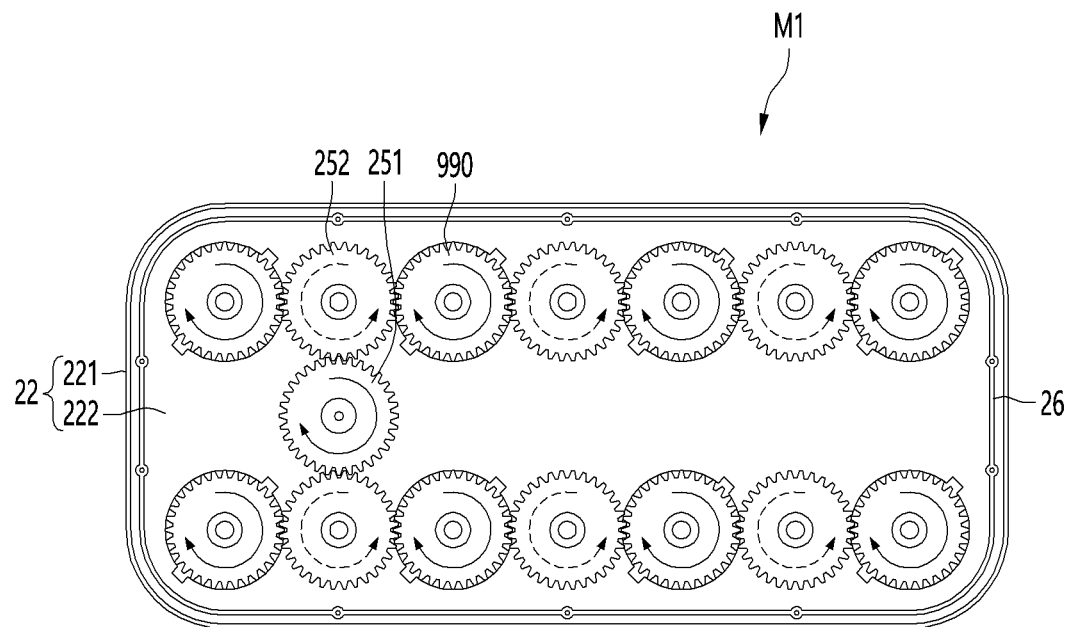
FIG. 27 is a bottom view of the firmness adjuster according to an embodiment where a bottom case is removed.
Figure 28:
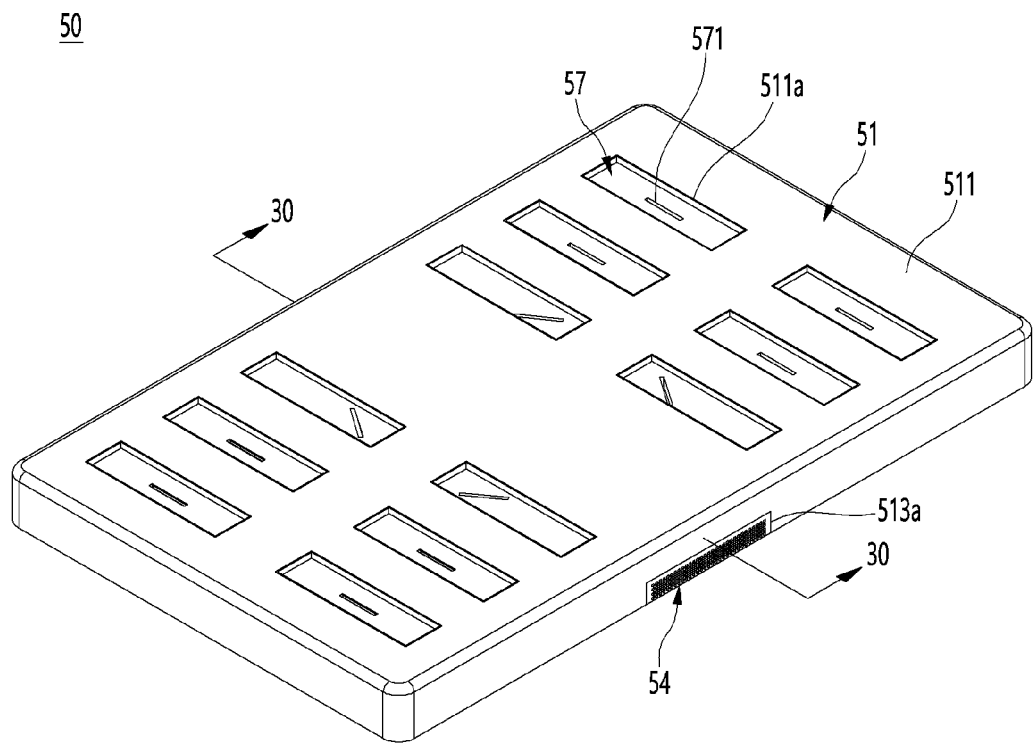
FIG. 28 is a perspective view of a drying module or dryer constituting a bed according to an embodiment.

Referring to FIGS. 26 and 27, the transmission gears 990 and the driven gears 252 may be alternately arranged with each other, and all of the transmission gears 990 may rotate in the same direction. A rotational force supplied from the motor 24 may be transmitted to the driven gear 252 through the driving gear 251, and the rotational force transmitted to the driven gear 252 may be transmitted to a transmission gear 990 and subsequent transmission gears 990 via other driven gears 252 or idle gears. For convenience of description, a gear directly connected to the drive gear 251 may be defined as the driven gear 252, while a gear provided between adjacent transmission gears 990 may be defined as the idle gear.

The drive gear 251 may be engaged with a driven gear row located at an outer side or end (e.g., a front end) of the cushion case 21, but embodiments disclosed herein are not limited. For example, the motor 24 and motor housing 235 may be provided at a center of the bottom case 23, and the drive gear 251 and driven gear 252 may be provided in a middle or center portion of the bottom case 23, with idle gears provided at either side or end.

When a firmness for a particular area of the bed is set through a user interface provided in the bed (e.g., at the side guard 13 or guard rail 60, in a humidity controller 800 descried later, or in some other remote controller or device such as a phone or computer through a mobile or web application), the motor 24 of a corresponding firmness adjuster M1 may rotate, a rotational force may be transmitted to the gear assembly 25, and the plurality of cushions C in a same firmness adjuster M1 may be controlled to have a same elastic strength. Further, the user may desire that a firmness of the bed (or alternatively, half the bed) be uniform, in which case, all of the firmness adjusters M1 may be controlled such that all of the cushions C have the same firmness.

In addition, although the Figures show a 2×4 arrangement of the cushions C in each firmness adjuster M1, embodiments disclosed herein are not limited to such a number or arrangement and may be customized, along with a size of the cushions C and an overall size of the firmness adjuster M1. When a plurality of cushions C is provided in one row, one driven gear 252 may be connected to the driving gear 251. When three or more rows of cushions C are provided, if idle gears are provided between adjacent driven gears 252, a firmness of three or more rows of cushions C can be controlled with one motor 24.

Referring to FIGS. 28 to 31, the drying module 50 may include a set support 51 to support the mattress set MS. The set support 51 may include a blowing device or fan module 52 mounted at a bottom of the set support 51.

The blowing device 52 may include a fan 55, a suction duct 53 coupled to an inlet of the fan 55, and at least one supply duct 56 coupled to at least one outlet, respectively, of the fan 55. The suction duct 53 may be omitted if the drying module 50 is spaced apart from the installation surface (e.g., when the bed 10 has legs) such that the fan 55 may suction air directly through the inlet of the fan 55. A filter 54 may be provided at a suction port 531 of the suction duct 53; alternatively, if the suction duct 55 is omitted, the filter 54 may be provided at an inlet of the fan 55.

The fan 55 may be provided on an upper surface of the suction duct 53, as the fan 55 may be a centrifugal fan having an inlet provided on a bottom, while the outlet may be provided at a side. The upper surface of the suction duct 53 may include a fan mounting hole 532 in which the fan 55 may be mounted. An inlet of the fan 55 may align with the fan mounting hole 532.

Figure 29:
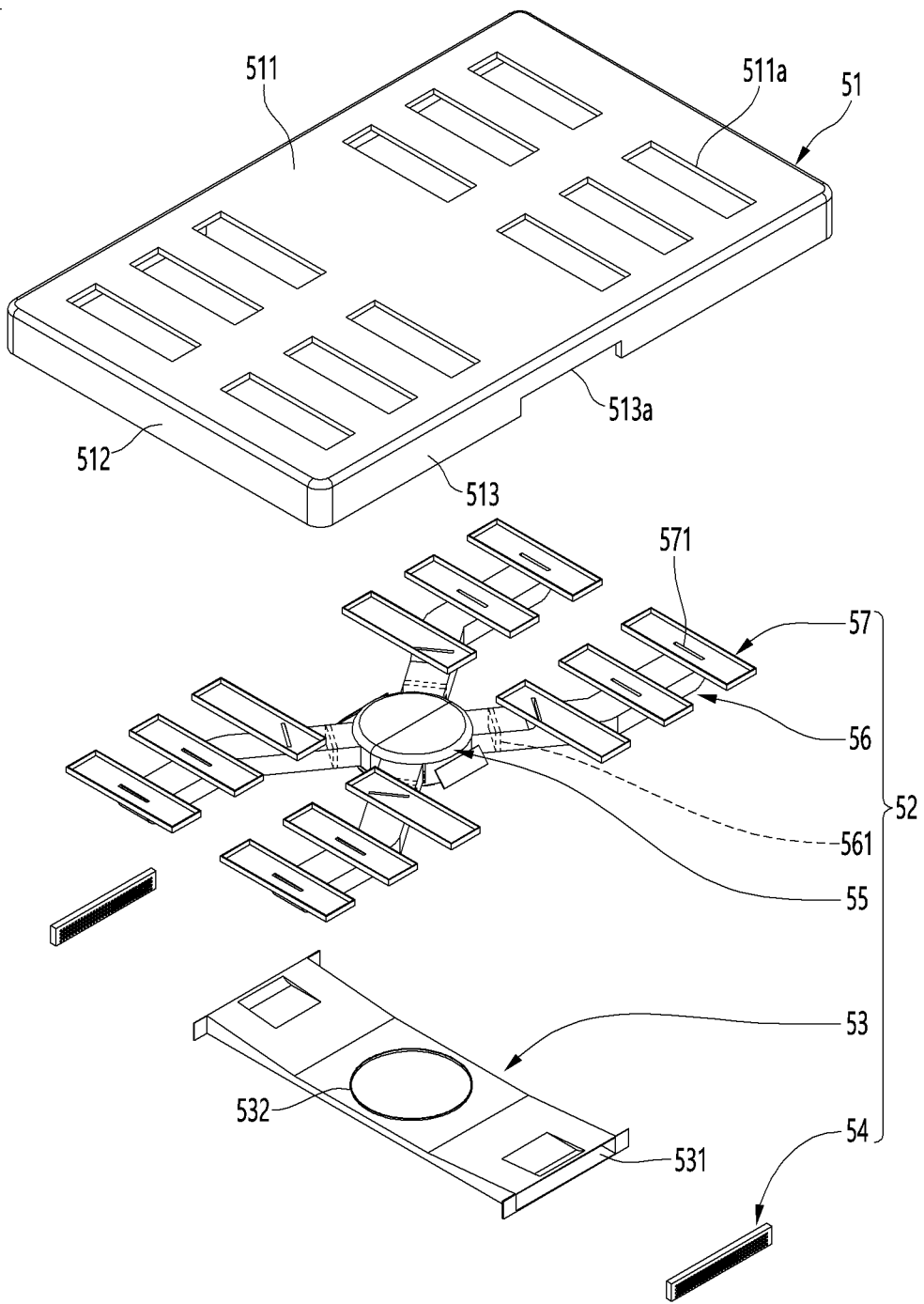
FIG. 29 is an exploded perspective view of the drying module.
Figure 30:
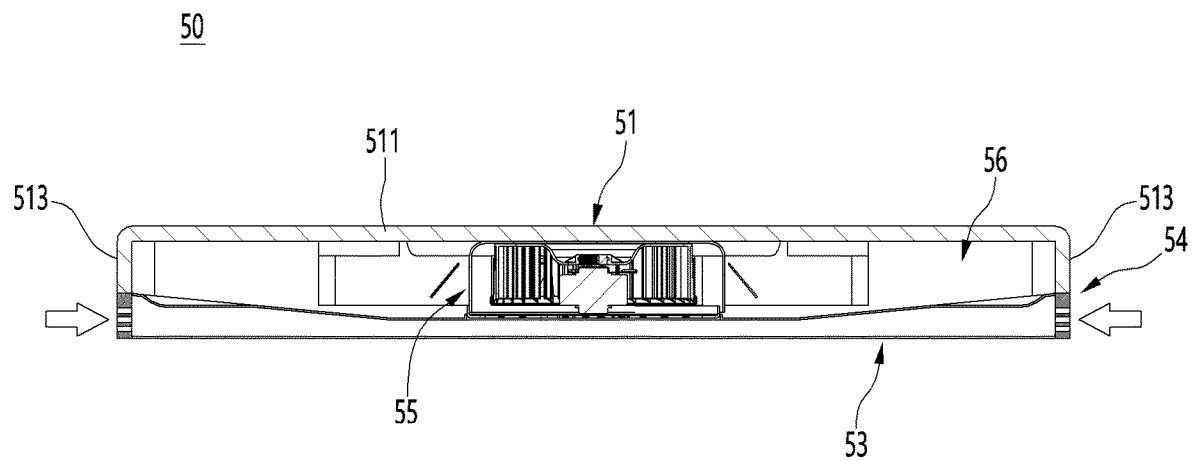
FIG. 30 is a longitudinal sectional view of the drying module taken along 30-30 of FIG. 28.
Figure 31:
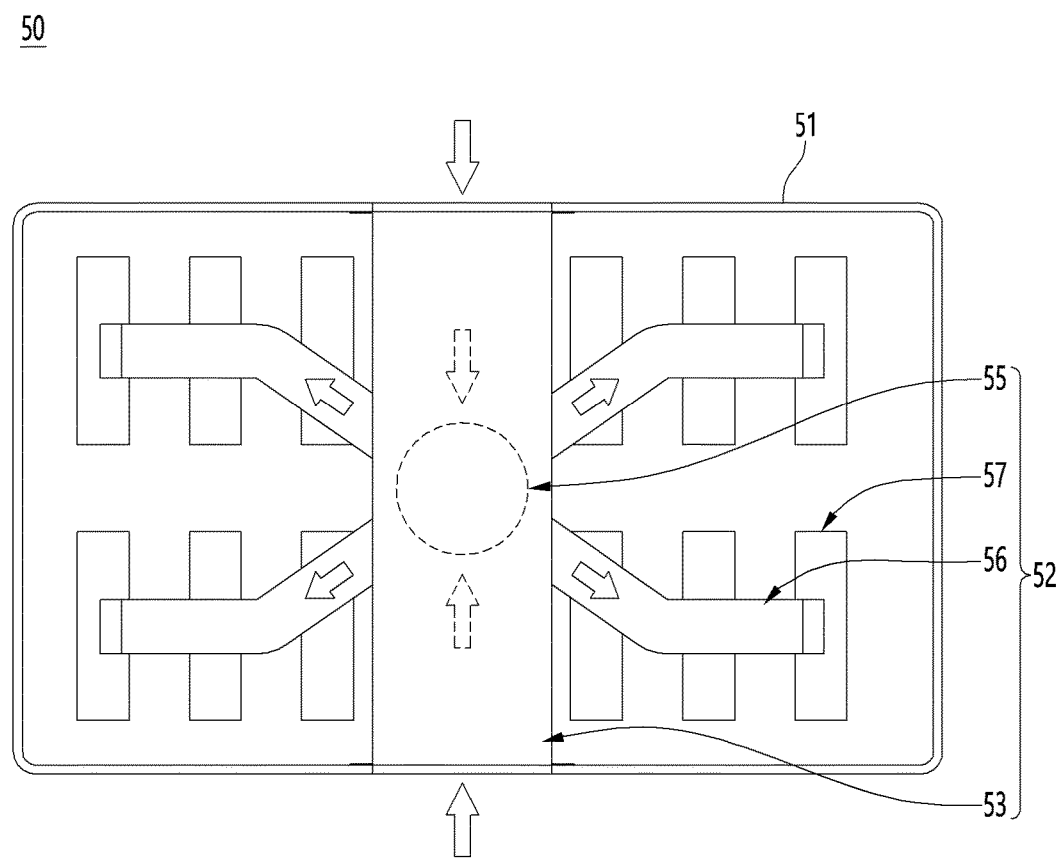
FIG. 31 is a bottom view of the drying module showing air flow.

The supply duct 56 may be mounted at the outlet of the blowing fan 55, and the supply duct 56 may include at least one discharge duct 57 having a discharge port 571 through which air is discharged upward toward the mattress set MS. As shown in FIG. 29, the fan 55 may have four outlets, four supply ducts 56 may be provided, and each supply duct 56 may have three discharge ducts 57; however, embodiments disclosed herein are not limited to a number of supply ducts 56 and discharge ducts 57.

The set support 51 may include an upper surface 511, on which the mattress set MS may be placed, and first and second sides 512 and 513 extending downward from an edge of the upper surface 511. The first sides 512 may be shorter sides along a width direction of the dryer module 50, and the second sides 513 may be longer sides along a length direction of the dryer module 50. For convenience of description, the first sides 512 will be referred to as short sides, and the second sides 513 will be referred to as long sides. The lengths of the short and long sides 512 and 513 may be equal to or longer than the widths and lengths, respectively, of the mattress set MS so as to support the mattress set MS.

When the set support 51 is placed on the installation surface, the lower ends of the short sides 512 and the long sides 513 may contact the installation surface, and an inlet groove or recess 513a may be formed in at least one of the long sides 513. The filter 54 and/or a front edge of the suction port 531 of the supply duct 53 may fit within the inlet recess 513a, and the filter 54 may be exposed through the inlet recess 513a. As the short and long sides 512 and 513 may contact the installation surface, unfiltered air in a bedroom may be prevented or at least slowed from entering the supply duct 53 or an inlet of the fan 55. Ambient air may be suctioned through the filter 54 into the supply duct 53 at the inlet recess 513a. A size and shape of the inlet recess 513a may correspond to a size and shape of the filter 54.

As shown in the Figures, the supply duct 53 may have two suction ports 531 at opposite ends, and both long sides 513 of the bed 10 may be formed with inlet recesses 513a, which may face each other. When one of the long sides 513 is pushed up against a wall (such as when the bed 10 is provided in a corner of a bedroom), air may still be suctioned through the inlet recess 513a and filter 54 at the other long side 513.

A plurality of discharge or mounting holes 511a may be formed in the upper surface 511. The plurality of discharge holes 511a may be formed at positions corresponding to the positions of the plurality of discharge ducts 57 and have a size and shape corresponding to a size and shape of the discharge ducts 57. The plurality of discharge ducts 57 may be exposed through the plurality of discharge holes 511a such that a flow of air discharged from the discharge ports 571 may not be obstructed by the set support 51.

The filter 54 may be optionally detachable from the inlet recess 513a and/or the discharge port 531 to allow access to an inside of the suction duct 53. The suction duct 53 may be fixed to a bottom of the set support 51 in a direction intersecting with the supply duct 56. As an example, the suction duct 53 may extend to be parallel with the short sides 512, while the supply duct 56 may at least partially extend in a direction parallel with the long sides 513. The discharge duct 57 may be parallel to the suction duct 53. When the suction duct 53 extends to be parallel with the long sides 513, the inlet recess 513a may be formed in the long sides 513. Embodiments disclosed herein are not limited to an arrangement of the suction, supply, and discharge ducts 53, 56, and 57.

The fan mounting hole 532 may be formed at a center of the upper surface of the suction duct 53 so that the ambient air passing through the filter 54 and the suction port 531 passes through the fan mounting hole 532. Since the filter 54 may be mounted at the suction port 531 of the suction duct 53, when ambient air is suctioned into the suction duct 53, dust and other foreign matter (e.g., collecting on the installation surface under or near the bed 10) may be effectively filtered out.

As previously described, the fan 55 may include a centrifugal fan that suctions air in the axial direction and discharges the air in the radial direction, but other types of fans may be used. The inlet of the fan 55 may be formed on a bottom surface of the fan 55, and a plurality of discharge ports may be formed on a side surface of the fan 55. The plurality of discharge ports may be spaced apart along a circumferential direction of the fan 55. For example, the Figures show that four outlets are formed on the side of the fan 55, and four supply ducts 56 are connected to the four outlets of the fan 55.

The four supply ducts 56 may have a diagonal portion that intersect in an X-shape with the fan 55 at a center, and a horizontal portion extending parallel to at least one of the short or long sides 512 or 513 toward an edge of the set stopper 51. As shown in FIG. 29, the horizontal portions of the supply ducts 56 may be parallel to the long sides 513 such that the supply ducts 56 extend toward the short sides 412 near the four corners of the bed 10.

When looking at an arrangement of the supply ducts 56 and the fan 55, an arrangement may be symmetrical with respect to a first axis intersecting a center of the fan 55 and parallel with the long side 513, and the arrangement may be symmetrical with respect to a second axis intersecting a center of the fan 55 and parallel with the short side 512. However, the arrangement may not necessarily have four-fold symmetry. For example, as shown in FIG. 29, two adjacent supply ducts 56 extending toward a same short side 512 may be closer to each other than two adjacent supply ducts 56 extending toward opposite short sides 512. As such, the four discharge ports of the fan 55 may not all necessarily be spaced apart by equal intervals; rather two discharge ports of the fan 55 may be spaced apart by a first angle to at least partially face one short side 512, two discharge ports of the fan 55 may be spaced apart by the first angle to at least partially face the opposite short side 512, but an angle between two discharge ports of the fan 55 that are directed toward opposite short sides 512 may be greater than the first angle.

A damper 561 may be provided inside each of the plurality of supply ducts 56 to independently adjust an amount of air discharged from the four supply ducts 56. By adjusting an opening degree of the damper 561 via a main controller of the bed, ambient air may be intensively supplied to a specific or selected area of the topper 12. For example, when water is spilled or sweat is permeated at a certain point or region, and the humidity or moisture is higher than that of another point or region, the opening degree of the damper 561 may be adjusted so that ambient air is intensively supplied to the point or region with high humidity.

A plurality of discharge ports or outlets may be formed on the upper surface of the supply duct 56. The discharge ports 571 of the discharge ducts 57 may be formed through the discharge ducts 57 to serve as an inlet, and the discharge ports 571 may be provided above or align with the discharge ports of the supply ducts 56 so as to receive air discharged from the supply ducts 56. The discharge ducts 57 may have an opened top, and the discharge port 571 may be formed through a bottom surface. Side walls of the discharge ducts 57 that define the opened top may be coupled to the discharge holes 511a of the set support 51. Alternatively, the discharge duct 57 may not have an opened top, the discharge duct 57 may be formed in an upper surface exposed through the discharge hole 511a, and an inlet may be formed at a bottom surface that aligns with the discharge port of the supply duct 56.

The plurality of discharge ducts 57 may be provided at predetermined intervals along a longitudinal direction of the set support 51. The discharge hole 511a may be aligned with the guide hole 111 formed on the bottom surface of the bed cover 11 when the mattress set MS is placed on the set support 51. Air discharged from the discharge duct 57 may be supplied to the mattress set MS through the guide hole 111.

Figure 32:
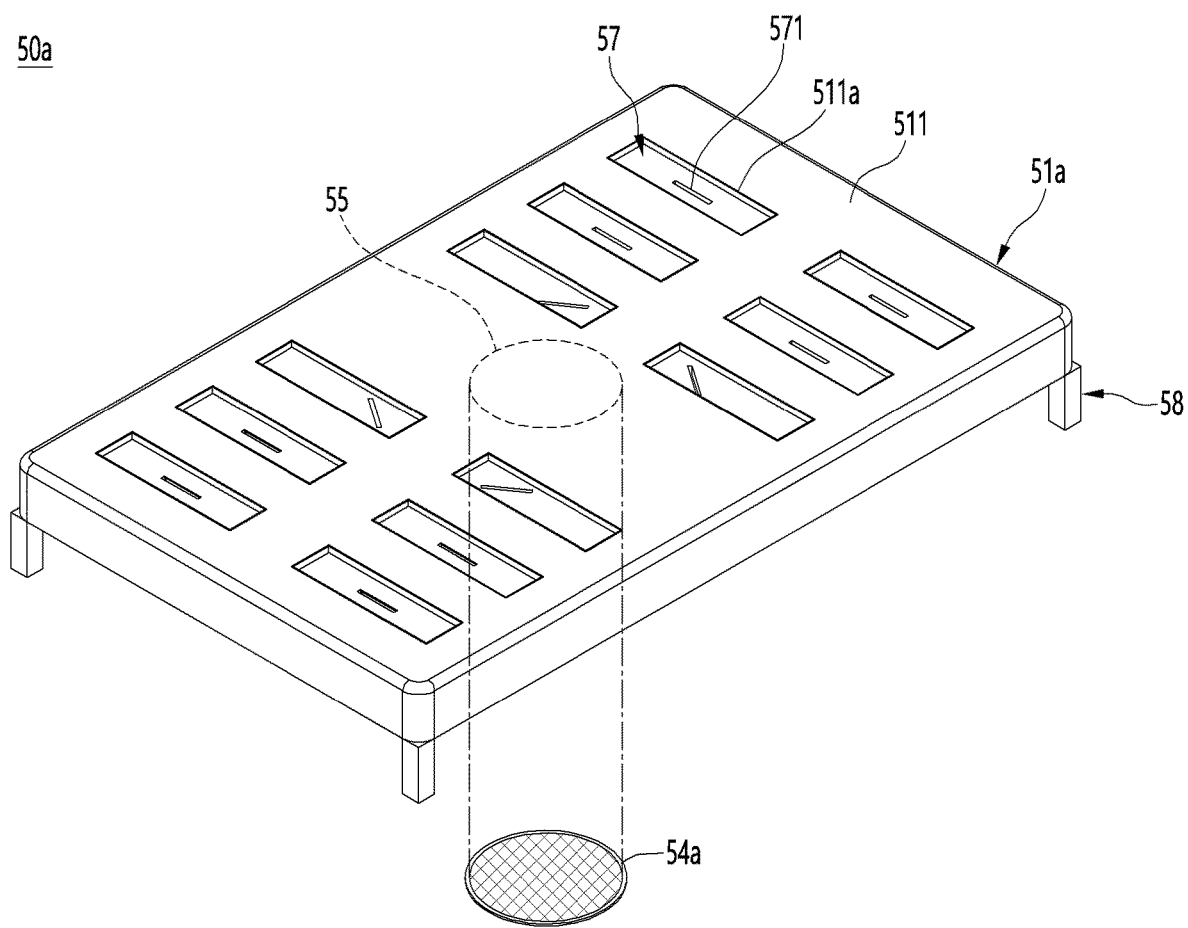
FIG. 32 is a perspective view of a drying module according to another embodiment.

Referring to FIG. 32, a drying module 50a according to another embodiment may have a same or similar structure as the drying module 50 described with reference to FIGS. 28-31 except that the drying module 50a may include legs 58 and omit the suction duct 53. The legs 58 may space the drying module 50a apart from the installation surface, and so a flow of air may freely reach an inlet of the fan 55.

The legs 58 may extend downward from an edge of the set support 51 at or near each corner so that the bottom of the set support 51 may be spaced apart from the installation surface. Ambient air under the set support 51 may be easily introduced into the fan 55, and the suction duct 53 may not be required. A filter 54a may be mounted at the inlet of the fan 55 to filter out foreign substances contained in the ambient air.

As the suction duct 53 may be omitted, an inlet recess 513a may also be omitted. As the filter 54a may be mounted on a bottom of the fan 55, a shape of the filter 54a may be different from a shape of the filter 54 previously described. For example, the filter 54 described with reference to FIGS. 28-31 may have a shape configured to fit within the inlet recess 513a and/or the suction port 531 of the supply duct 53, which may be rectangular or slot-like, while the filter 54a may have a shape corresponding to the inlet of the fan 55, which may be circular. Embodiments disclosed herein are not limited to an implementation or shape of the filter 54, 54a.

Figure 33:
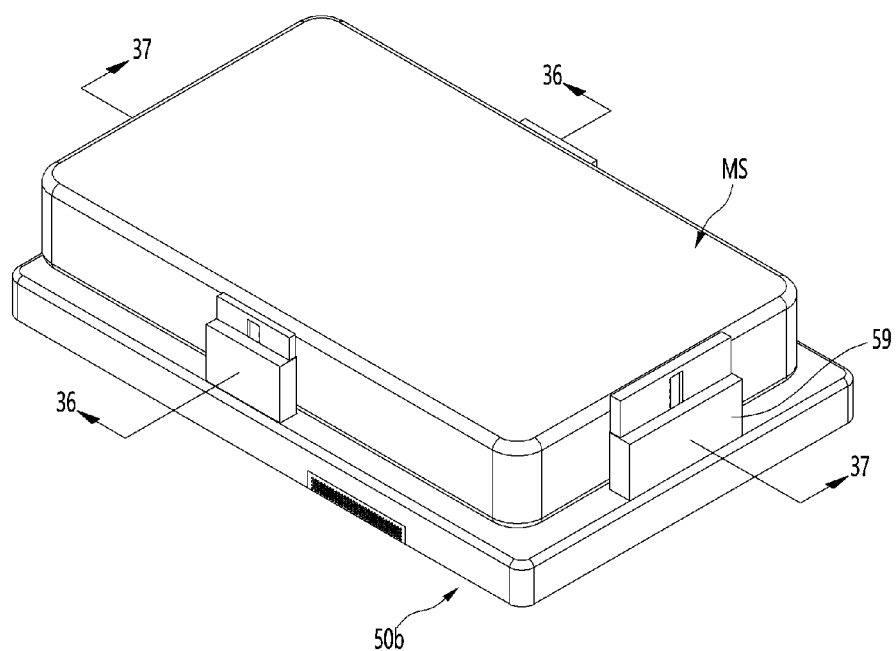
FIG. 33 is a perspective view of a bed according to a another embodiment.
Figure 34:
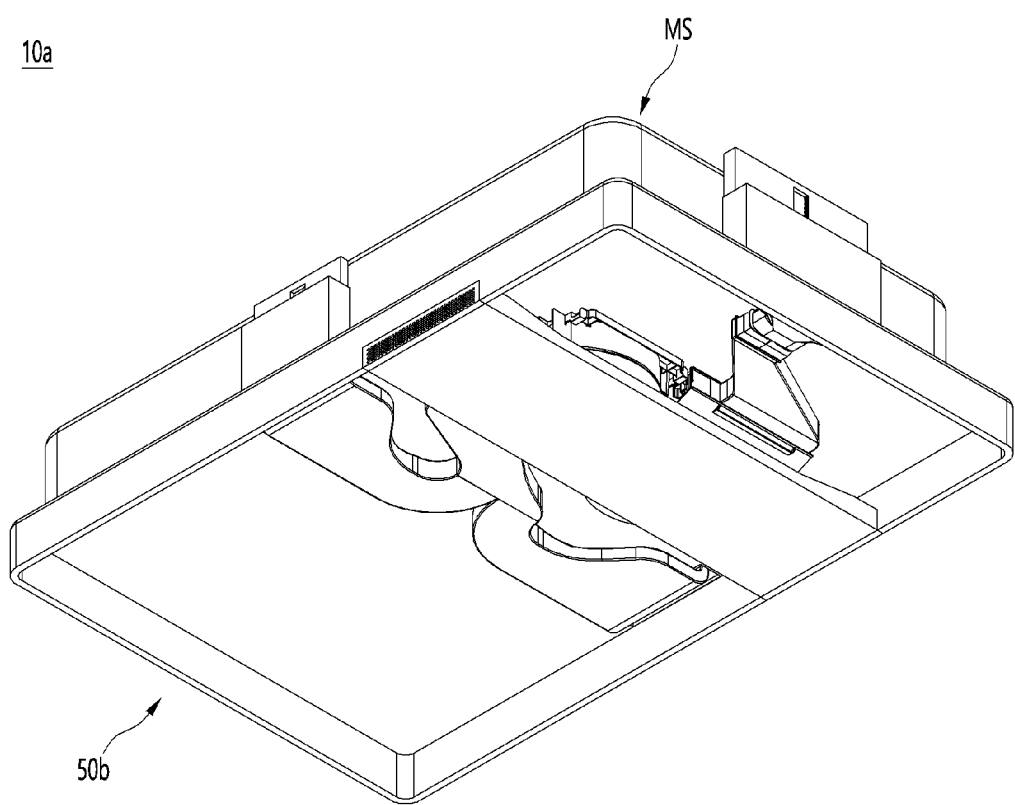
FIG. 34 is a bottom perspective view of a bed according to another embodiment.

Referring to FIGS. 33 and 34, a bed 10a and a drying module 50b according to another embodiment may be arranged such that air is discharged to sides of the mattress set MS instead of to a bottom surface. When an additional blanket, cushion, mattress topper, futon, sleeping pad, sleeping bag, etc. is placed on the mattress set MS, air discharged from the drying module 50b may flow into a space between such blanket or additional cushion and the mattress set MS to dry both.

The mattress set MS may have a same configuration of the mattress set MS previously described with reference to FIGS. 1-32, except that a guide hole may not be formed in the bed cover 11. Instead, air dispensers 59 described later may be provided to discharge air to an area outside of the mattress set MS. A redundant description is omitted.

Figure 35:
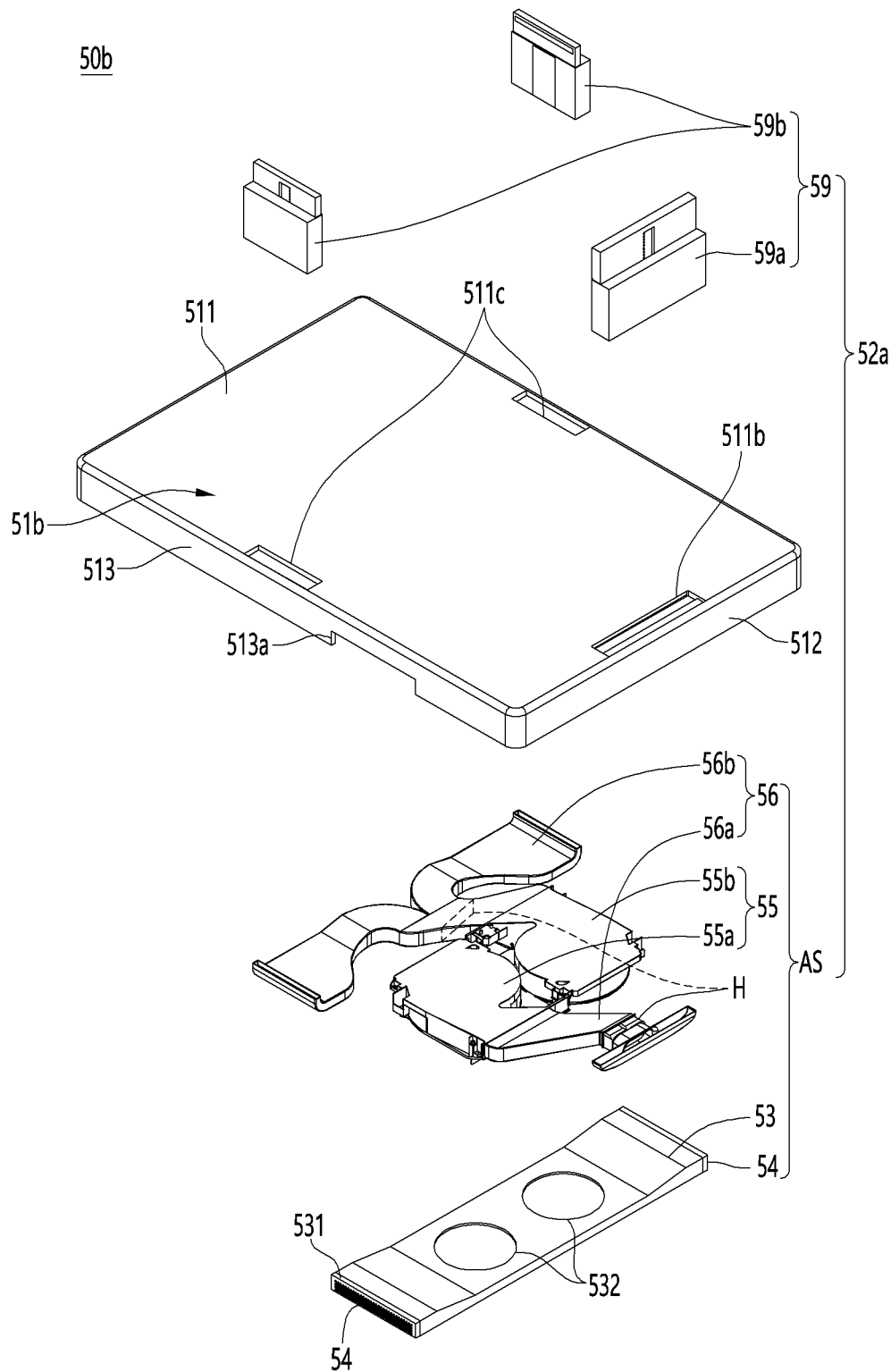
FIG. 35 is an exploded perspective view of a bed according to another embodiment.
Figure 36:
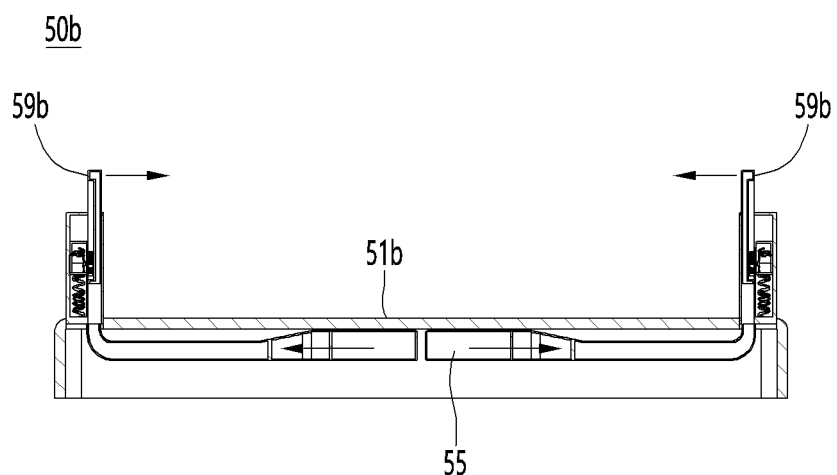
FIG. 36 is a longitudinal cross-sectional view of a drying module constituting a bed according to another embodiment taken along 36-36 of FIG. 33.
Figure 37:
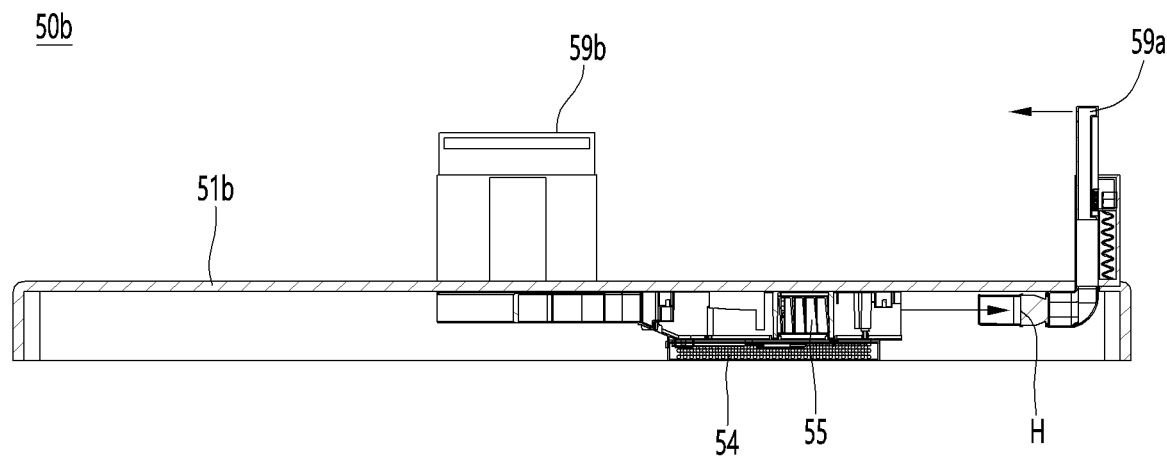
FIG. 37 is a longitudinal cross-sectional view of a drying module constituting a bed according to another embodiment taken along 37-37 of FIG. 33.

Referring to FIG. 35, the drying module 50b may include a set support 51b on which a mattress set MS is placed and a fan or blowing device 52a mounted at the set support 51b. The drying module 50b may not include discharge ducts 57.

The blowing device 52a may include a blower assembly AS mounted on a bottom surface of the set support 51b, and an air dispenser 59 mounted on an upper edge of the set support 51b. The air dispenser 59 may include a main air dispenser 59a and at least one sub or auxiliary air dispenser 59b. The main air dispenser 59a may be mounted at an upper surface of the short side 512 of the set support 51b provided at the foot of the bed, and a pair of sub air dispensers 59b may be mounted at an upper surface of the long sides of the set support 51b.

The blower assembly AS may include a suction duct 53, a filter 54 provided at a suction port 531 of the suction duct 53, a fan 55, a supply duct 56, and a heater H. The fan 55 may include a main fan 55a and at least one sub fan 55b, all of which may be or include a centrifugal fan.

The supply duct 56 may include a main supply duct 56a and a sub supply duct 56b. An inlet of the main supply duct 56a may be connected to a discharge port or outlet of the main fan 55a, and an inlet of the sub supply duct 56b may be connected to a discharge port or outlet of the sub fan 55b.

Fan mounting holes 532 may be formed in the upper surface of the suction duct 53 to communicate with the inlets of the main fan 55a and the sub fan 55b. A number of mounting holes 531 may equal a total number of sub fans 55b and the main fan 55a. As shown in the Figures, there may be one main fan 55a and one sub fan 55b, and two fan mounting holes 532. Like the embodiment described with reference to FIGS. 1-32, filters 54 may be provided at both inlets of the suction duct 53, and inlet recesses 513a may be formed in both long sides 513 of the set support 51.

The sub supply duct 56b may have left and right extensions extending toward left and right sides of the set support 51b. The sub supply duct 56b may have a main extension extending a predetermined length from the outlet of the sub-fan 55b, and the main extension may be divided into the left and right extensions extending toward the long sides 513 of the set support 51b.

Heaters H may be provided or installed inside an end of the main supply duct 56a and inside the main extension of the sub supply duct 56 at a position adjacent to where the main extension branches off into the left and right extensions. Hot air may be supplied to areas where a humidity of the bed cover 11 or the topper 12 is high so that the bed cover 11 or the topper 12 may be dried. The heater H may have various implementations. For example, the heater H may generate heat by providing current to a coil-shaped resistor, or may alternatively include a thermoelectric cooler (TEC) or Peltier device to provide hot or cold air. Embodiments disclosed herein are not limited to an implementation of the heater H.

The set support 51b may include an upper surface 511 and long and short sides 513 and 512. The suction duct 53 may extend in a width direction of the upper surface 511 to be parallel with the short sides 512 and extend between the long sides 513. The inlet recess 513a may be formed in the long sides 513, and the filter 54 may be positioned in the inlet recess 513a and/or an end of the suction port 531 of the suction duct 53.

A main discharge hole 511b may be formed at an edge of the foot of the upper surface 511 to align with the main air dispenser 59a described later, and a sub discharge hole 511c may be formed at edges of the long sides 513 to align with the sub air dispenser 59b described later. The main air dispenser 59a may be coupled to or exposed through the main discharge hole 511b, and the sub air dispenser 59b may be coupled to or exposed through the sub discharge hole 511c.

When the fan 55 operates, ambient air may be suctioned through at least one filter 54 (depending on an installation position of the bed 10 or 10a with respect to a bedroom layout) and into the suction duct 53 to flow into the fan 55. The air suctioned into the main fan 55a may flow along the main supply duct 56a to be discharged to an upper surface of the mattress set MS through the main air dispenser 59a. Air suctioned by the sub fan 55b may flow along the sub supply duct 56b, and a flow of air suctioned into the sub fan 55b may be split into left and right flows via the left and right extensions of the sub supply duct 56b to be discharged to the upper side of the mattress set MS through the sub-air dispensers 59b.

When the heater H is turned on, the air flowing along the main supply duct 56a may absorb heat from the heater H, and air discharged through the main air dispenser 59a may have an increased temperature. Similarly, air flowing along the sub-supply duct 56b may be warmed or heated by the heater H before being discharged through the sub-air dispenser 59b.

Hereinafter, a configuration and operation of the air dispenser 59 will be described in detail. The main air dispenser 59a and the sub air dispenser 59b may differ in size, but have a same or similar configuration and operation.

Figure 38:
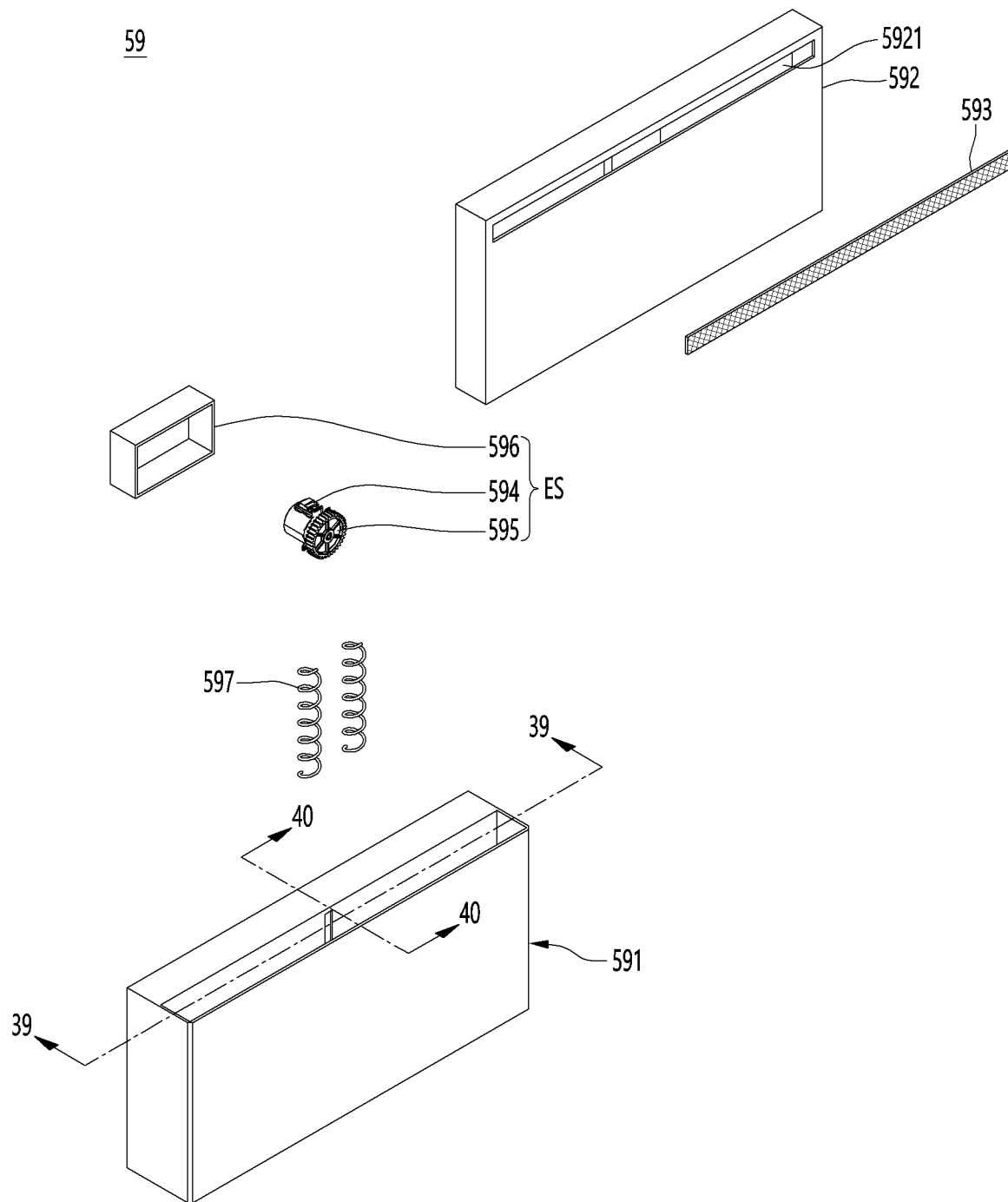
FIG. 38 is an exploded perspective view of an air dispenser constituting a drying module for a bed according to another embodiment.

Referring to FIG. 38, the air dispenser 59 may include a dispenser housing or case 591 defining an interior space and a moving or rising duct 592 configured to rise and descend in a vertical direction. The moving duct 592 may alternatively be referred to as a pop-up duct. A discharge grill 593 may be provided in a grill mounting hole 5921 formed in a front upper surface of the moving duct 592. A lift or elevator (ES) may be configured to raise and/or lower the moving duct 592, and at least one buffer spring 597 may elastically support the lift ES.

The lift ES may use a rack and pinion scheme, but embodiments disclosed herein are not limited (for example, the lift ES may alternatively include a linear actuator or plunger). The lift ES may include an elevating motor 594 to generate a rotational force, an elevating pinion 595 coupled to a rotating shaft of the elevating motor 594, and a motor housing 596 in which the elevating motor 594 is provided. The elevating pinion 585 may engage with a rack 5923 formed in the moving duct 592 (FIG. 42) and described later. The motor housing 596 may be placed on an upper end of the buffer spring 597. As shown in FIG. 38, there may be two buffer springs 597 provided adjacent to each other to support a bottom of the motor housing 596.

Figure 39:
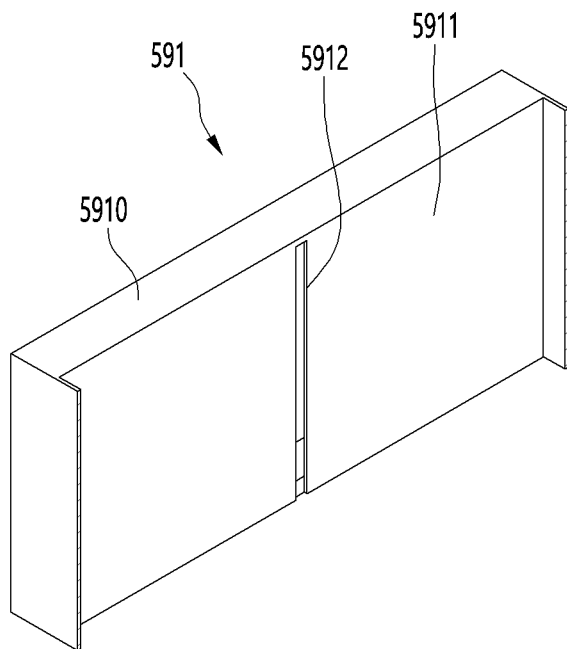
FIG. 39 is a perspective view of a dispenser housing taken along 39-39 of FIG. 38.
Figure 40:
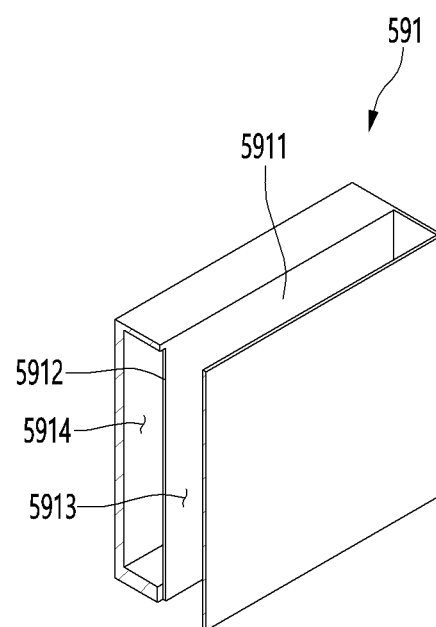
FIG. 40 is a perspective view of the dispenser housing taken along 40-40 of FIG. 38.

Referring to FIGS. 39 and 40, the dispenser housing 591 may include a main body 5910 having a hexahedral shape and a partition wall 5911 dividing the interior space of the dispenser housing 591 into first and second spaces 5913 and 5914. The main body 5910 may have a predetermined width, height, and thickness. The first space 5913 may receive the moving duct 592 and be adjacent to a side of the mattress set MS. The second space 5914 may receive the elevating motor 594 and be provided at a rear side of the first space 5913.

A guide slit 5912 may be vertically formed at a center of the partition wall 5911 to have a predetermined width and length. The width of the guide slit 5912 may correspond to an outer diameter of the rotation shaft of the elevating motor 594. The rotation shaft of the elevating motor 594 may pass through the guide slit 5912 and move up and down within the guide slit 5912 when the lift ES moves in the vertical direction.

The buffer spring 597 may be received in the second space 5914. The buffer spring 597 may be a coil spring, but embodiments disclosed herein are not limited. The motor housing 597 may be coupled to an upper end of two adjacent buffer springs 597, and the motor housing 597 may move up and down according to an expansion and contraction of the buffer spring 597.

A front bottom surface of the main body 5910 may be opened so that the first space 5913 may communicate with the discharge holes 511*b* and 511*c* formed at the edge of the upper surface 511 of the set support 51*b*. A front top surface of the main body 5910 may also be opened so that the moving duct 592 may partially slide into and out of the first space 5913 in a vertical direction.

Figure 41:
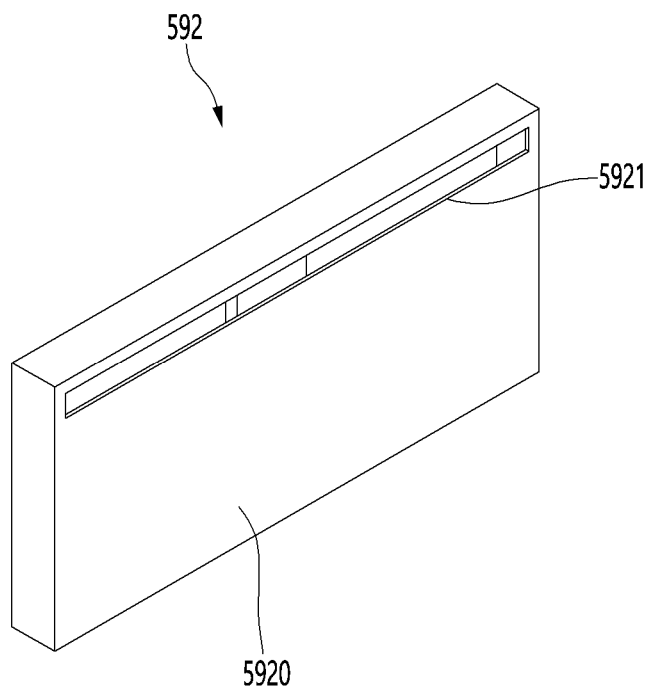
FIG. 41 is a front perspective view of a moving duct constituting an air dispenser according to an embodiment.
Figure 42:
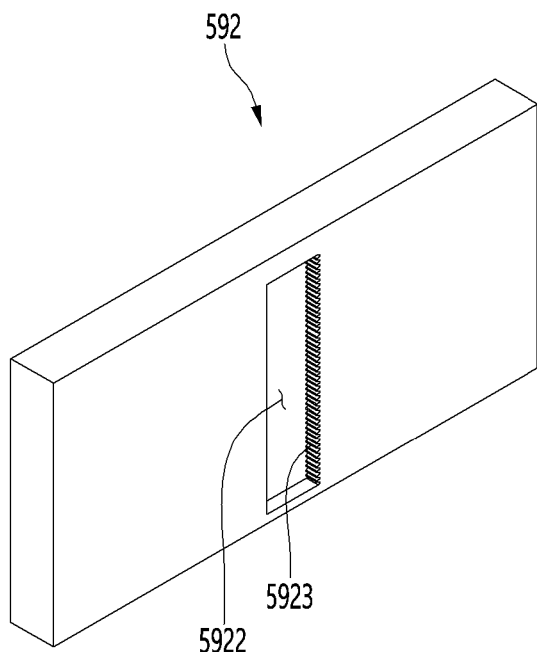
FIG. 42 is a rear perspective view of the moving duct.

Referring to FIGS. 41 and 42, the moving duct 592 may have a duct body 5920 having a hexahedral shape and the grill mounting hole 5921 formed in a front upper surface of the duct body 5920. A pinion receiving groove 5922 recessed forward may extend in a vertical direction at a center of a rear surface of the duct body 5920, and a rack 5923 may be formed at a side surface of the pinion receiving groove 5922.

The rack 5923 may include a plurality of teeth configured to engage with a plurality of teeth of the elevating pinion 595. The elevating pinion 595 may be provided in the first space 5913 while the elevating housing 596 and elevating motor 594 is provided in the second space 5914 with the rotation shaft connecting the elevating motor 594 and the elevating pinion 595 penetrating the guide slit 5912. The elevating pinion 595 in the first space 5913 of the duct housing 591 may be provided within the pinion receiving groove 5922 of the moving duct 592 to be engaged with the rack 5923. As the elevating pinion 595 rotates, the moving duct 592 may move up and down within the first space 5913.

Figure 43:
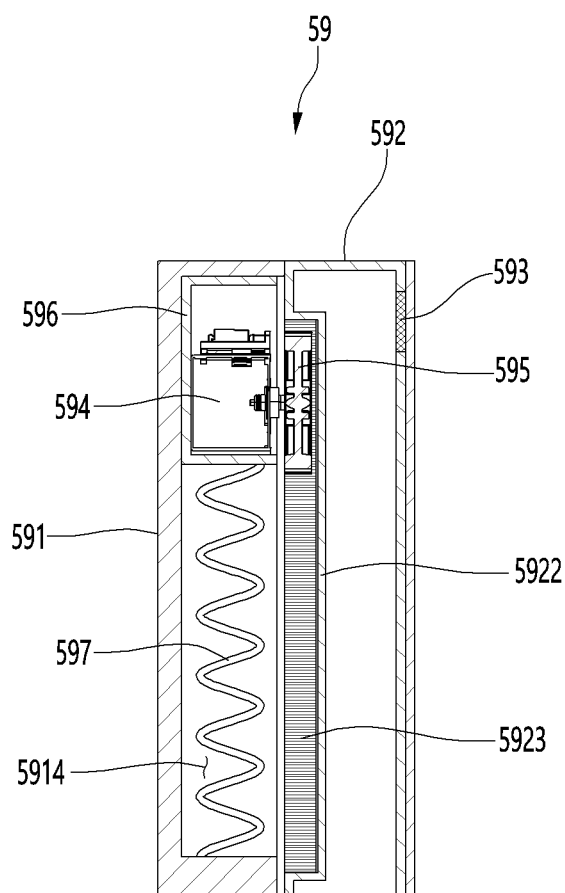
FIG. 43 is a side cross-sectional view of the air dispenser when the drying module is not operated.
Figure 44:
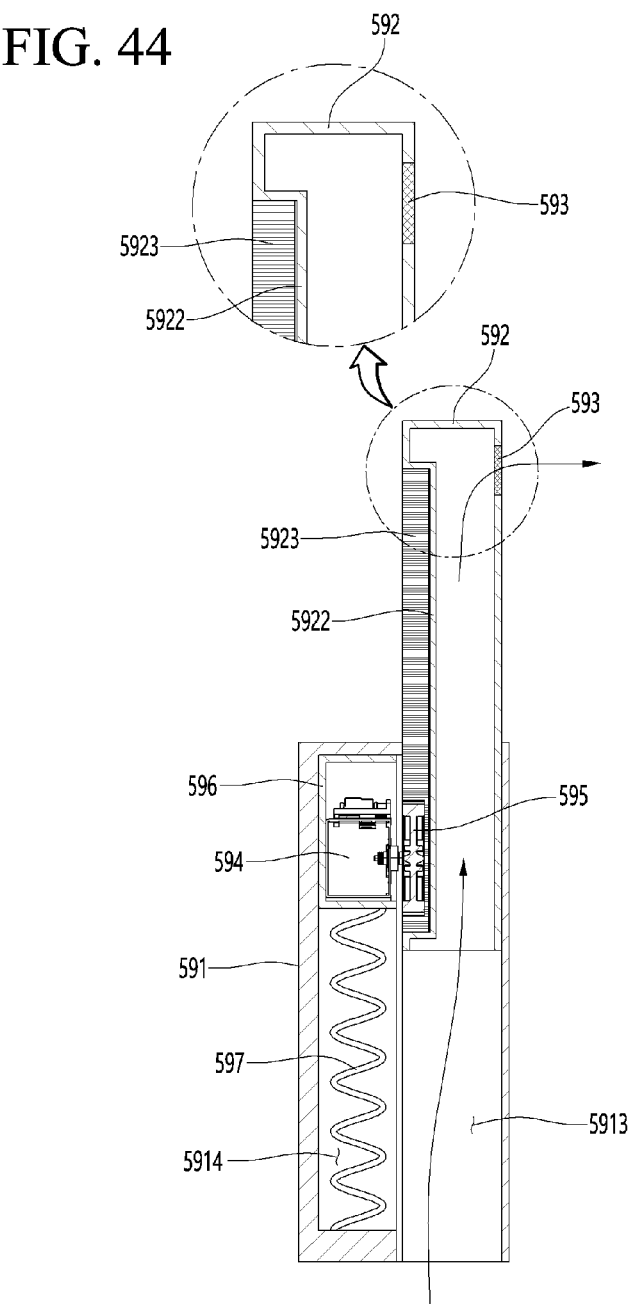
FIG. 44 is a side cross-sectional view of the air dispenser in a state in which the moving duct is raised by operating the drying module.

Referring to FIG. 43, when the drying module 50*b* is not operated, the moving duct 592 may be completely within the first space 5913 of the dispenser housing 591 so as not to be exposed Referring to FIG. 44, when the drying module 50*b* is operated, the fan 55 may be operated, and the heater H may optionally be operated. The elevating motor 594 may be operated so that the moving duct 592 rises to a maximum height, which may be determined by a length of the guide slit 5912.

When the moving duct 592 rises to the maximum height, an upper surface of the moving duct 592 may be positioned higher than the upper surface of the mattress set MS. Ambient air discharged through the discharge grill 593 may collide with the upper surface of the mattress set MS and be diffused.

Figure 45:
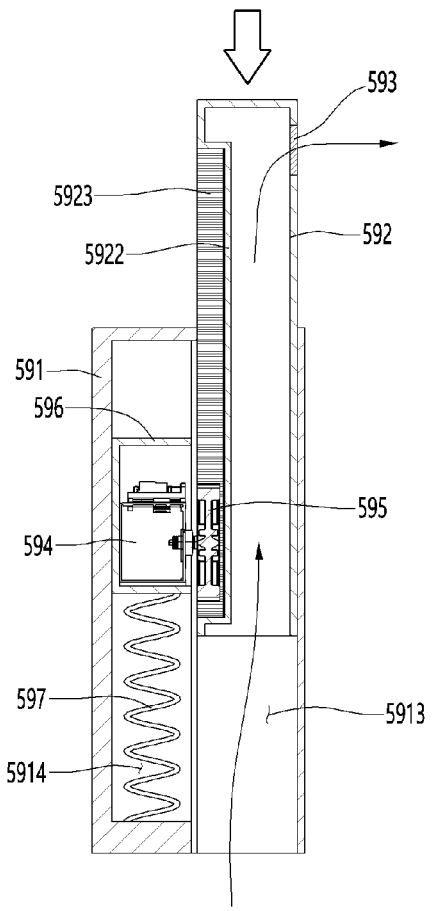
FIG. 45 is a side cross-sectional view of the air dispenser in a state in which the moving duct is lowered by an external force acting on the moving duct.
Figure 46:
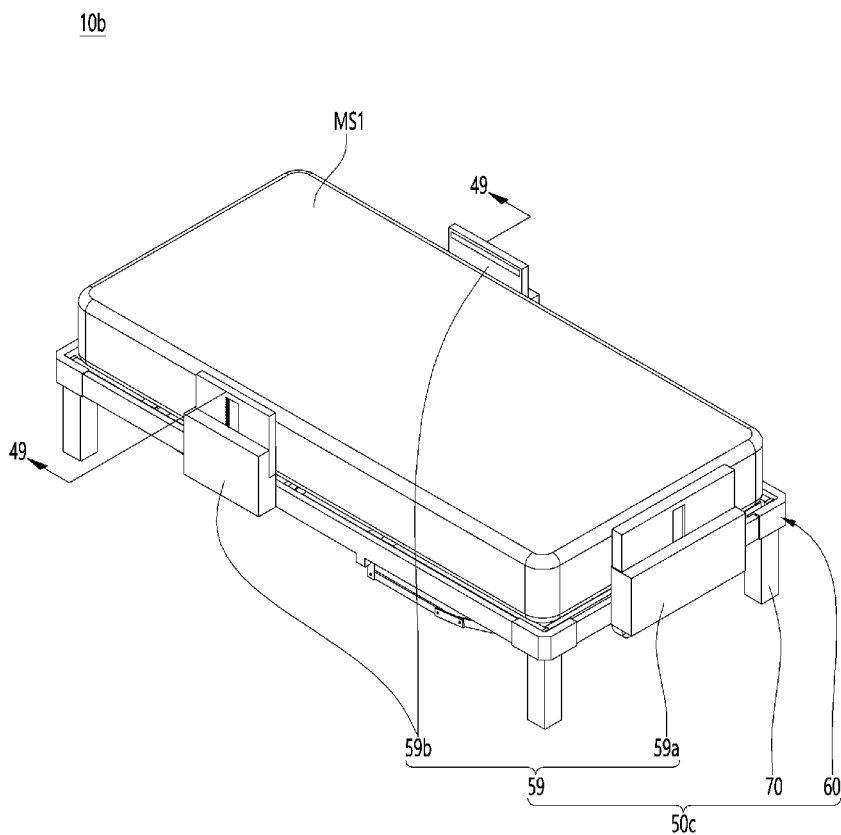
FIG. 46 is a perspective view of a bed according to another embodiment.
Figure 47:
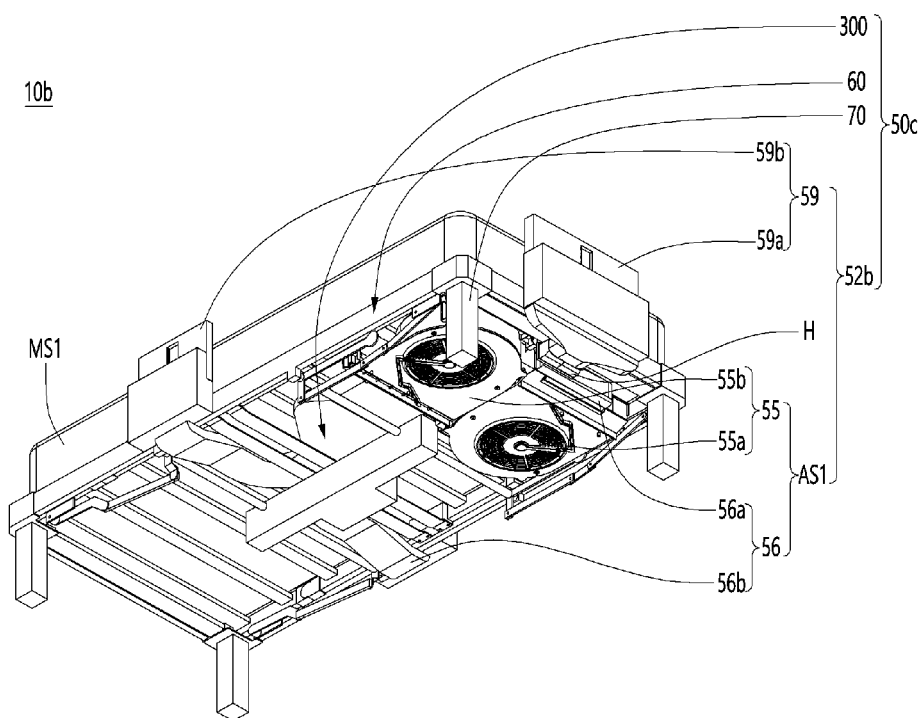
FIG. 47 is a bottom perspective view of a bed according to another embodiment.
Figure 48:
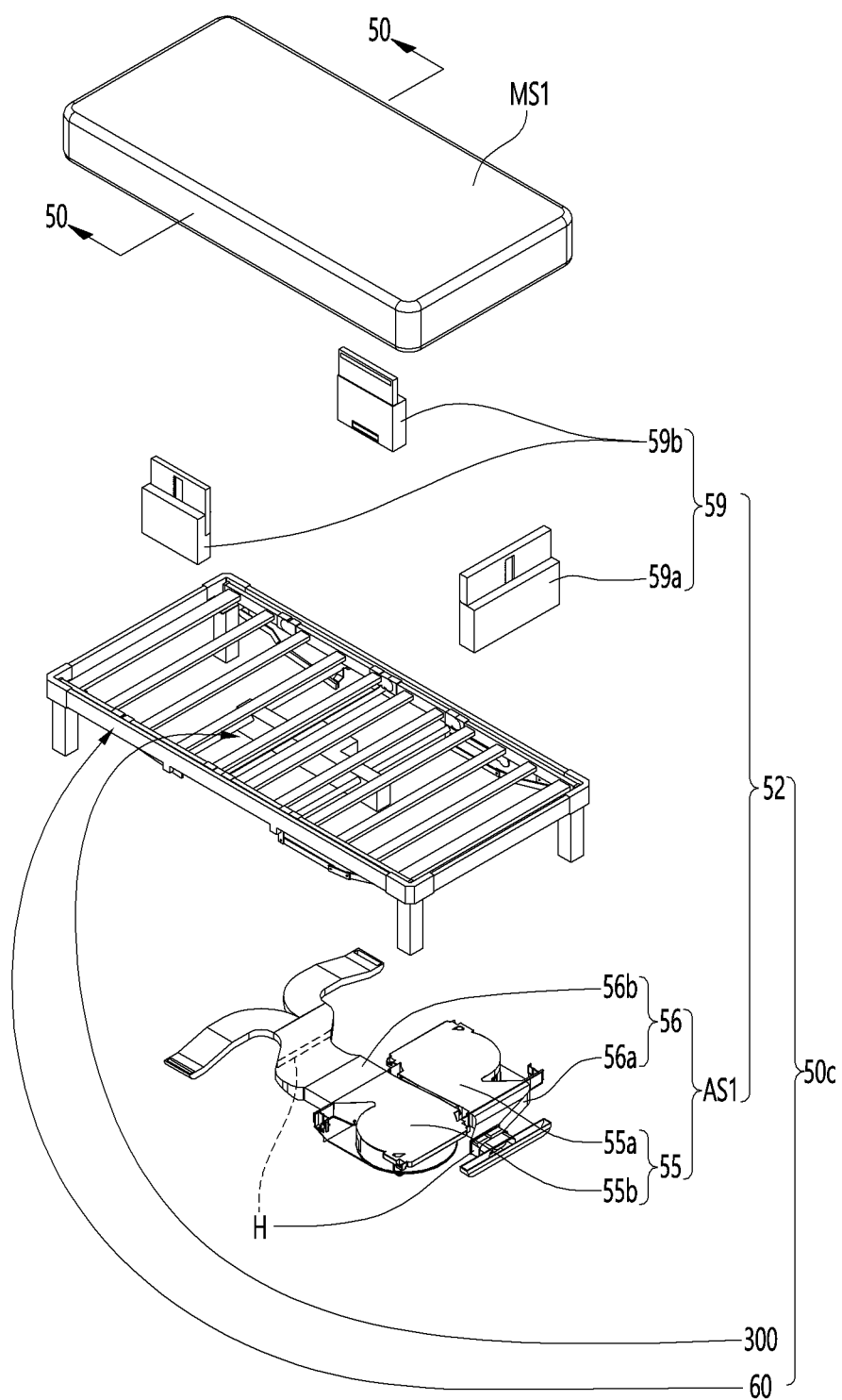
FIG. 48 is an exploded perspective view of a bed according to another embodiment.

Referring to FIG. 45, when the moving duct 592 is raised, a vertical load may be inadvertently applied to the upper surface of the moving duct 592 (e.g., due to a user's carelessness or a child's curiosity). When such a downward force is applied, the moving duct 592 may descend, and the elevating motor 594 may be forcibly rotated in reverse, which may cause damage or impede performance. However, as the motor housing 596, the elevating motor 594, the rotation shaft of the elevating motor 594, and the elevating pinion 595 may descend together with the moving duct 591, the buffer spring 597 may be contracted and partially resist the downward force to lessen an extent of damage. When the vertical load acting on the moving duct 592 is removed, the lift ES may be raised back to an original position by a restoring force of the buffer spring 597. A spring constant or stiffness of the buffer spring 597 may be configured such that the restoring force may be large enough to raise the motor housing 596, the elevating motor 594, the rotation shaft, the elevating pinion 595, and the moving duct 591.

Referring back to FIGS. 33-44, the drying module 50*b* may not include a discharge duct 57. An end of the supply duct 56 may be curved upward (see FIG. 35) to define an upper opening, which may be an outlet or discharge port of the supply duct 56. A bottom of the duct body 5920 of the moving duct 592 may have an opening aligning with the outlet of the supply duct 56 so as to receive air discharged from the supply duct 56.

Referring to FIGS. 46 to 49, a bed 10*b* according to an embodiment may include a mattress set MS1 and a drying module 50*c* provided below the mattress set MS1. A bedframe 300 may be configured to adjust an orientation or position by tilting at least a portion of the mattress set MS1 placed on an upper surface of the bedframe 300. A guard frame 60 may be coupled to the bedframe 300, and a blower device 52*b* may be installed at a bottom of the guard frame 60 and/or a bottom of the bedframe 300 to discharge ambient air to the mattress set MS1.

The guard frame 60 may further include legs 70 extending from four corners of the guard frame 60 to space the drying module 50*c* apart from the installation surface. The drying module 50*c* may be similar to the drying module 50*b* described with reference to FIGS. 33-45 except that the suction duct 53 may be omitted. The blower device 52*b* may include an air dispenser 59 and a blowing or fan assembly AS1. The air dispenser 59 may include a main air dispenser 59*a* and a sub air dispenser 59*b*.

The fan assembly AS1 may include a fan 55, a filter provided at an inlet of the fan 55, a supply duct 56 coupled to an outlet of the fan 55, and a heater H provided in the supply duct 56. The filter may have a similar configuration as the filter 54*a* shown in FIG. 32. As previously mentioned, unlike the blower assembly AS described in FIGS. 33-45, the fan assembly AS1 here does not require a suction duct because the fan 55 may be separated from the installation surface of the bed 10*b* by the legs 70, so ambient air may be freely suctioned into the fan 55. The fan 55 may include a main fan 55*a* and a sub fan 55*b*, and the supply duct 56 may include a main supply duct 56*a* and a sub supply duct 56*b*.

Figure 49:
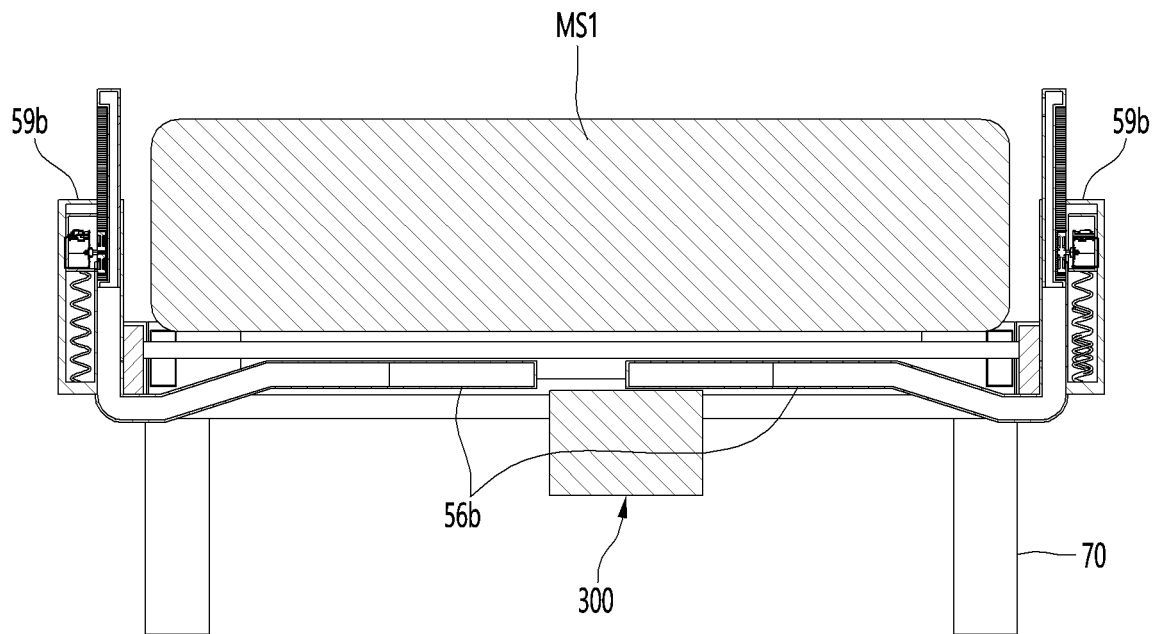
FIG. 49 is a longitudinal sectional view of a bed taken along 49-49 of FIG. 46.

As shown in FIG. 49, ambient air suctioned through the sub fan 55*b* may be supplied to the sub air dispensers 59*b* through the sub supply duct 55*b*. The air suctioned by the main fan 55*a* may be supplied to the main air dispenser 59*a* through the main supply duct 56*a*.

The filter may be mounted at the inlet of the fan 55. Since a configuration may be similar to configurations previously described, redundant descriptions may be omitted. In particular, a structure and function of the air dispenser 59 described with reference to FIGS. 38-45 applies mutatis mutandis to a description of FIGS. 46-49, though details of the bedframe 300 will be described in more detail with reference to FIGS. 51-59.

Figure 50:
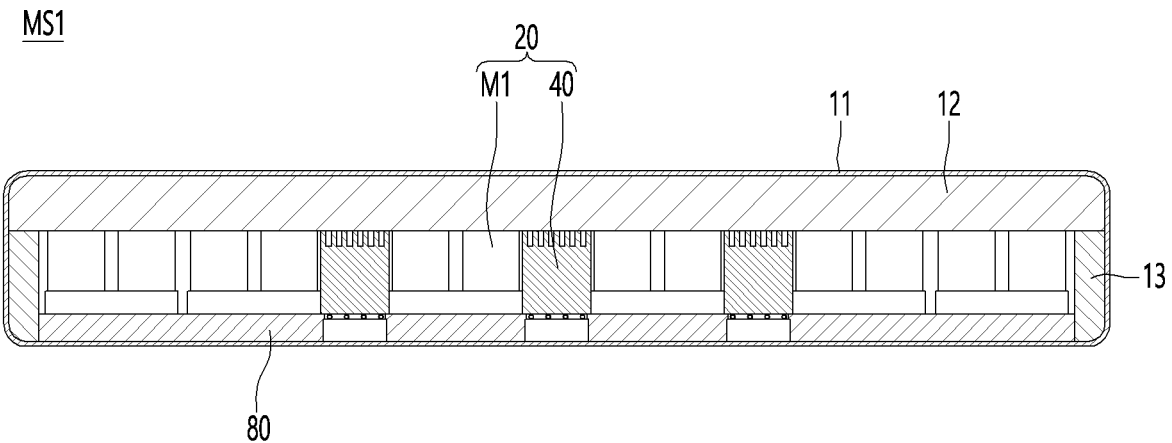
FIG. 50 is a longitudinal sectional view of a mattress set constituting a bed cut along 50-50 in FIG. 49.

Referring to FIG. 50, the mattress set MS1 may differ from the previously described mattress set MS in that the bed cover 11 does not surround the bedframe 300. Rather, the bedframe 300 may be separate from the mattress set MS, which may be separable from the bedframe 300. The mattress set MS1 may include the cushion module 20 having a plurality of firmness adjusters M1 and partitions 40 provided therebetween, the topper 12, the bed cover 11, the safety guard 13, and also a cushion seating plate 80. The cushion seating plate 80 may also be surrounded by the bed cover 11.

The safety guard 13 may surround side edges of the cushion seating plate 80. Hereinafter, a configuration and operation of the cushion seating plate 80, the guard frame 60, and the bedframe 300 will be described in detail with reference to the drawings.

Figure 51:
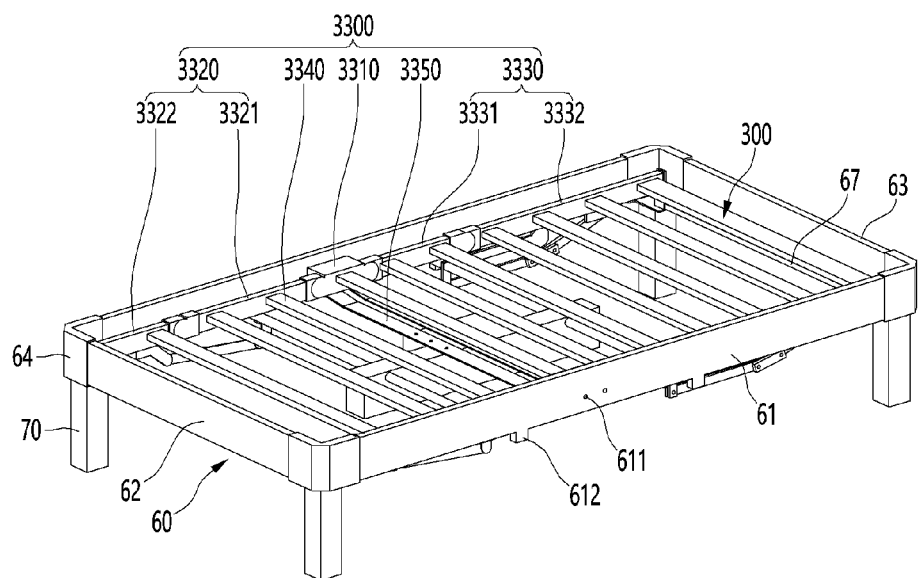
FIG. 51 is a perspective view from above of a combination of a bedframe and a guard frame constituting a drying module for a bed according to another embodiment.
Figure 52:
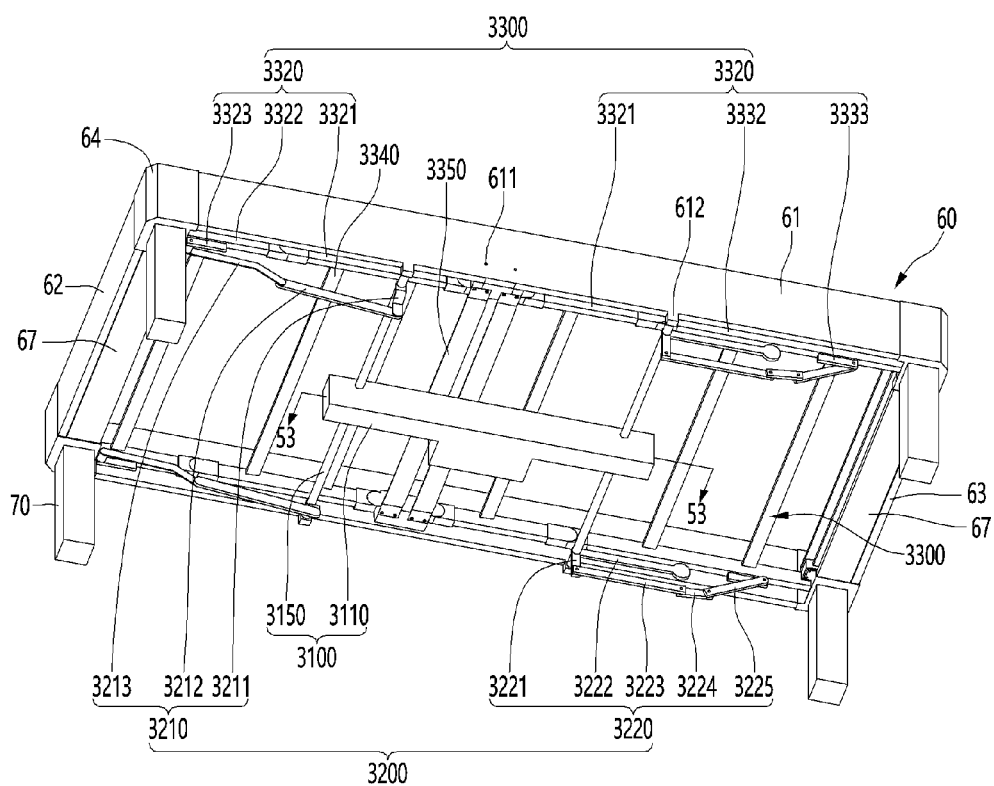
FIG. 52 is a perspective view of a combination of the bedframe and a guide frame as viewed from below.

Referring to FIGS. 51 and 52, the bedframe 300 may include a motion generator 3100, a motion link 3200, and a seating frame 3300. The seating frame 3300 may provide a surface on which the cushion module 20 is placed, and the seating frame 3300 may be bent and tilted by a driving force supplied from the motion generator 3100.

The seating frame 3300 may include a pair of fixing blocks 3310, an upper body frame 3320, a lower body frame 3330, a cushion seating plate or bar 3340, and a fixing bar 3350. The pair of fixing blocks 3310 may be fixed to inner surfaces of the pair of side frames 61 of the guard frame 60 to face each other. A fastening member (e.g., a bolt or screw) may pass through the fastening hole 611 formed in the side frame 61 and be inserted into the fixing block 3310. The pair of fixing blocks 3310 may be located at a center of the side plate 61, but embodiments disclosed herein are not limited. A rear end of the upper body frame 3320 and a front end of the lower body frame 3330 may be rotatably coupled to the fixing block 3310.

The upper body frame 3320 may include a pair of rear frames 3321, each of which has a rear end rotatably coupled to the fixing block 3310, and a pair of front frames 3322 rotatably coupled to the front ends of the rear frames 3321, respectively. Each of the pair of rear frames 3321 and the pair of front frames 3322 may be parallel to each other.

The lower body frame 3330, like the upper body frame 3320, may have a pair of front frames 3331 rotatably coupled to the pair of fixed blocks 3310 and a pair of rear frames 3332 rotatably coupled to rear ends of the front frames 3331, respectively. The cushion seating plate 3340 may connect frames among the front and rear frames 3322, 3331, 3321, and 3332 that are provided parallel to each other.

The seating frame 3300 may be defined as a structure including a plurality of parallel cushion seating plates 3340 connected to each other to resemble a slatted bed frame. With respect to the upper body frame 3320, the front frame 3322 may be or include a pair of parallel straight bars, and at least one seating plate 3340 may connect the pair of parallel straight bars of the front frame 3322. The rear frame 3321 may be or include a pair of parallel straight bars, and at least one seating plate 3340 may connect the pair of parallel straight bars of the rear frame 3321.

Similarly, with respect to the lower body frame 3330, the front frame 3331 may be or include a pair of parallel straight bars, and at least one cushion seating plate 3340 may connect the pair of parallel straight bars of the front frame 3331. The rear frame 3332 may be or include a pair of parallel straight bars, and at least one cushion seating plate 3340 may connect the pair of parallel straight bars of the rear frame 3332. A coupling between the cushion seating plates 3240 and the bars may be optionally rotatable at tilting axes. Furthermore, at least one cushion seating plate 3340 may be coupled (e.g., rotatably coupled) to the fixing block 3310.

Similar to how the seating frame 39 described with reference to FIGS. 1-11 was divided into sections that move or pivot relative to each other (upper body frame 31, the hip frame 32, the thigh frame 33, and the calf frame 34), the seating frame 3300 may be divided into sections that move or pivot relative to each other, the sections being defined by the pair of front frames 3322 of the upper body frame 3320 and the cushion seating plates 3340 therebetween, the pair of rear frames 3321 of the upper body frame 3320 and the cushion seating plates 3340 therebetween, the pair of front frames 3331 of the lower body frame 3330 and the cushion seating plates 3340 therebetween, and the pair of rear frames 3332 of the lower body frame 3330 and the cushion seating plates 3340 therebetween. The different sections that pivot relative to each other may alternatively be referred to as tilting portions.

Left and right ends of the fixing bar 3350 may connect bottom surfaces of the pair of fixing blocks 3310, respectively, so as to reduce or prevent sagging of the bedframe 300. In addition, a transmission or transmitter 3110 of the motion generator 3100 may be coupled to the fixing bar 3350. The transmitter 3110 will be described in more detail later.

An upper link connection end or front bracket 3323 may be provided on a bottom surface of the pair of front frames 3322 of the upper body frame 3320, and a lower link connection end or rear bracket 3333 may be provided on a bottom surface of the pair of rear frames 3322 of the lower body frame 3330, respectively.

The motion generator 3100 may tilt or pivot the various sections of the seating frame 3300 via the motion link 3200. The motion generator 3100 may include a transmission and a link drive shaft 3150 penetrating the transmission 3110. Both ends of the link drive shaft 3150 may connect to the link drive shaft connection end 612, respectively.

The link drive shaft 3150 may be a pair of shafts coupled to the transmission 3110. The pair of shafts of the link drive shaft 3150 may include a front shaft 3150A passing through a front end of the transmission 3110 and a rear shaft 3150B passing through a rear end of the transmission 3110.

A mounting groove or recess may be formed on an inner surface of the link driving shaft connecting end 612, and an end of the link driving shaft 3150 may be fitted into the mounting groove. Alternatively, the mounting groove may be a hole. Further, a plurality of ball bearings may be arranged on an inner circumferential surface of the mounting groove so that frictional force may be reduced when the link drive shaft 3150 rotates. Since both ends of the link drive shafts 3150 may be connected to the link drive shaft connection end 612, a load of the motion generator 3100 and the motion link 3200 may be supported by the guard frame 60.

The motion link 3200 may include a pair of front links 3210 connected to both ends of the front shaft of 3150A, and a pair of rear links 3220 connected to both ends of the rear shaft 3150B. The front link 3210 may have a two-fold link structure via a moveable link 3213 and a fixing link 3212, while the rear link 3220 may have a multi-fold link structure via an arm link 3222, a fixing link 3223, a moveable link 3225, and a connection link 3224.

The front link 3210 may include a rear bracket 3211 extending downward from the font shaft 3150A. The fixed link 3212 may extend from an end of the bracket 3211, and the movable link 3213 may be rotatably connected to a rear end of the fixing link 3212. A front end of the movable link 3213 may be connected (either fixedly or rotatably) to the front bracket 3323. The front bracket 3323 may be formed to be parallel to the front frame 3322 of the upper body frame 3320, while the rear bracket 3211 may extend downward.

Figure 56:
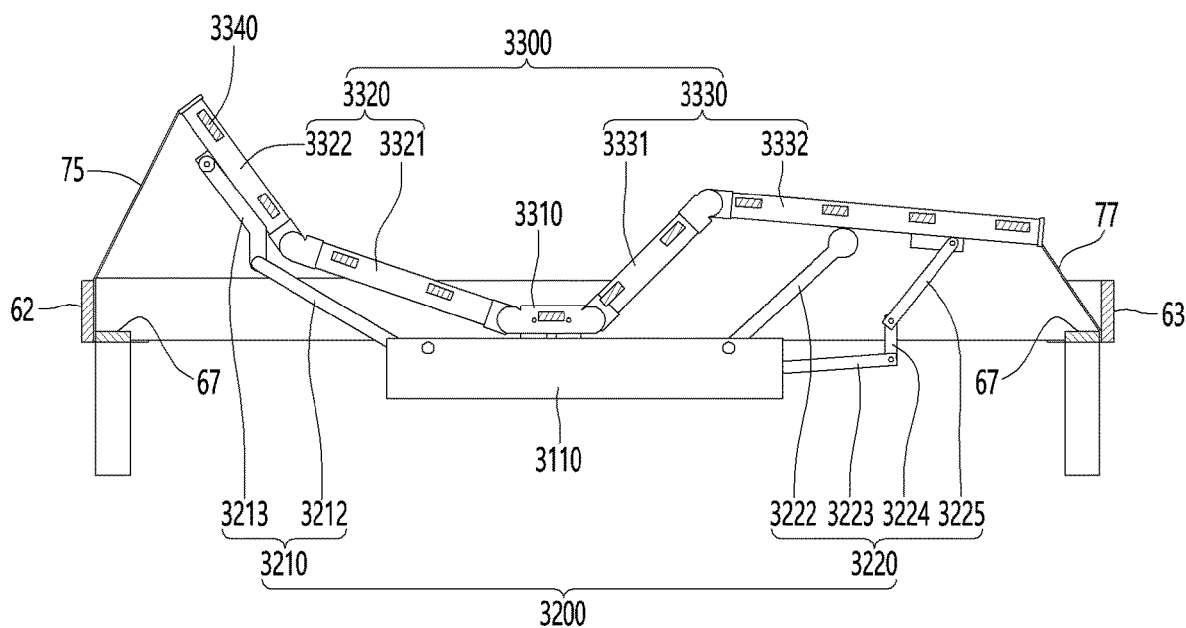
FIG. 56 is a longitudinal sectional view of the bedframe cut along 56-56 of FIG. 55.

A rear end of the fixing link 3212 may be fixed to a bottom end of the bracket 3211, and the front shaft 3150A, the bracket 3211, and the fixing link 3212 may rotate as one body. When the front shaft 3150A rotates, the bracket 3211 and fixing link 3212 may rotate with the front shaft 3150A, while the moveable link 3213 may rotate or pivot with respect to the fixing link 3212. FIG. 56 shows a state in which the front shaft 3150A has been rotated to tilt the bracket 3211 and fixing link 3212.

The rear link 3220 may include a front bracket 3221 extending downward from the rear shaft 3150B. The arm link 3222 may extend from the rear shaft 3150 in a direction perpendicular to a downward extension direction of the front bracket 3221. The fixed link 3223 may have a front end rotatably connected to a rear end of the front bracket 3221.

The connection link 3224 may have a front end rotatably connected to a rear end of the fixing link 3223. The rear end of the connection link 3224 may be rotatably connected to a front end of the movable link 3225. The front bracket 3221 and the arm link 3222 may be formed of a single member that is bent in an L-shape, but embodiments disclosed herein are not limited. The rear shaft 3150B may pass through the bracket 3221 to be fixed.

The arm link 3222 may include an arm link body horizontally extending from the rear shaft 3150B, and a circular slider may be formed at a rear end of the arm link body. A diameter of the slider may be larger than a width of the arm link body so that an upper surface of the slider of the arm link 3222 may contact the lower surface of the rear frame 3332 of the lower body frame 3330.

An upper surface of the slider may slide along a bottom surface of the rear frame 3332 while maintaining contact so that when the rear shaft 3150B rotates, the rear frame 3332 of the lower body frame 3330 may move or pivot relative to the front frame 3331 of the lower body frame 3330. The rear end of the movable link 3225 may be rotatably connected to the rear bracket 3333. The rear bracket 3333 of the rear link 3220 may have a similar structure as the front bracket 3323 of the front link 3210. The rear shaft 3150B, the front bracket 3221, and the arm link 3222 may rotate together as one body.

As previously described, the front link 3210 may have a two-fold link structure via the moveable link 3213 and the fixing link 3212, and the rear link 3220 may have a multi-fold link structure via the arm link 3222, fixing link 3223, moveable link 3225, and connection link 3224. Although the rear link 3220 is shown to be a four-fold link, embodiments disclosed herein are not limited in a number of links comprising the front and rear links 3210 and 3220.

Figure 53:
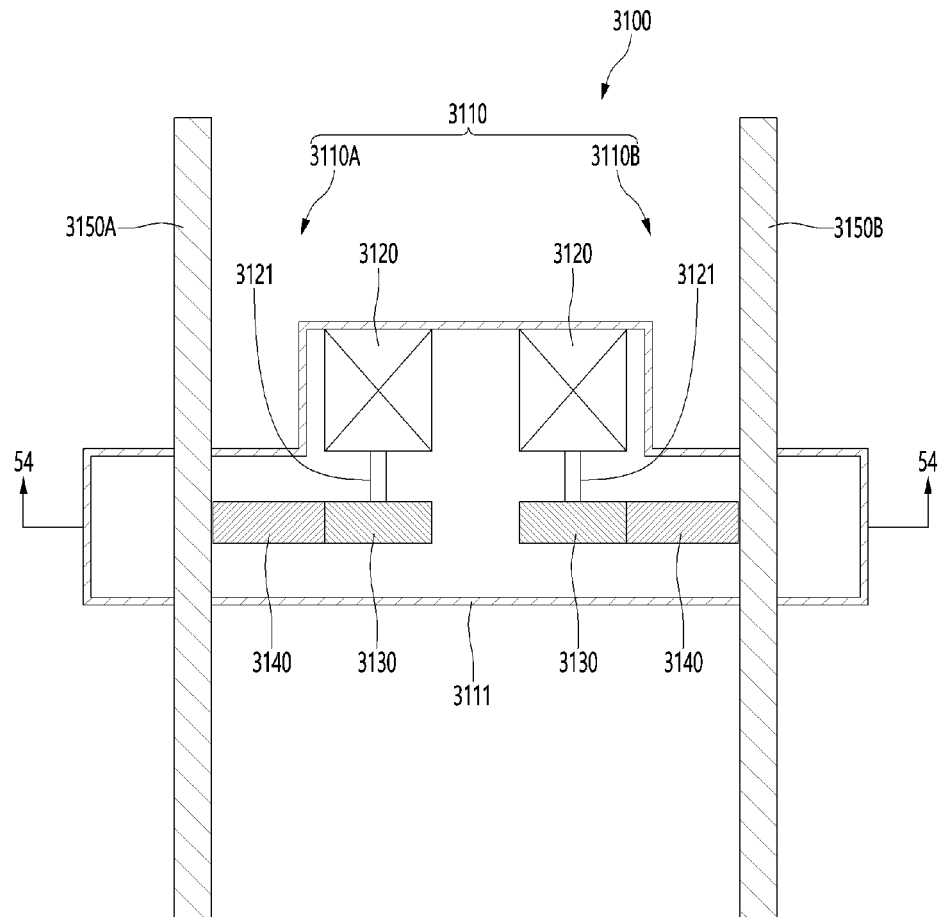
FIG. 53 is a horizontal cross-sectional view of a motion generator taken along 53-53 of FIG. 52.
Figure 54:
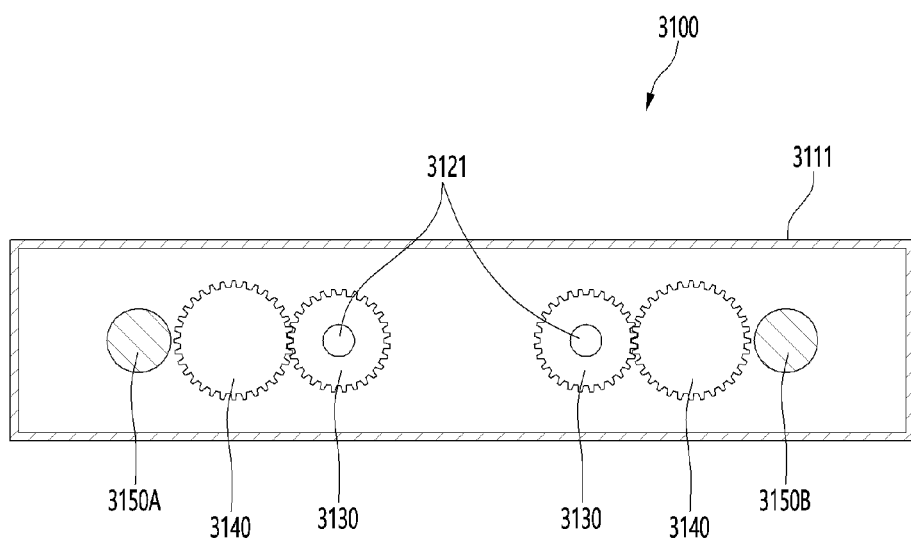
FIG. 54 is a longitudinal sectional view of the motion generator taken along 54-54 of FIG. 53.

Referring to FIGS. 53 and 54, the motion generator may generate a driving force for rotating the front and rear shafts 3150A and 3150B of the link drive shaft 3150, which may be connected to the transmission 3110.

The transmission 3110 may include a gear box or container 3111 and front and rear transmission assemblies 3110A and 3110B provided inside of the gear box 31110 and corresponding to the front and rear shafts 3150A and 3150B, respectively. Each transmission assembly 3110A, 3110B may include a motor 3120, a tilting gear 3130 connected to a rotation shaft 3121 of the motor 3120, and a reduction gear 3140 meshed with or configured to engage with the tilting gear 3130.

Each of the front and rear shafts 3150A and 3150B may penetrate the gear box 3111 and rotate while being meshed or engaged with the reduction gear 3140. The two transmission assemblies 3110A and 3110B may independently drive a rotation of the front and rear shafts 3150A and 3150B, respectively, so that the upper body frame 3320 and the lower body frame 3330 may be adjusted independently of each other.

Various types of structures may be implemented as the transmission 3110, and embodiments disclosed herein are not limited to the front and rear transmission assemblies 3110A and 3110B described. Embodiments disclose herein may include all types of transmissions 3110 in which power is generated from a gearbox 3110 and transmitted to a link drive shaft 3150.

Figure 55:
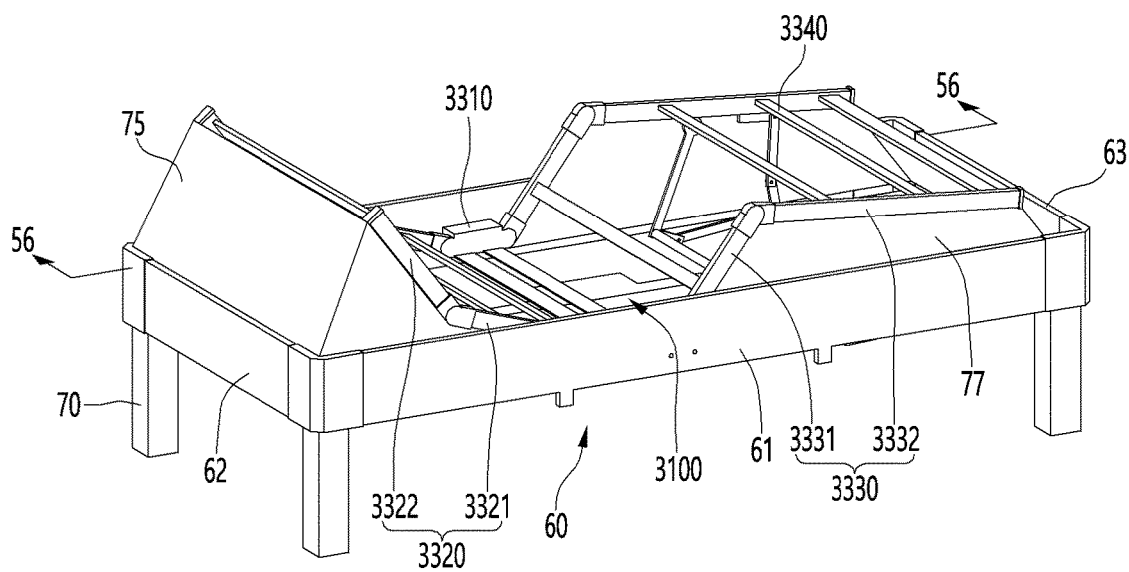
FIG. 55 is a perspective view showing an operation of a bedframe constituting a drying module for a bed according to another embodiment.

Referring to FIGS. 55 and 56, the upper body frame 3320 and the lower body frame 3330 may both be tilted or pivoted. When power is supplied to the motion generator 3100 and the motor 3120 is operated, the link driving shaft 3150 may rotate. When the front shaft 3150A rotates, the front link 3210 may rotate to tilt the upper body frame 3320 by a predetermined angle, and when the rear shaft 3150B rotates, the rear link 3220 may rotate to tilt the lower body frame 3330 by a predetermined angle.

The fixed link 3212 of the front link 3210 may be fixed to the rear bracket 3211, while an end of the movable link 3213 may maintain a connection to the front frame 3322 via the front bracket 3323. When the motor 3120 in the front transmission assembly 3110A is operated, the front shaft 3110A rotates, and the front link 3210 rotates to tilt both the front and rear frames 3322 and 3321 of the upper body frame 3320 upward by a predetermined angle.

When the motor 3120 in the rear transmission assembly 3110B is operated, the rear shaft 3110B rotates, and the front bracket 3221 and the arm link 3222 may rotate together as one body. The rear frame 3332 of the lower body frame 3320 may be lifted as the arm link 3222 rotates upward. As the arm link 3222 and the front bracket 3221 rotate, the fixed link 3223 may be pushed forward, and a rear end of the rear frame 3332 may be supported via the rear link 3333 and the moveable link 3225. In addition, the rear end of the front frame 3331 may be rotated as the lower frame 3332 rises, resulting in a state as shown in FIG. 56.

As the arm link 3222 rotates by a rotation of the rear shaft 3150B, the arm link 3222 may slide along the bottom surface of the lower frame 3322. Without the moveable link 3225 and rear bracket 3333, the rear end of the rear frame 3332 may sag downward.

As the upper body frame 3320 and/or the lower body frame 3330 are tilted, a space or gap may form between the upper body frame 3320 and the guard frame 60 and/or between the lower body frame 3330 and the guard frame 60. Foreign substances may be introduced into the bed 10a through the gap, and there is a possibility that a body part of may be caught and injured in the gap.

In order to block the occurrence of such a problem, at least one blocking film or layer 75 and/or 77 may be provided. The blocking film 75 and/or 77 may include an upper or front blocking film 75 connecting the upper body frame 3320 and the guard frame 60, and a lower or rear blocking film 77 connecting the lower body frame 3330 and the guard frame 60. The front and rear blocking films 75 and 77 may also be referred to as blocking sheets or covers.

The front and rear blocking films 75 and 77 may be formed of a soft or elastic cloth, sheet, or band, a folded or wrinkled cloth, a material having an accordion bellow or spring shape, etc. Embodiments disclosed herein are not limited to a material of the front and rear blocking films 75 and 77.

Figure 57:
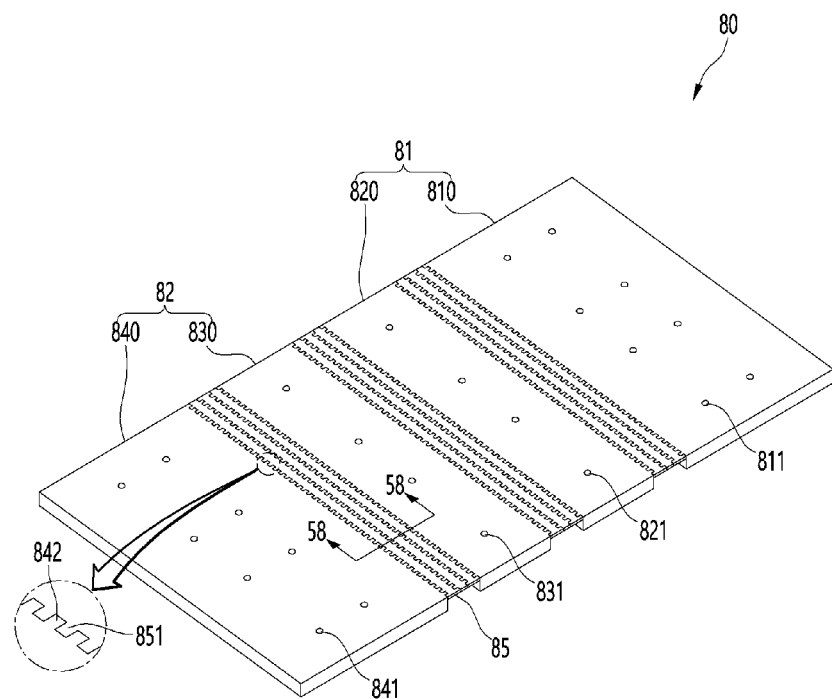
FIG. 57 is a perspective view of a seating plate constituting a mattress set for a bed according to an embodiment.
Figure 58:
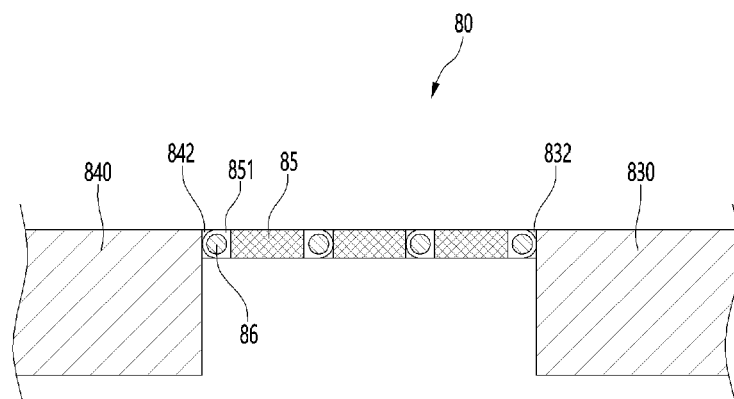
FIG. 58 is a partial longitudinal sectional view of the seating plate cut along 58-58 of FIG. 57.
Figure 59:
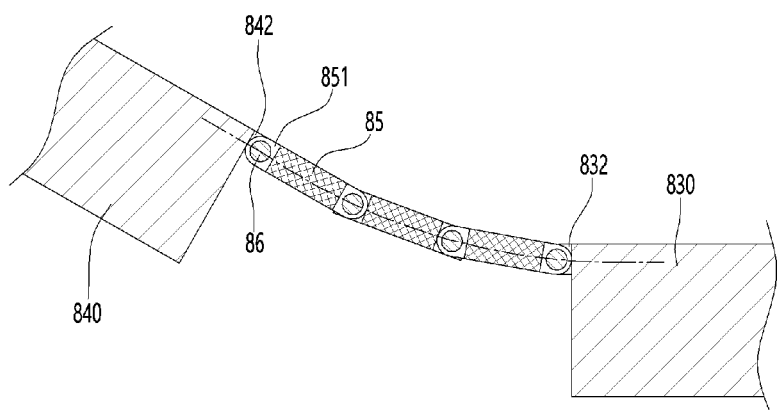
FIG. 59 is a partial longitudinal sectional view of the seating plate cut along 58-58 of FIG. 57 in a tilted state by the bedframe.

Referring to FIGS. 57 to 59, the plurality of firmness adjusters M1 may be fixed to an upper surface of the seat plate 80. The seat plate 80 may have a plate structure formed by a plurality of plates 810, 820, 830, 840 that are hinged or rotatably coupled to each other, the plurality of plates 810, 820, 830, 840 corresponding to sections of the bed frame 300 configured to be adjustable. The seat plate 80 may include an upper or front body plate 81 and a lower or rear body plate 82. The upper body plate 81 may be provided on an upper side of the upper body frame 3320, and the lower body plate 82 may be provided on an upper side of the lower body frame 3330.

The upper body plate 81 may include a front plate 810 and a rear plate 820 rotatably connected to the front plate 810. The front plate 810 may be provided on a section of the upper body frame 3320 having the front frame 3322, and the rear plate 820 may be provided on a section of the upper body frame 3320 having the rear frame 3321.

The lower body plate 82 may include a front plate 830 and a rear plate 840 rotatably connected to the front plate 830. The front plate 830 may be provided on a section of the lower body frame 3330 having the front frame 3331, and the rear plate 840 may be provided on a section of the lower body frame 3330 having the rear frame 3332.

A plurality of fastening holes 811, 821, 831 and 841 may be formed in each of the plates 810, 820, 830, and 840, respectively. When the plurality of firmness adjusters M1 are seated on the seat plate 80, a plurality of fastening members (e.g., bolts or screws) may penetrate the fastening holes 811, 821, 831, 841 and the firmness adjusters M1. As an example, a fastening boss may extend from the bottom surface of the bottom case 23 to be inserted into the fastening holes 811, 821, 831, 841, and the fastening members may be inserted into the fastening boss and holes 811, 821, 831, 841.

As shown in FIGS. 58 and 59, adjacent plates among the plates 810, 820, 830, and 840 may be connected by one or more joint plates 85 and a plurality of joint hinges 86. A plurality of extension ends or protrusions 832, 842 may protrude from each of the ends of the plates 810, 820, 830, and 840. The plurality of extension ends 832, 842 may be spaced apart from each other at a predetermined interval in a width direction of the seat plate 80. The joint plates 85 may have a plurality of extension ends 851 which extend past the joint hinge 86, and the plurality of extension ends 851 may be configured to fit within or be engaged with the plurality of extension ends 832, 842 of the plates 810, 820, 830, and 840.

The plurality of extension ends 851, 821, and 842 may have teeth that engage or mesh with each other like gears. The plurality of extensions ends 851, 832, and 842 may be formed to have a plurality of protrusions and recesses. The plurality of extensions ends 851 may fit with the plurality of extension ends 832, 842 like pieces to a puzzle, as the protrusions of the extension ends 851 may fit within the recesses formed in the extension ends 832, 842.

The joint hinge 86 may pass through the extension ends 832, 842, 851 so that two abutting plates of the plates 810, 820, 830, and 840 may rotate or pivot relative to each other. When two plates of the plates 810, 820, 830, and 840 are directly connected by the joint hinge 86, a degree of freedom of bending of the plates 810, 820, 830, and 840 may be low. A bending degree of freedom of the plates 810, 820, 830, and 840 may be defined as a radius of curvature of a curve (as shown by the dotted line in FIG. 59).

A high degree of bending freedom may correspond to a large a radius of curvature. The higher the degree of bending freedom, the smoother the plates 810, 820, 830, and 840 may appear when bent. When the joint plate 85 is provided, the degree of bending freedom may be increased. As a number of joint plates 85 increases, the degree of bending freedom may increase. The Figures show three joint plates 85 between two adjacent plates (in FIGS. 58 and 59, between front and rear plates 830 and 840 of the lower body plate 82), but embodiments disclosed herein are not limited to a number of joint plates 85, and an appropriate number may be selected according to a desired tilting angle or degree of bending freedom.

A plurality of grooves of the extension ends 851 may engage with the plurality of extension ends 832 and 842 protruding from the side surfaces of the plates 810, 820, 830, and 840. The extension ends 851 may be formed at both front and rear ends or sides of the joint plate 85. Accordingly, the joint plate 85 and a side surface or end of a plate among the plates 810, 820, 830, and 840 may be meshed with each other. The joint hinge 86 may be a cylindrical rod passing through the grooves of the extension ends 832, 842, and 851. The joint hinge 86 may be a rotation axis between a joint plate 85 and an adjacent plate 810, 820, 830, and/or 840.

A portion where two adjacent plates 810, 820, 830, 840 are connected by one or more joint plates 85 may be defined as a joint bending portion. The joint bending portion may be a section including a plurality of joint plates 85 (e.g., three) and a plurality of joint hinges 86 (e.g., four) coupling the plurality of joint plates 85 to two adjacent plates 810, 820, 830, and/or 840.

Figure 60:
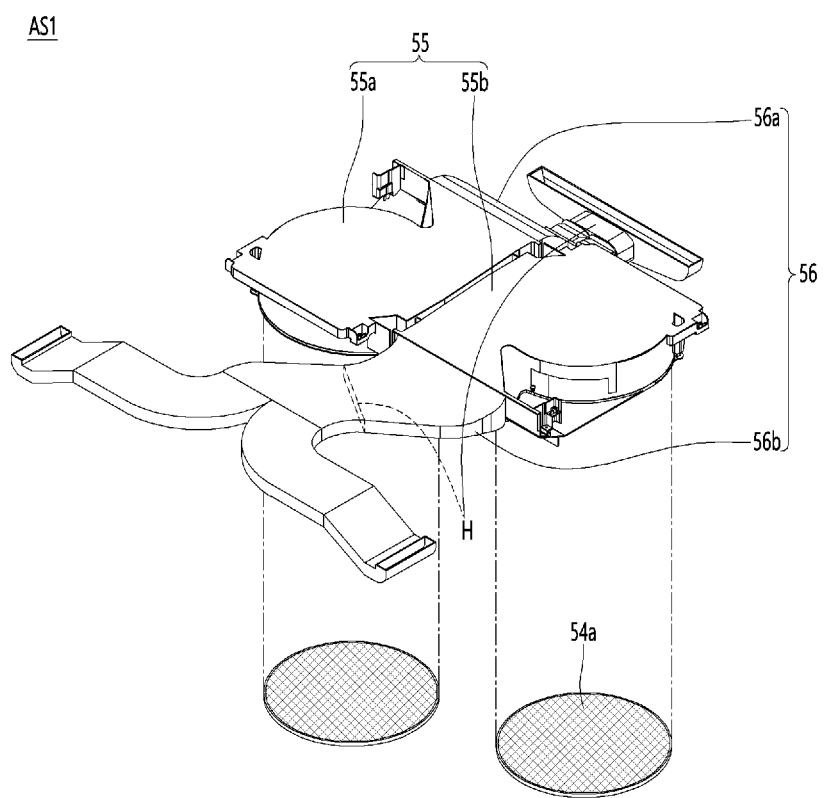
FIG. 60 is an exploded perspective view of a blowing assembly constituting the drying module of the bed according to an embodiment.

Referring to FIG. 60, as described above, the blowing assembly AS1 provided in the bed 10*b* may not require a separate suction duct. Suction ports or inlets may be formed on the bottom surfaces of the main fan 55*a* and the sub fan 55*b*, and filters 54*a* may be mounted at the respective suction ports.

By connecting the main fan 55*a* and the sub fan 55*b* to the main air dispenser 59*a* and the sub air dispenser 59*b*, respectively, an operation of the main air dispenser 59*a* and the sub air dispenser 59*b* may be independently controlled. Heaters H may be installed in the main supply duct 56*b* and the sub supply duct 56*b*, respectively, so that heat may be supplied to the mattress set MS1.

Figure 61:
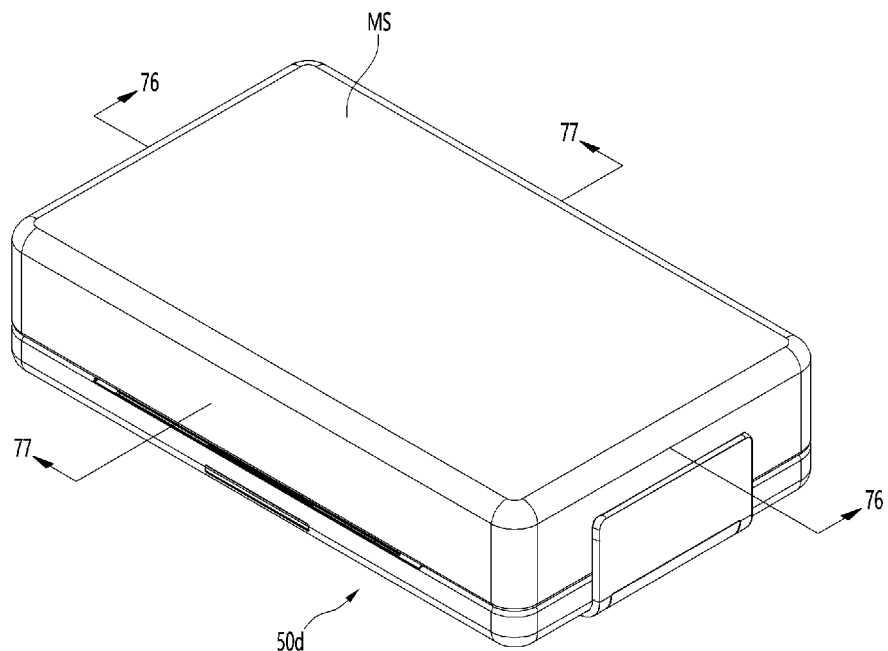
FIG. 61 is a perspective view of a bed according to another embodiment.
Figure 62:
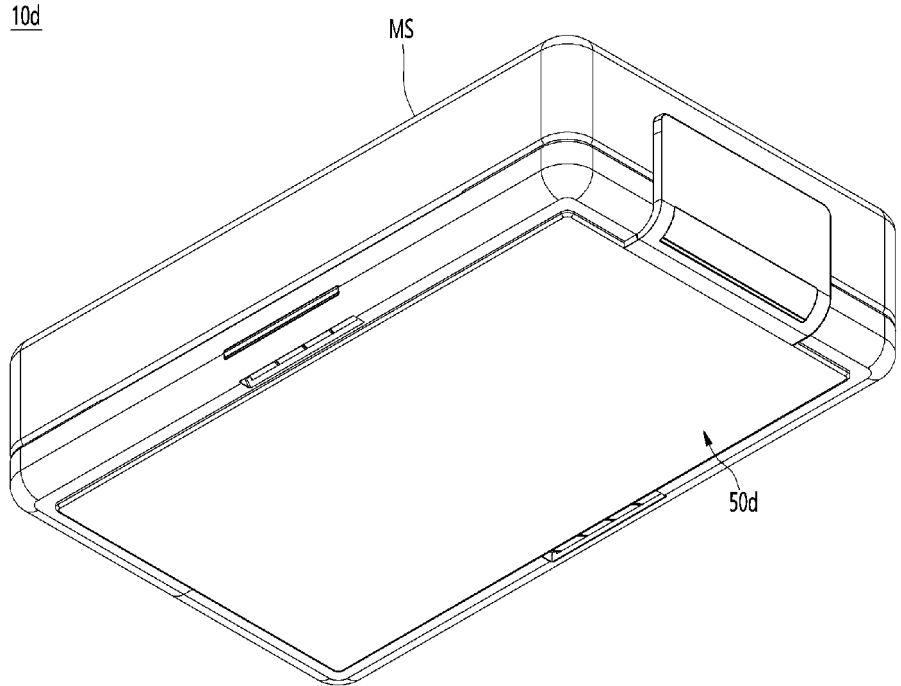
FIG. 62 is a bottom perspective view of a bed according to an embodiment.

Referring to FIGS. 61 and 62, a bed 10*d* according to another embodiment may include a mattress set MS and a drying module 50*d* on which the mattress set MS is placed. The mattress set MS of the bed 10*d* may be the same as or similar to the mattress set MS provided for the beds 10 and 10*a* previously described, and so a duplicate explanation is omitted. A bottom surface of the drying module 50*d* may contact the installation surface, but the drying module 50*d* may still omit the suction duct. Instead, the drying module 50*d* may differ from the drying modules 50*d* by spacing apart the fan 55 from the installation surface while the fan 55 is still inside an interior space of the drying module 50*d*. The drying module 50*d* and will be hereinafter described in more detail.

Figure 63:
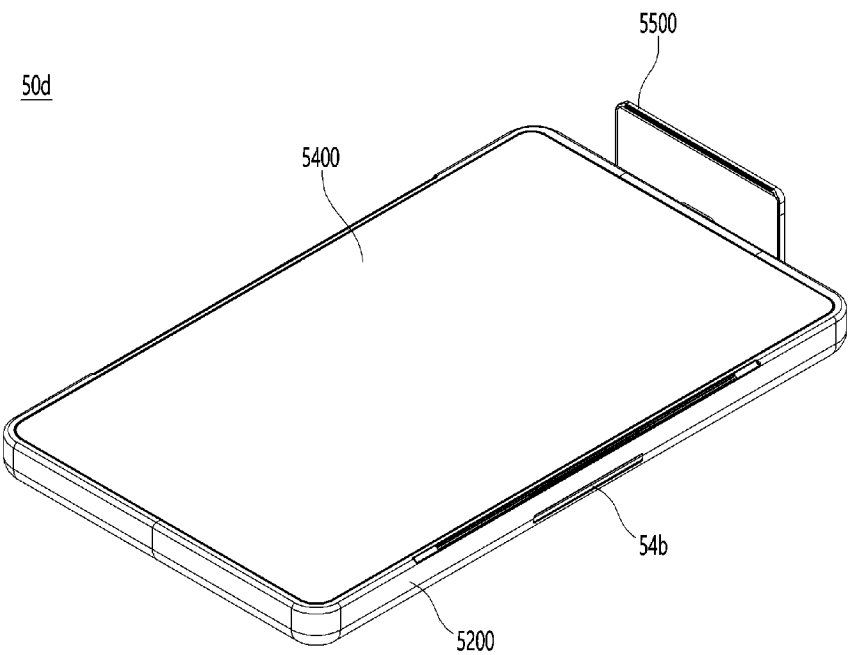
FIG. 63 is a perspective view of a drying module constituting a bed according to an embodiment.
Figure 64:
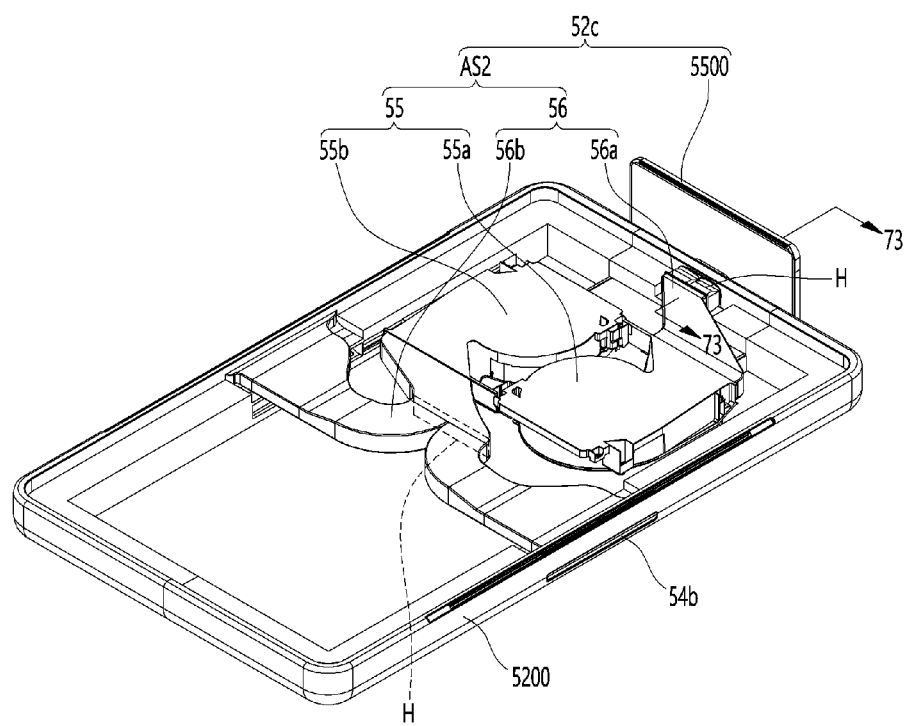
FIG. 64 is a perspective view showing an inside of the drying module.
Figure 65:
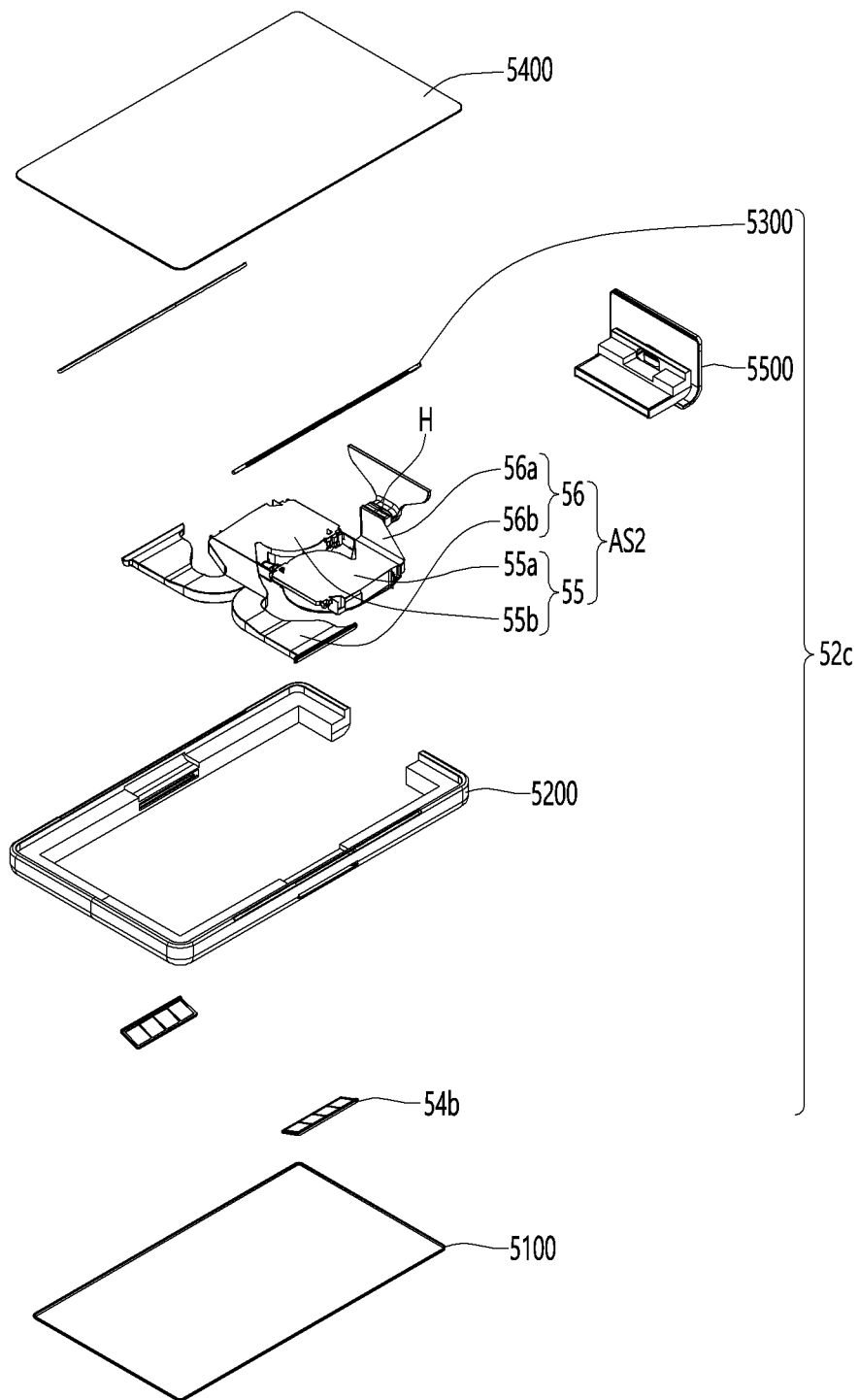
FIG. 65 is an exploded perspective view of the drying module.

Referring to FIGS. 63 to 65, the drying module 50*d* may include a set support and a blowing device 52*c* provided inside and outside the set support. The set support may include a base cover or bottom 5100 (FIG. 65) placed on an installation surface, a top cover 5400 provided above the base cover 5100 and defining a top surface of the set support, and an edge or side frame 5200 having an opened bottom surface covered by the base cover 5100 and an opened top surface covered by the top cover 5400.

The blowing device 52*c* may include a filter 54*b* detachable from the edge frame 5200, a blowing or fan assembly AS2 placed in an inner space of the edge frame 5200, an air dispenser 5500 coupled to an outlet of the fan assembly AS2, and a discharge grill 5300 covering an outlet or discharge port 5216 (FIG. 68) of the edge frame 5200 above the filter 54*b*. A vertical side wall of the edge frame 5200 may be formed with the discharge port 5216, and the filter 54*b* may be inserted into a bottom side of the edge frame 5200. A suction port 5217 may be provided on a bottom surface of the edge frame 5200 under the filter 54*b*, which may be inserted at an angle to cover the suction port 5217 (FIG. 70).

The fan assembly AS2 may include a fan 55 and a supply duct 56. The fan 55 may include a main fan 55*a* and a sub fan 55*b*, and the supply duct 56 may include a main supply duct 56*a* connected to an outlet of the main fan 55*a* a sub supply duct 56*b* connected to an outlet of the sub fan 55*b*. The blowing device 52*c* may further include heaters H installed in flow paths of the main supply duct 56*a* and the sub supply duct 56*b*.

The fan assembly AS2 may be substantially the same in configuration and function as the fan assembly AS1 of the bed 10*c* previously described. However, there is a difference in that the filter 54*b* may not be installed at the suction port of the blowing fan 55 but rather at the edge frame 5200.

The blowing device 52*c* may be defined as including the fan assembly AS2 and the air dispenser 5500, or alternatively may be defined as further including the filter 54*b* and the heater H. The edge frame 5200 may have a substantially rectangular shell shape, which may define an interior space of the dryer module 50*d* with the top and base covers 5400 and 5100. The base cover 5100 may be have a cross-sectional area smaller than that of the edge frame 5200 so as to be seated on the edge frame 5200, as will be described in more detail later.

Figure 66:
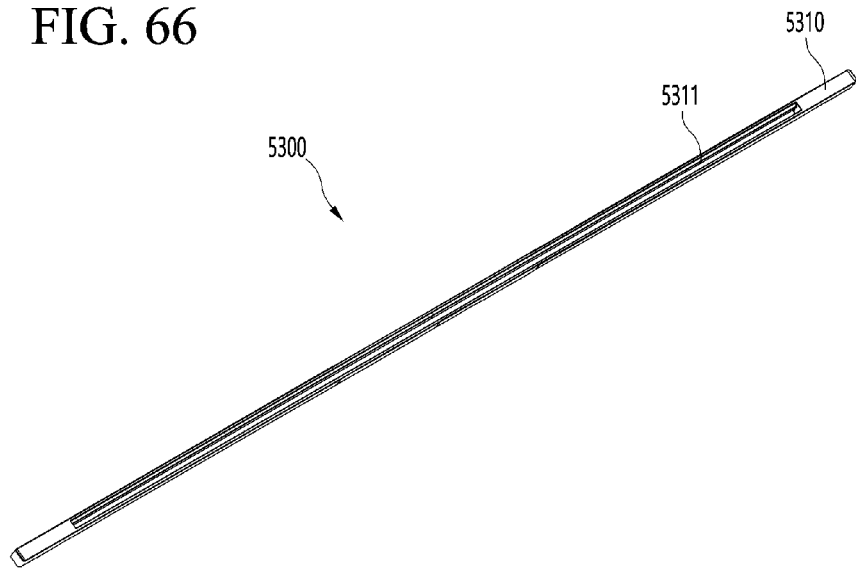
FIG. 66 is a perspective view of a discharge grill constituting a drying module according to an embodiment.

Referring to FIG. 66, the discharge grill 5300 may be provided in a discharge grill seating recess 5213 (see FIG. 68) formed in an upper edge of the edge frame 5200. The discharge grill 5300 may include a grill body or frame 5310 and a discharge port or slit 5311 that is elongated across a longitudinal direction of the grill body 5310.

The discharge port 5311 of the discharge grill 5300 may be formed to have a same size and shape as a size and shape of a sub discharge port 5216 (see FIG. 68) formed in the edge frame 5200, or alternatively may be formed to be longer. Embodiments disclosed herein are not limited so long as a flow of air through the sub discharge port 5216 is not obstructed by the grill body 5310.

Figure 67:
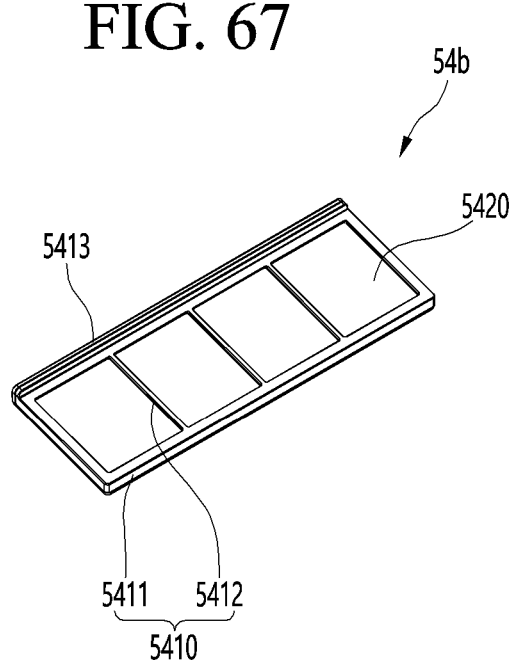
FIG. 67 is a perspective view of a filter constituting a drying module according to an embodiment.

Referring to FIG. 67, the filter 54*b* may include a filter frame or body 5410 having a rectangular shape, and a mesh material 5420 mounted within the filter frame 5410. Alternatively, the mesh material 5420 may be a HEPA filter, carbon filter, paper filter, fibrous filter, metal strainer, etc. Embodiments of the filter 54*b* are not limited.

The filter frame 5410 may include an outer body 5411 having a rectangular shell shape and a plurality of partition ribs 5412 dividing an inner space defined by the outer body 5411 into a plurality of small spaces. A handle 5413 may be formed on an edge of the outer body 5411 to facilitate manual removal from the edge frame 5200.

The mesh material 5420 may be coupled (e.g., adhered or welded) to an upper surface of the filter frame 5410, and the partition ribs 5412 may support the mesh material 5420 to prevent or reduce sagging. The handle 5413 may extend outward from an edge of a long side of the outer body 5411. The handle 5413 may protrude upward so that when the filter 54*b* is inserted into a filter insertion hole or slot 5212 (see FIGS. 68 and 70), a lip of the handle 5413 may be caught on the side of the edge frame 5200 to prevent the entire filter 54*b* from penetrating the filter insertion hole 5212 and being lost inside of the edge frame 5200.

Alternatively, when the filter 54*b* is inserted into the filter insertion hole 5212, an outer surface of the handle 5413 may be flush with a side surface of the edge frame 5200. Further, a gripping groove may be formed on an outer surface of the handle 5413 so that the user may remove the filter 54*b* by putting a finger into the gripping groove.

Figure 68:
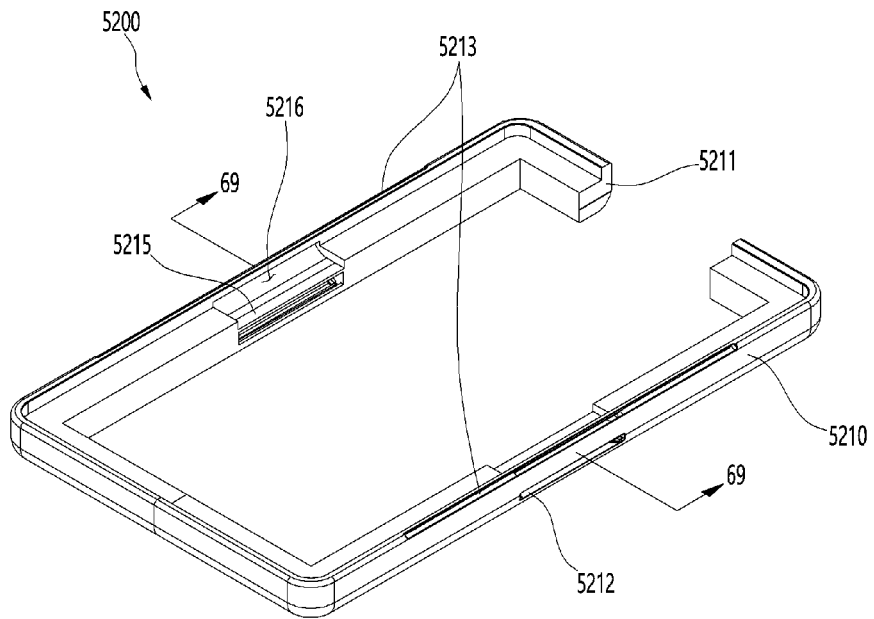
FIG. 68 is a perspective view of an edge frame constituting a drying module according to an embodiment.
Figure 69:
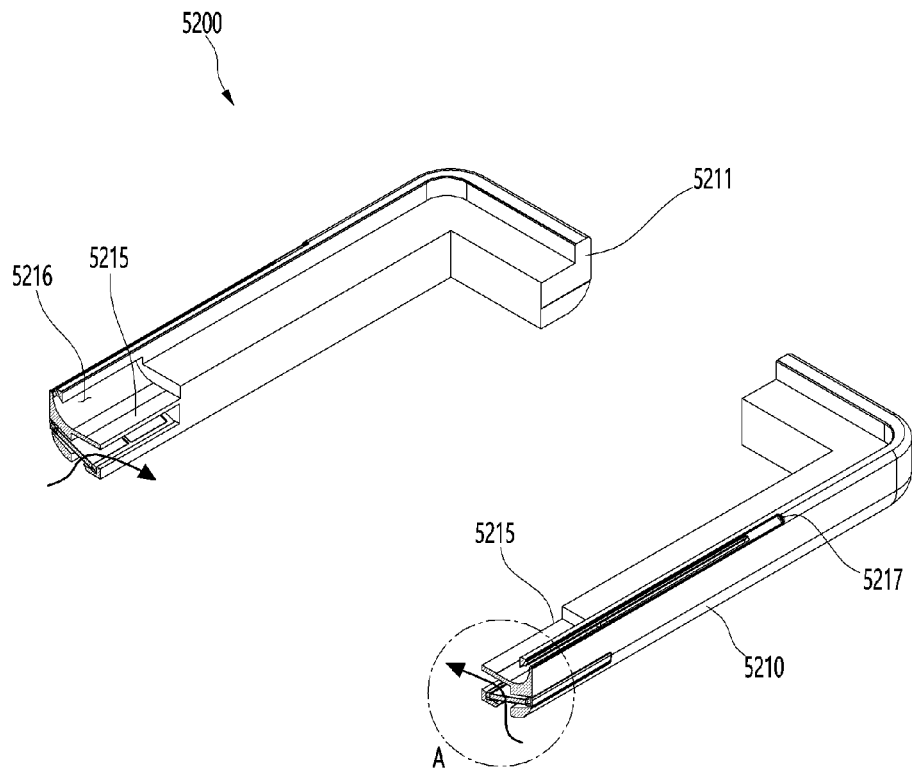
FIG. 69 is a cutaway perspective view of the edge frame cut along 69-69 of FIG. 68.

Referring to FIGS. 68 to 70, the edge frame 5200 may have a rectangular strip shape so as to have two long sides facing each other and two short sides facing each other. An opening 5211 may be formed at one of the two short sides such that a perimeter of the edge frame 5200 may not form a complete rectangle. The air dispenser 5500 may be provided in the opening 5211.

Filter insertion holes or slots 5212 may be formed in the two long sides of the edge frame 5200 to face each other. The filters 54*b* may be inserted into the filter insertion holes 5212. The filter insertion hole 5212 may be formed to be inclined or angled downward from an outer surface to an inner surface of the edge frame 5200, and the filters 54*b* may be inserted at an angle to facilitate insertion.

A filter seating surface 5214 (FIG. 70) may be formed inside the edge frame 5200 to receive and support an end of the filter 54*b*. The filter seating surface 5214 may be stepped to have an inner contour corresponding to a shape of the end of the filter 54*b* when the filter 54*b* is inserted a maximum amount into the filter insertion hole 5212. The filter seating surface 5214 may include both a vertical recess and a diagonal recess in an inner surface of the edge frame 5200.

The suction port 5217 may be formed at the bottom of the edge frame 5200 to be directly below the filter 54*b*. The suction port 5217 may be spaced a predetermined distance g from the installation surface by the base cover 5100 to facilitate ambient air inflow. As an alternative, the suction port 5217 may be formed in the long side of the edge frame 5200 below the discharge port 5213, and the filter 54*b* may be configured to cover the suction port 5217. Since the suction port 5217 may be formed under the filter 54*b*, ambient air flowing into the suction port 5217 may pass through the filter 54*b* so that foreign matter contained in the ambient air may be filtered out.

Ambient air suctioned through the suction port 5217 may flow along a suction flow path 5217*a* bent in an "L" shape from the suction port 5217 and penetrating an inner surface of the edge frame 5200. A suction end of the suction flow path 5217 may be provided at the suction port 5217, while a discharge end of the suction flow path 5217*a* may be inside the edge frame 5200. Air suctioned through the suction port 5217 may flow along the suction flow path 5217*a*, which may eventually lead to the inlet of the blowing fan 55 to guide the air toward the blowing fan 55.

A sub-supply duct seating recess 5215 may be formed in the edge frame 5200 and may be separated from the suction flow path 5217a. The sub-supply duct seating recess 5215 may be stepped downward by a predetermined depth from an upper surface of the edge frame 5200. The sub-supply duct 56b may be provided in the sub-supply duct seating recess 5215, and a width of the sub-supply duct seating recess 5215 may correspond to as width of the sub-supply duct 56b.

The sub discharge port 5216 may be formed at an edge or corner of the edge frame 5200 at an outer end of the sub supply duct seating recess 5215. When the sub-supply duct 56b is seated in the sub-supply duct seating recess 5215, air discharged from the sub-supply duct 56b may pass through the sub-discharge port 5216 of the edge frame 5200 to be discharged outside of the bed 10d.

The sub-supply duct seating recess 5215 may be provided above and separated from the suction port 5217, but embodiments disclosed herein are not limited. For example, the suction port 5217 may alternatively be formed in a center of the long side of the edge frame 5200 closer to any one of the two short sides of the edge frame 5200, or below the filter insertion hole 5212.

Figure 73:
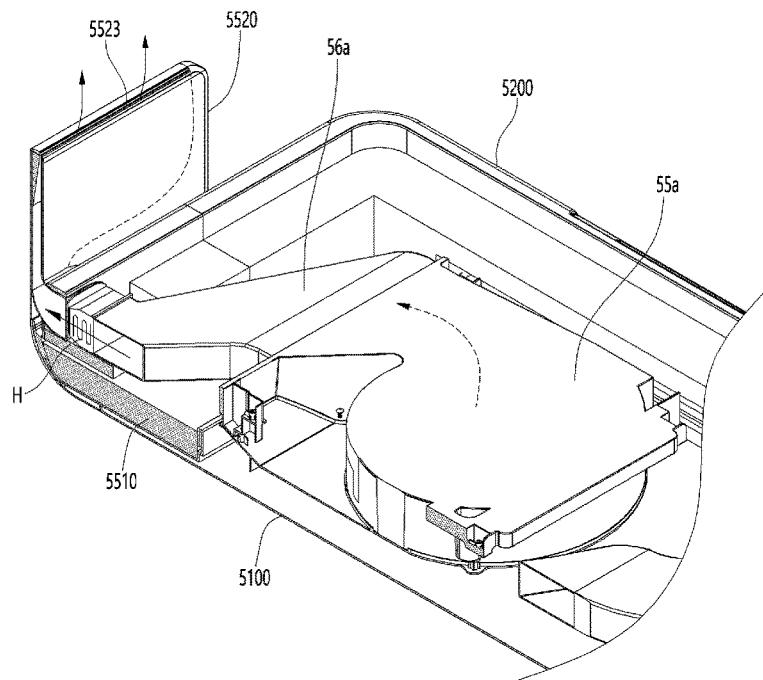
FIG. 73 is a partially cut-away perspective view of the drying module cut along 73-73 of FIG. 64.

Referring to FIGS. 71 to 73, the air dispenser 5500 may include a main supply duct support or ledge 5510 and a dispenser body 5520 coupled to an outer surface of the main supply duct support 5510. An upper surface of the main supply duct support 5510 may be stepped multiple times to have a stair shape, but embodiments disclosed herein are not limited.

A heater seating recess 5511 may be formed to be stepped on an upper stair surface of the main supply duct support 5510. A heater housing in which the heater H may be housed may be provided in the heater mounting recess 5511.

A communication or guide hole 5512 may be formed at an outer edge of the main supply duct support 5510. An end of the main supply duct 56a may be inserted into the communication hole 5512 or have an inlet communicating with the communication hole 5512.

The main supply duct support 5510 may be mounted at the opening 5211 formed at the short side of the edge frame 5200, or alternatively be formed integrally with the edge frame 5200. In such an embodiment, the opening 5211 may be excluded, and the air dispenser 5500 may include the dispenser body 5520 but not the main supply duct support 5510.

A lower portion of the dispenser body 5520 may be curved or rounded from a side surface to a bottom surface to surround a similarly curved or rounded outer corner of the main supply duct support 5510 and/or an outer side of the edge frame 5200. An inlet port 5521 may be formed on an inner surface of the dispenser body 5520 that contacts the main supply duct support 5510. The inlet 5512 may align and communicate with the communication hole 5512 of the main supply duct support 5510.

A side surface of the dispenser body 5520 may include an inner wall having the inner surface that contacts the main supply duct support 5510 and an outer wall provided outside of the inner wall. A diffuser 5522 may be formed inside the dispenser body 5520 and defined by an inner space, and an outlet 5523 may be formed on an upper surface or end of the dispenser body 5520 extending between the inner and outer walls.

The outlet 5523 may be formed to be closer to the inner wall than the outer wall such that a distance from a rear end or side of the outlet 5523 to the outer wall may be longer than a distance from a front end or side of the outlet 5523 to the inner wall. The diffuser 5522 may have a left-right cross-sectional area and volume that increases from the inlet port 5521 to the outlet port 5523.

An air guider or guide surface 5524 may be formed inside the dispenser body 5520 on the outer wall at the rear side of the outlet 5523. A front surface of the air guider 5524 may be inclined so as to be thicker at the outlet 5523 and thinner downward toward the inlet port 5521. A front-rear cross-sectional area of the diffuser 5522 below the air guider 5524 may be larger than a cross-sectional area of the outlet 5523. Since a front surface of the air guider 5524 may be inclined, the air discharged through the outlet 5523 may be discharged toward the upper surface of the mattress set MS1.

When the heater H is provided in a flow path of the main supply duct 56a and turned on, hot air may be discharged through the outlet 5523 to dry the mattress set MS. The upper end of the dispenser body 5520 may be spaced a predetermined distance downward from an upper surface of the mattress set MS while the mattress set MS is placed on the top cover 5400.

Figure 74:
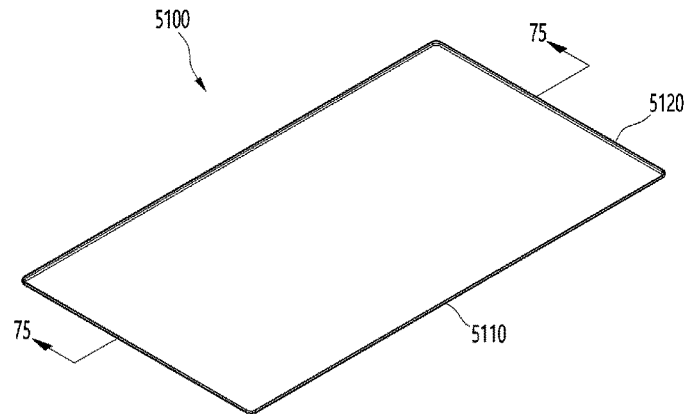
FIG. 74 is a perspective view of a base cover constituting a drying module according to an embodiment.
Figure 75:
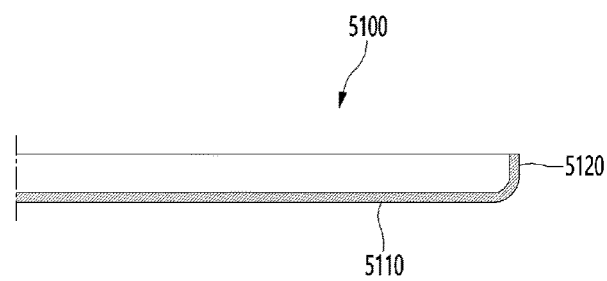
FIG. 75 is a partial longitudinal sectional view of a base cover taken along 75-75 in FIG. 74.

Referring to FIGS. 74 and 75, the base cover 5100 may seal an opened bottom surface of the edge frame 5200 and space the edge frame 5200 apart from the installation surface so that air may enter the suction port 5217. The base cover 5100 may include a rectangular plate-shaped bottom 5110 and a side wall 5120 bended or rounded upward from tan edge of the bottom 5110.

When the base cover 5100 is coupled to a bottom surface of the edge plate 5200, the bottom surface of the edge plate 5200 may be spaced apart from the installation surface by a height of the side wall 5120. The suction port 5217 formed on the bottom surface of the edge cover 5200 may also be spaced apart from the installation surface, thereby reducing a flow resistance when ambient air is suctioned into the suction port 5217.

Figure 76:
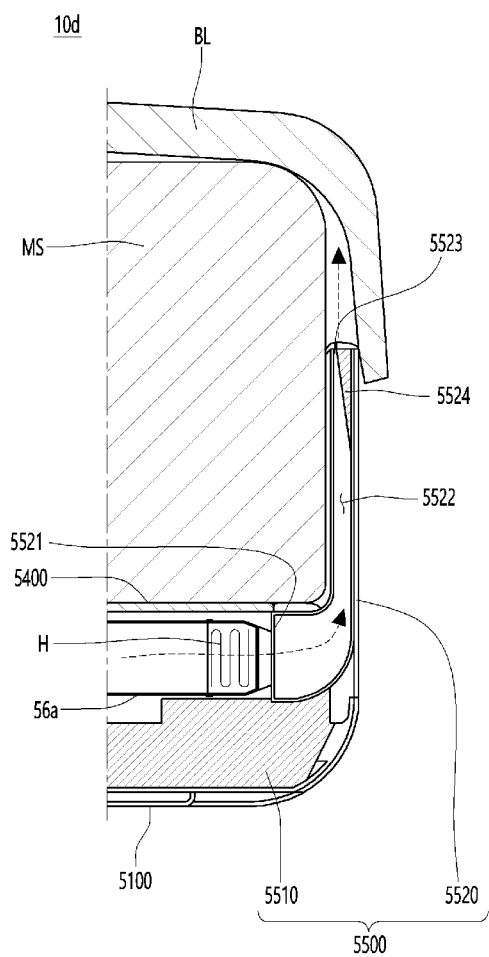
FIG. 76 is a partial longitudinal sectional view of a bed taken along 76-76 of FIG. 61.

Referring to FIG. 76, when a blanket BL is placed on the mattress set MS such that an end of the blanket is stretched or falls over the outlet 5523 of the air dispenser 5500 to cover the outlet 5523, air may still be discharged out of the outlet 5523 into a space between the mattress set MS and the blanket BL because the air dispenser 5500 may protrude outward with respect to the mattress set MS.

When the heater H is on, hot air discharged through the outlet 5523 may flow between the mattress set MS and the blanket BL to dry the bed cover 11 and the blanket BL and warm the blanker BL. When a humidity is high (e.g., during summer), the mattress set MS and the blanket BL may be quickly dried by the hot air discharged through the outlet 5523, so that the user can feel dry even when the blanket BL covers him. Even when the mattress set MS is not covered by a blanket BL, the air discharged from the outlet 5523 may flow along a side of the mattress set MS due to the Coanda effect, as a side of the mattress set MS may be naturally convex or curved outward. The air may stay close to or cling to the convex side surface or rounded edge of the mattress set MS.

Figure 77:
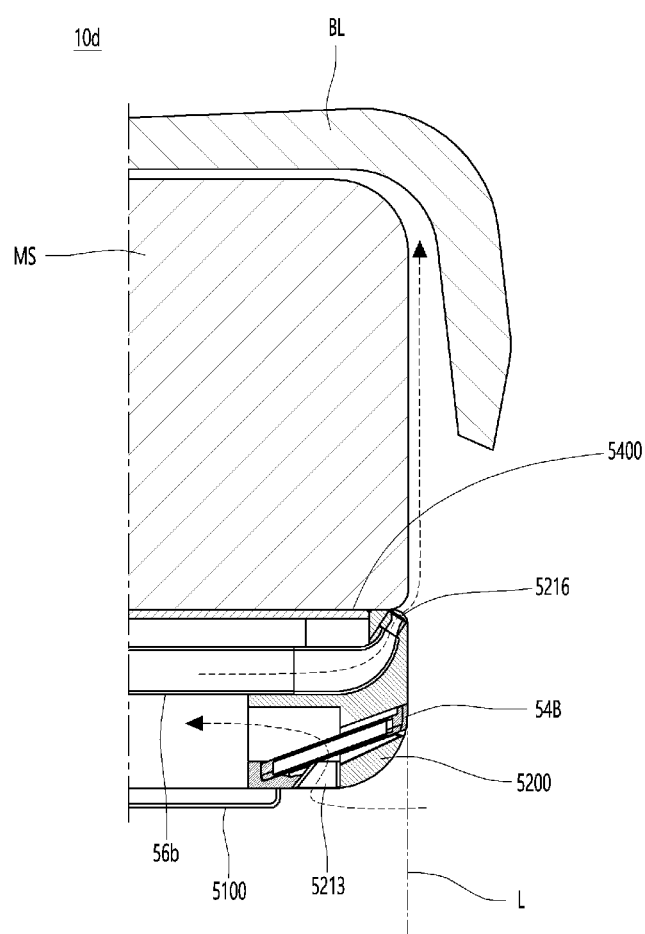
FIG. 77 is a partial longitudinal sectional view of a bed taken along 77-77 of FIG. 61.

Referring to FIG. 77, the sub-discharge port 5216 formed on the upper surface of the edge frame 5200 may be provided at an outer side of the mattress set MS while the mattress set MS is placed on the top cover 5400. The sub-discharge port 5216 may be angled at a corner of the edge frame 5200 so as to discharge air past a bottom rounded corner of the mattress set MS. Due to the Coandã effect, the air may cling to a side of the mattress set MS such that a flow of air may be provided at an inner side of a line L that extends upward from an outermost dimension of the edge frame 5200. The sub discharge port 5216 may be positioned to be spaced apart from the line L, which may pass through the mattress set. Alternatively, an outer edge of the sub discharge port 5216 may lie along the line L.

By the above-described Coanda effect, a flow of the air discharged through the sub-discharge port 5216 may include a lower curved portion, a side portion, and a curved portion at the upper end of the mattress set MS. The discharged air may flow along the outer side of the mattress set MS and may spread to the upper surface of the mattress set MS under a blanket BL.

Figure 78:
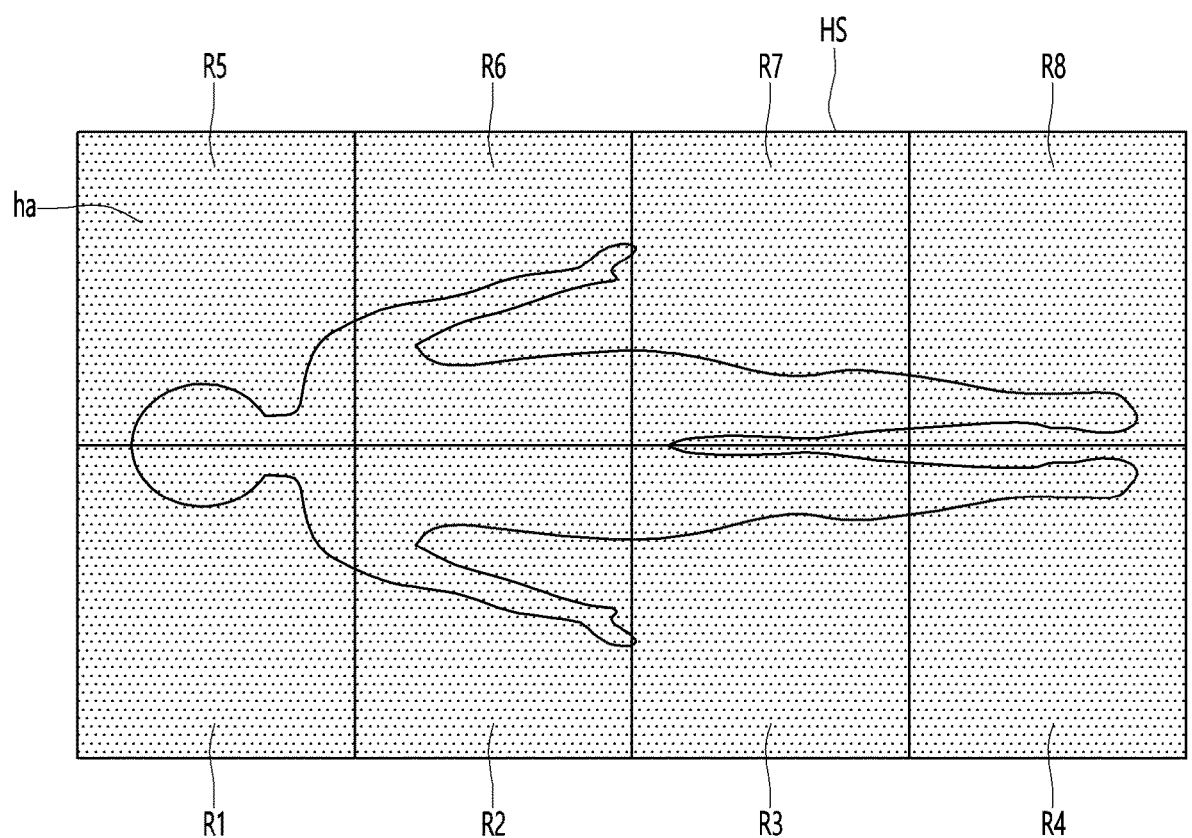
FIG. 78 is a plan view of a humidity sensing sheet provided in a mattress set for a bed according to an embodiment.

Hereinafter, a humidity control method will be described in detail. Referring to FIG. 78, a humidity detection sheet HS may be provided in the mattress set MS of the bed according to an embodiment. The humidity detection sheet HS may be implemented in the bed cover 11 or as a separate sheet provided over the topper 12 and/or the bed cover 11, and may have a size corresponding to a size of the topper 12.

A plurality of humidity sensors ha may be provided in (e.g., woven into) the humidity sensing sheet HS, and the plurality of humidity sensors ha may be electrically connected to a controller of the humidity sensing sheet HS. The controller of the humidity detection sheet HS may be defined as a sub controller, while the controller of the bed may be defined as a main controller.

The main controller and the sub controller may communicate with each other via communication modules, which may have WiFi or Bluetooth modules, or alternatively may be wired to each other. The main controller may transmit a humidity detection command to the sub controller or may receive a humidity value from the sub controller. The main controller may control an operation of the fan 55 and the heater H of the dryer module 50*a*, 50*b*, 50*c*, 50*d*, etc. based on the received humidity value.

In addition, the main controller and the sub controller may be connected to a humidity controller to be described later through wireless communication. A humidity control command may be output from the humidity controller, and the humidity control command may be transmitted to the main controller and then transmitted from the main controller to the sub controller. Alternatively, a humidity control command may be directly transmitted from the humidity controller to the sub controller.

The humidity sensing sheet HS may be divided into a plurality of regions R1 to R8, and humidity control for each region may be independent. A number of areas may be variously set according to design conditions.

A number of humidity sensors ha installed in each area may be appropriately set in consideration of cost and installation difficulty. A humidity value for each region may be determined as an average value of humidity values sensed from the humidity sensors ha installed in the corresponding region. The maximum value and the minimum value among humidity values detected by the humidity sensors ha installed in the corresponding region may be optionally excluded, and various methods of calculating the humidity value of the corresponding region may be implemented. Embodiments disclosed herein are not limited to a method of calculating or determining an overall humidity value for each region.

Various types of humidity sensors may be implemented as the humidity sensors, including an electrical resistance type humidity sensor in which electrodes are printed on a flexible substrate in the form of a thin film. However, when the user lies on the humidity detection sheet HS, the humidity sensor hs may have a flat shape so as not to protrude toward a user's body or cause discomfort. A humidity sensing circuit connecting the humidity sensors ha may be configured so as not to be damaged by a bending or pulling of the bed cover 11 and/or the humidity sensing sheet HS.

The humidity sensing sheet HS may be combined with the bed cover 11 as one body, which may further be optionally combined with a top surface of the topper 12. Alternatively, in addition to a method in which the humidity sensor ha may be mounted on a separate sheet or film, the humidity sensor ha may be directly mounted on or installed in (e.g., woven in) the top surface of the topper 12.

The humidity sensor ha may detect a humidity of the topper 12 as well as the bed cover 11 covering the topper 12. The mattress set MS, MS1 may be vulnerable to moisture due to secretions (e.g., sweat) released from the user's body during sleep, spilled water or beverages, or moisture absorbed from humid air in midsummer. If the mattress remains moist or wet for a long time, mold or mites may grow on the bed cover 11 or the topper 12, resulting in poor hygiene and air quality, which may adversely affect the user's health.

Such a humid condition may occur only in certain parts of the mattress set MS, in particular the bed cover 11 or the topper 12. To effectively eliminate or greatly reduce an over-humidity condition that may occur, the humidity sensing sheet HS and the heater H of the drying module 50, 50*a*, 50*b*, 50*c*, 50*d* may be efficiently controlled such that heat may be applied to overly moist or wet regions.

Hereinafter, a control method of the drying module 50, 50*a*, 50*b*, 50*c*, 50*d* based on the humidity value sensed by the humidity sensors hs of the humidity sensing sheet HS will be described in detail using a flowchart (FIG. 79), and possible display screens of a humidity controller 800 (FIGS. 80-84) shown in a process of performing the method of controlling humidity of a bed according to an embodiment.

Figure 79:
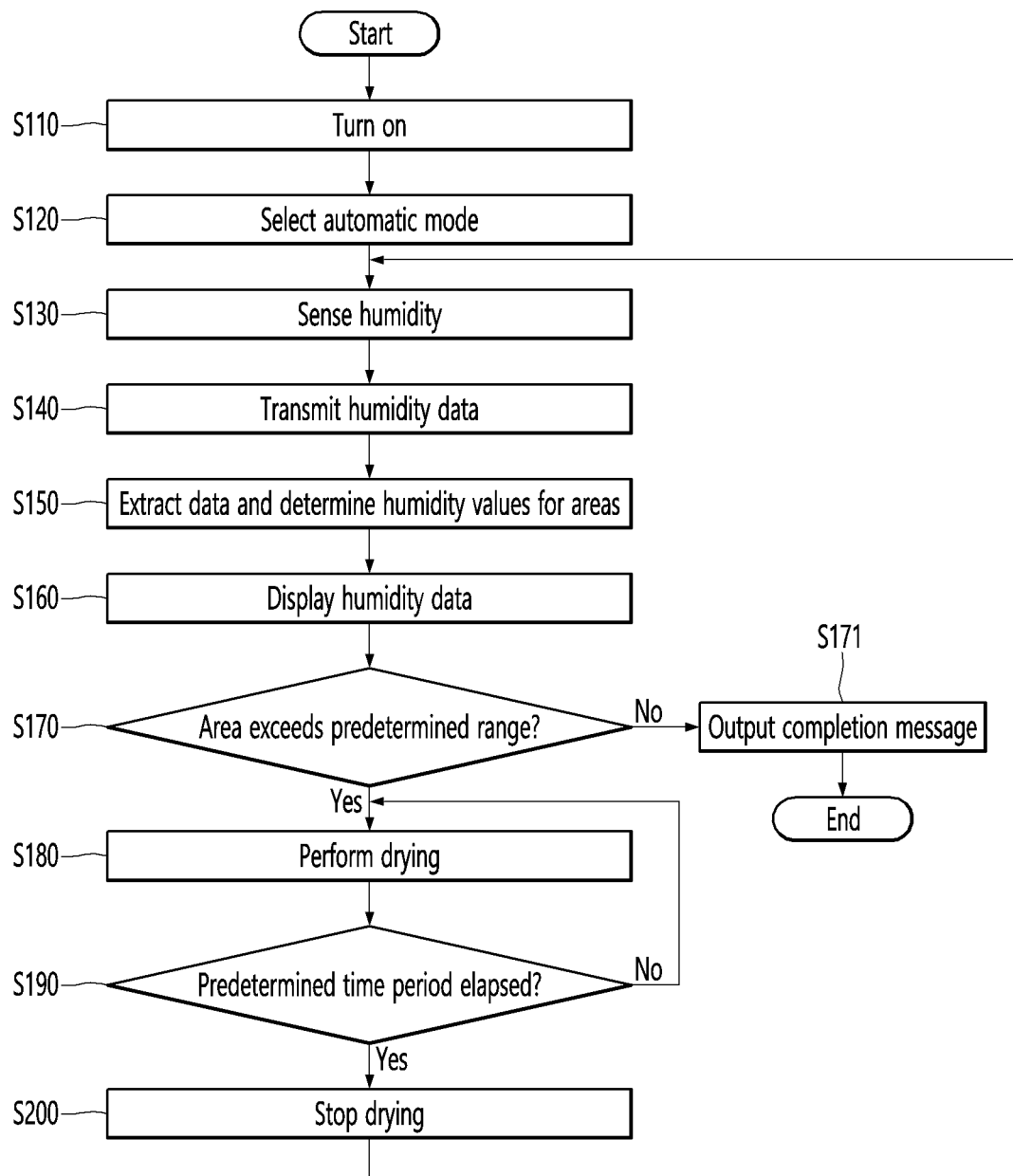
FIG. 79 is a flowchart showing a method for controlling humidity of a bed according to an embodiment.

Referring to FIG. 79, the bed 10, 10*a*, 10*b*, and 10*c* may be turned or powered on by the user (S110). When the power of the bed is turned on, at least one of the bedframes 30 and 300, the humidity sensing sheet HS, a humidity controller or regulator 800 to be described later, and a control box provided in the bed 10, 10*a*, 10*b*, 10*c* may be turned on.

The user may operate the humidity controller 800, which may be a remote controller that is wirelessly connected to the controller of the bed 10, 10*a*, 10*b*, 10*c* to select an automatic dehumidification operation or mode (S120). The main controller, sub controller, and humidity controller 800 may all include a printed circuit board (PCB), a microcomputer or a processor, a memory or storage, communication modules (e.g., WiFi, Bluetooth, or ZigBee modules), etc.

Figure 80:
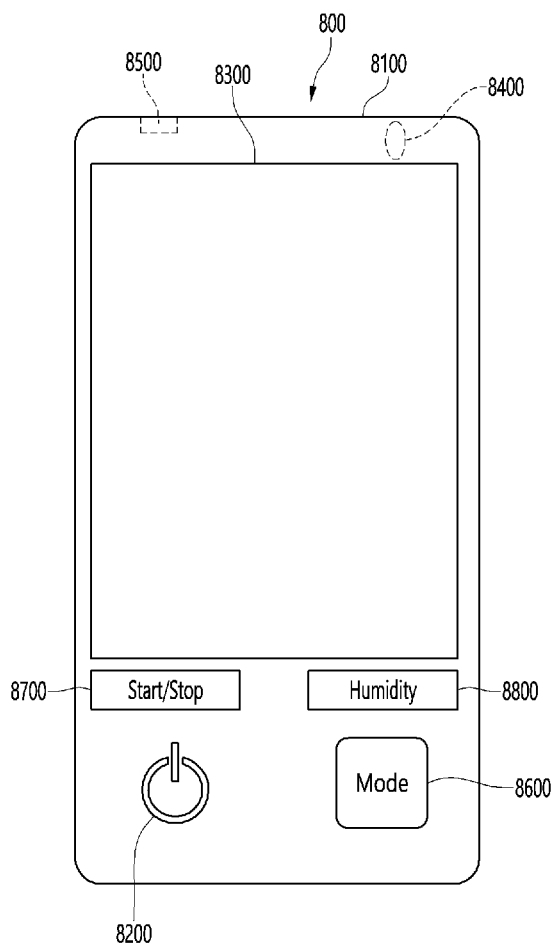
FIGS. 80 to 84 are display screens of a humidity controller shown in a process of performing a method for controlling the humidity of a bed according to an embodiment.

Referring quickly to FIG. 80, a humidity controller 800 may include a main body 8100, a power button 8200 provided on a front side of the main body 8100, and a display 8300 provided on a front side of the main body 8100. The humidity controller 800 may be provided with a plurality of mechanical input buttons, a plurality of touch input buttons, and/or the display 8300 may be implemented as a touch screen having a plurality of applications or buttons, such as on a mobile phone. The power button may be a mechanical button or switch that the user must press with a certain amount of force.

For example, when the user presses the power button 8200, the display 8300 may be activated, and the humidity controller 800 and the sub-controller may be in a standby state or a state where communication is possible. An image selectable by a user may be displayed on the display 8300 as a background or welcome screen.

The plurality of mechanical input buttons may include a mode selection button 8600 to select a mode, which may include an automatic dehumidification operation or mode, an execution/stop button 8700 to input an execution or stop command of a selected mode, and a reference humidity setting button 8800 to set a humidity level desired to be maintained.

A temperature sensor 8400 to sense an indoor temperature and a wireless communication module 8500 to wirelessly communicate with the main controller and the sub controller may be built in a side of the main body 8100. The wireless communication module may include Wi-Fi, Bluetooth, ZigBee, etc. The temperature sensor 8400 may alternatively be provided on any side of the humidity detection sheet HS or at any one side of the bed 10, 10a, 10b, 10c (e.g., on the safety guard 13 or guard frame 60), and a sensed temperature value may be transmitted to the sub controller or the main controller.

The reference humidity may be used to determine whether a humidity of the mattress set MS, MS1 sensed from the humidity sensing sheet HS is excessively high for a current temperature or at an appropriate level for the current temperature. The reference humidity may mean an appropriate humidity corresponding to a room temperature detected by the temperature sensor 8400. The reference humidity may be understood to mean a humidity that the user feels most comfortable at a corresponding temperature.

For example, the reference humidity may need to be set differently according to a season, and an appropriate humidity may be determined or calibrated for each temperature range. Temperature versus humidity data may be stored in the main controller in the form of a lookup table.

For example, appropriate humidity values according to seasonal temperatures may be stored in the form of a lookup table as shown in Table 1 below.

TABLE 1

|  | Summer | Spring/Fall | Winter |
| --- | --- | --- | --- |
| Optimum Temperature | 24° C. ~ 28° C. | 19° C. ~ 23° C. | 18° C. ~ 20° C. |
| Optimum Humidity | 60% | 50% | 40% |

While a reference humidity may be automatically selected from a reference humidity stored in the lookup table, the user may freely set the reference humidity at the current temperature by using the reference humidity setting button 8800.

Referring back to FIG. 79, when the user selects the automatic dehumidification operation or mode using the mode selection button 8800, a plurality of humidity sensors ha provided in the humidity detection sheet HS may sense a humidity (S130). An operation of receiving a dehumidification operation command from the sub-controller and causing the plurality of humidity sensors ha to sense the current humidity may be defined as a current humidity scan operation.

Figure 81:
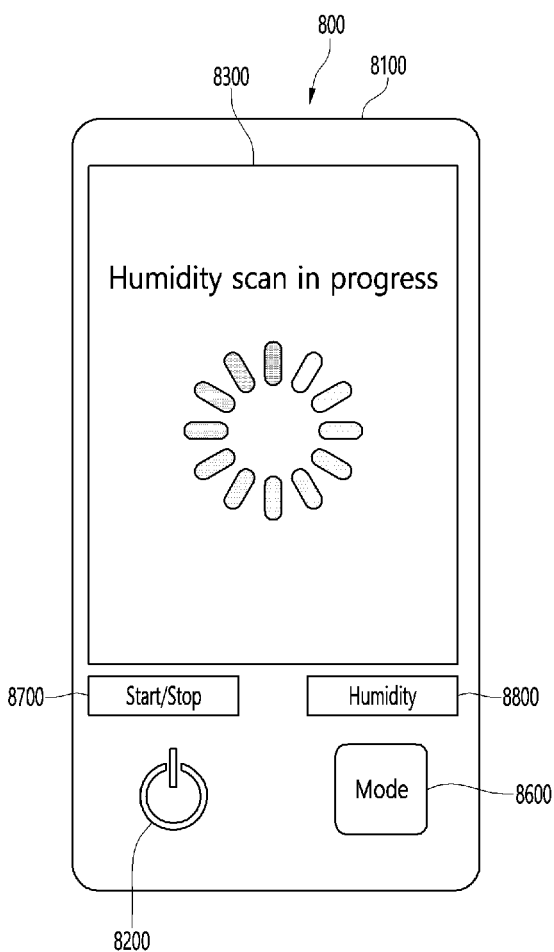

Referring quickly to FIG. 81, while a current humidity scan operation is being performed (S130), text, image, or video information indicating that the humidity is currently being scanned may be output on the display 8300 of the humidity controller 800.

Referring back to FIG. 79, the scanned humidity values (i.e., humidity data) sensed from the plurality of humidity sensors ha may be transmitted to the main controller (S140). The main controller may extract the humidity data and determine an average humidity value for each region by processing and analyzing the humidity values transmitted from the sub controller (S150). Then, a humidity distribution image or chart for each region may be generated using the extracted average humidity value for each region, and the generated image may be transmitted to the humidity controller 800 to be output on the display 8300 (S160).

Figure 82:
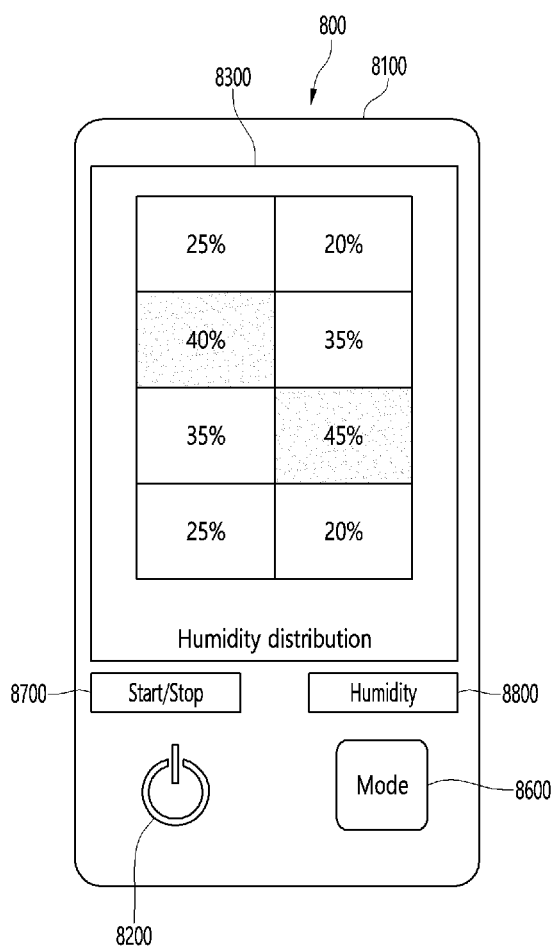

As shown in FIG. 82, a humidity distribution chart for each region may be output on the display 8300 of the humidity controller 800 (S160). As an alternative, an image (e.g., a color graded image) may be shown, which may be based either on the average humidity values or, alternatively, based on the humidity sensed by each individual humidity sensor ha to show a more detailed rendering.

Referring to FIGS. 79 and 82, the main controller may set or predetermine a normal or predetermined humidity range in consideration of an upper and lower error range based on the set reference humidity, and determine whether an area or region among the plurality of areas has an average humidity value outside the predetermined humidity range (S170). When it is determined that there is an area having an average humidity outside of the predetermined humidity range ("Yes" after S170), the overly humid area may be prominently display on the display 8300. At the same time, the main controller may perform a drying operation by operating at least one of the heater H, the fan 55, or the damper 561 to reduce a humidity in the corresponding area (S180). Such a step S180 may be referred to as a drying step.

The fan 55 to which a corresponding supply duct 56 extending to the overly humid region is connected may be driven for a predetermined time period, and the heater H provided in the flow path of the corresponding supply duct 56 may be turned on for the predetermined time period. The damper 561 provided on the flow path of the corresponding supply duct 56 may be opened so that hot air may be concentrated and discharged to the overly humid area.

Figure 83:
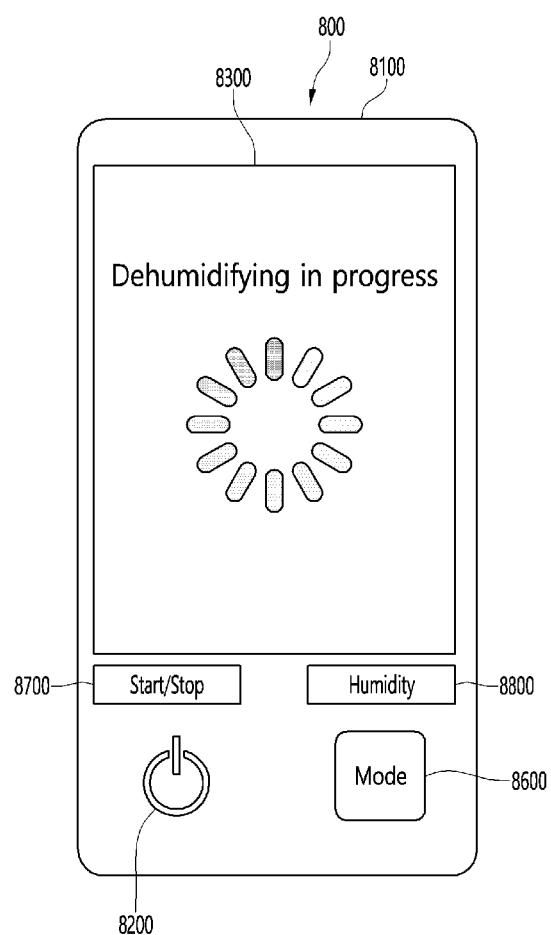

When hot air is supplied to the mattress set MS, MS1 and a dehumidification operation (or drying operation) is being performed, the display 8300 of the humidity controller 800 may notify the user that a dehumidification operation is in progress (FIG. 83). The main controller or the sub controller may continuously sense whether the predetermined time period has elapsed (S190), and when the predetermined time period has elapsed, a drying operation may be stopped such that the fan 55 and the heater H may be turned off or stopped, and the damper 561 may be closed (S200). A process of scanning the current humidity (S130) may be repeated.

Figure 84:
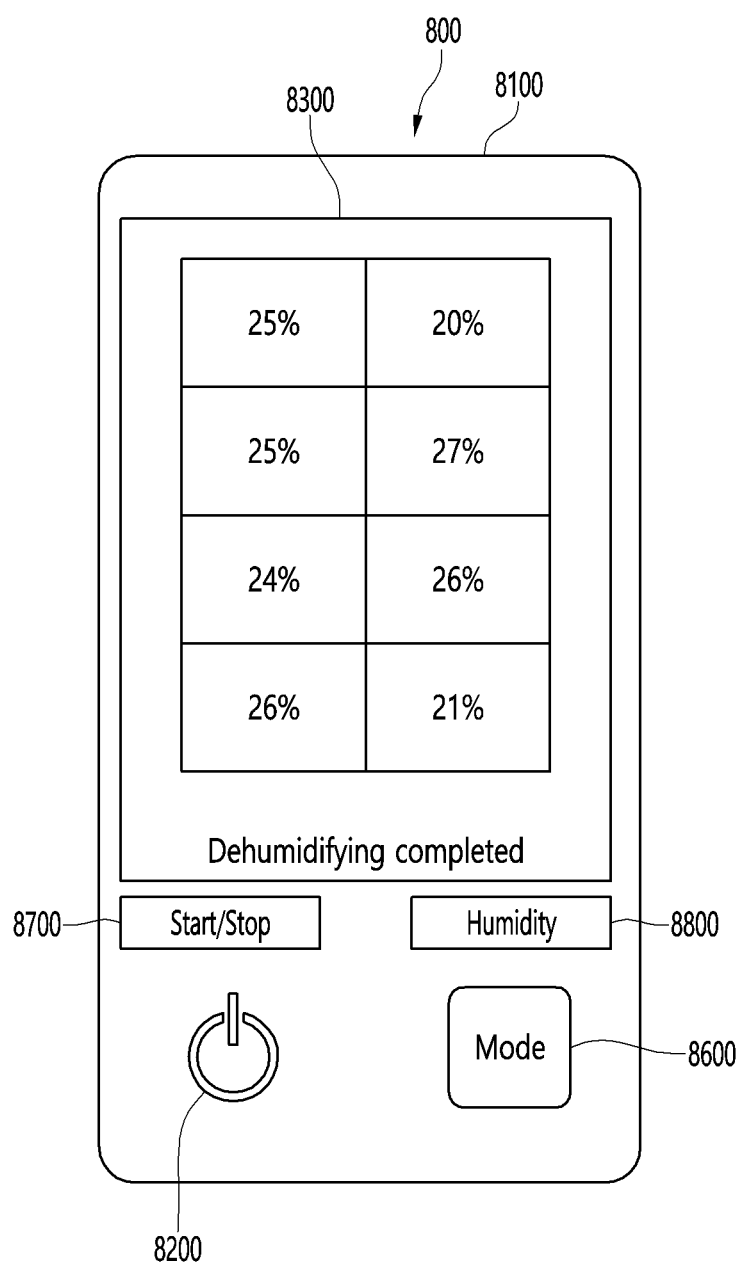

When this dehumidification operation process is performed once or multiple times, and the main controller determines that the humidity of the region initially determined as the overly humid region has entered the predetermined humidity range, a dehumidification completion message may be output (S171). FIG. 84 shows that a humidity distribution image for each region or area indicating a current humidity value after the dehumidification operation is performed together with a dehumidification completion message may be displayed on the display 8300 of the humidity controller 800.

By automatically supplying hot air to a specific area where humidity is excessively high, the mattress set MS, blanket BL, and/or the bed cover 11 may be maintained in a dry state to improve sleep.

Embodiments disclosed herein may solve problems described above. Embodiments disclosed herein may provide a bed that includes a mattress set on which the user's body is placed on an upper surface. A cover sheet may surround and/or bundle the mattress set. The mattress set may be provided on a bedframe and/or an installation surface. A dryer or drying module may supply dry air into the mattress set. The drying module may be configured to support the mattress set above the installation surface.

The drying module may include a set support including an upper surface on which the mattress set is placed and a side wall extending downwardly along an edge of the upper surface to contact the installation surface. A blowing device may be mounted below the set support. The blowing device may include a blowing fan, a suction duct connected to a suction port of the blower fan and suctioning ambient air through suction ports formed at both ends, and a supply duct connected to the discharge port of the blowing fan to supply suctioned ambient air to the mattress set.

A height of an inner spring provided inside a cushion of the mattress set may be adjusted, and the user may easily set a desired level of cushion strength or firmness. The cushion strength may be linearly adjusted through a height adjustment of the inner spring. A drive may be connected to a transmission gear provided at a lower end of the cushion, and a cushion strength of the plurality of cushions may be adjusted to a same level at once.

A firmness adjuster may include a plurality of firmness adjusters or strength control modules, and each firmness adjuster may include a plurality of cushions arranged in a width direction of the bed. The plurality of firmness adjusters may be arranged in a length of the bed. The user may adjust the cushion strength of the mattress differently for each body part or region of the mattress, thereby providing an advantageous sleep state. A part of the bed may be tilted through an operation of the bedframe, to further improve a sleeping state to the user.

Separating and replacing a topper of the bed may be easy so as to easily or conveniently replace or repair the firmness adjuster after separating the topper. By mounting a drying module on a bottom of the bed, mold on a topper may be reduced or prevented by maintaining the topper in a dry state. Since the topper may be maintained to have a dryness above a certain level (or a moisture or humidity level below a certain level), a pleasant feeling may be perceived by the user when the user's skin touches the topper, thereby facilitating a good night's sleep.

By a fiber-type body pressure sensor, embodiments disclosed herein may quickly identify where a body pressure is concentrated when the user lies on the bed. By a humidity sensor provided in a humidity detection sheet, an area having excessively high humidity among the entire area of the cover sheet or the topper may be detected, and hot wind or air may be intensively supplied from the drying module to the over-humid area. As a result, the bedding, the cover sheet, or the topper may be maintained in a dry state at a comfortable level, improving comfort and a good night's sleep.

Embodiments disclosed herein may be implemented as a bed comprising a mattress and a dryer configured to support and dry the mattress. The dryer may include a support having a top plate supporting the mattress and a side wall extending downward from the top plate and provided on a floor surface, the side wall spacing the top plate apart from the floor surface and having at least one side opening to allow a flow of air into the support, a fan provided inside of the support, the fan having an inlet to suction air and at least one outlet to discharge air, at least one supply duct coupled to the outlet of the fan, and a discharge duct coupled to an outlet of the supply duct through which air may be discharged upward, the discharge duct being exposed through a plurality of top openings formed in the top plate of the support so that discharged air flows toward the mattress.

A suction duct may be coupled to the inlet of the fan and have at least one suction port exposed through the side opening of the support to suction air through the suction port. An inlet of the fan may be provided at a bottom of the fan. A top of the suction port may be formed with a mounting hole in which the bottom of the fan may be mounted. The side wall of the support may include two short sides facing each other and two long sides facing each other and extending between the two short sides. The at least one side opening may include two side openings formed in the long sides to face each other. The at least one suction duct may include two suction ducts provided at the two side openings, respectively, such that the suction duct extends in a direction parallel to the short sides. A filter may be provided at the suction port or the side opening to filter foreign matter from air suctioned into the suction duct.

The fan may be provided under a center of the top plate of the support. The at least one outlet may include a plurality of outlets provided at a side of the fan and spaced apart in a circumferential direction of the fan. The at least one supply duct may include a plurality of supply ducts coupled to the plurality of outlets and extending toward corners of the support in an X shape. An arrangement of the supply ducts and the fan may be symmetrical across a first central axis parallel to a longitudinal direction of the support, and may be symmetrical across a second central axis perpendicular to the first central axis. The supply duct may have a first section extending along a diagonal direction of the bed and a second section extending in a longitudinal direction of the support.

The mattress may include a top layer made of elastic foam. The mattress may include a plurality of springs and a plurality of motors configured to adjust a firmness of the mattress by adjusting heights of some of the springs.

A plurality of frames and at least one drive may be provided. The frames being hinged to each other and adjacent in a longitudinal direction of the support. The drive may move at least one frame to cause the frame to rotate such that a posture of the mattress may be changed.

The mattress may include an elastic foam cushion extending in a width direction of the mattress above where the frames may be hinged to each other. The mattress may include a guard surrounding a vertical side of the mattress.

A cover may be provided around the mattress. A bottom surface of the cover may be formed with a plurality of bottom holes that align with the plurality of top openings of the support to allow a flow of air into the mattress. A damper may be provided in the supply duct to control a flow of air discharged out of the discharge duct.

Embodiments disclosed herein may be implemented as a bed comprising a mattress and a dryer configured to support and dry the mattress. The dryer may include a support having a top plate supporting the mattress and a plurality of legs extending downward from the top plate, the plurality of legs spacing the top plate apart from a floor surface, a fan provided at a bottom surface of the top plate, the fan having an inlet to suction air and at least one outlet to discharge air, at least one supply duct coupled to the outlet of the fan, and a discharge duct coupled to an outlet of the supply duct through which air may be discharged upward, the discharge duct being exposed through a plurality of top openings formed in the top plate of the support so that discharged air flows toward the mattress.

The discharge duct may include a discharge slot through which air may be discharged. The discharge slot may be exposed through the plurality of top openings formed in the top plate of the support. A filter may be provided at the inlet of the fan.

Embodiments disclosed herein may be implemented as a bed comprising a main frame having a first frame rotatably coupled to a second frame such that a posture of the main frame may be adjustable, a plurality of cushions provided above the main frame, each cushion having at least one elastic member, at least one drive configured to adjust a firmness of at least some of the plurality of cushions, a support configured to support the and provided on a floor surface, the support having an inner space provided under the main frame, at least one fan provided in the inner space of the support to suction air, at least one supply duct coupled to an outlet of the fan and having at least one section extending in a longitudinal direction of the main frame, and at least one discharge duct coupled to the supply duct through which air may be discharged upward through holes formed in the support. A vertical side of the support, the floor surface, and a top of the support may define the inner space. At least one opening may be formed in the vertical side of the support to allow air into the inlet of the fan.

Embodiments disclosed herein may be implemented as a bed comprising a mattress and a dryer configured to support and dry the mattress. The dryer may include a support having a top plate supporting the mattress and a side wall extending downward from the top plate and provided on a floor surface. The side wall may space the top plate apart from the floor surface and have at least one side opening to allow a flow of air into the support. At least one fan may be provided inside of the support, the fan having an inlet to suction air and at least one outlet to discharge air. At least one supply duct may be coupled to the outlet of the fan. At least one air dispenser may penetrate the top plate of the support to couple to an outlet of the supply duct. The air dispenser may be provided at a position outside of the mattress to discharge air toward the mattress.

A heater may be provided in the supply duct to heat air discharged toward the mattress. The at least one fan may include a first fan and second fan, the first fan coupled to a first supply duct, and the second fan coupled to a second supply duct, the second supply duct branching off into two extensions. The side wall of the support may include two short sides facing each other and two long sides facing each other and extending between the two short sides, the first supply duct may extend in a longitudinal direction toward a short side provided at a foot of the bed, and the two extensions may extend in a direction perpendicular to the first supply duct toward the two long sides.

At least one suction duct may be provided. The at least one fan may include a first fan and a second fan, and a top of the suction duct may be formed with two mounting holes in which bottoms of the first and second fans may be mounted. The side wall of the support may include two short sides facing each other and two long sides facing each other and extending between the two short sides. The at least one side opening may include two side openings formed in the long sides to face each other. The at least one suction duct may include two suction ducts provided at the two side openings, respectively, such that the suction duct extends in a direction parallel to the short sides.

The air dispenser may include a case penetrating the top plate, the case having a bottom opening and a top opening, a pop-up duct provided inside of the case between the top opening and the bottom opening, the pop-up duct having a bottom opening aligning with the bottom opening of the case and a discharge slot formed in a side surface through which air may be discharged, and a lift comprising a motor and configured to raise and lower the pop-up duct with respect to the case. The lift further may include a motor housing in which the motor may be provided and a shaft coupling the motor to a pinion such that the motor rotates the pinion. A rear of the pop-up duct may be formed with a rack configured to engage with the pinion.

The case may include a partition dividing the case into a first space and a second space, the partition having a guide slit. The motor housing may be provided in the first space. The shaft may penetrate the guide slit. The pinion and the pop-up duct may be provided in the second space. A rear of the pop-up duct may include a groove in which the pinion fits.

At least one spring may be provided in the first space and coupled to the motor housing such that, when a downward force may be applied on the pop-up duct, the spring may be compressed, and when the downward force may be removed, a restoring force of the spring moves the pop-up duct back to an initial position. The at least one spring may include two coil springs. A discharge grill may be provided in the discharge slot.

Embodiments disclosed herein may be implemented as a bed comprising a mattress, a main frame provided below the mattress, a guard surrounding the main frame, the guard having a plurality of legs to space the main frame apart from a floor surface, and a dryer configured to dry the mattress. The dryer may include at least one fan provided at a bottom surface of the main frame, the fan having an inlet to suction air and at least one outlet to discharge air, at least one supply duct coupled to the outlet of the fan, and at least one air dispenser coupled to an outer side of the guard and communicating with an outlet of the supply duct, the air dispenser having a discharge port formed in a side surface to discharge air toward the mattress.

The air dispenser may include a motor, a pop-up duct formed with a rack, and a pinion rotated by the motor and engaging with the rack to move the rack in a vertical direction. An elastic member may support the motor such that when a downward force may be applied to the pop-up duct, the motor may descend, and the elastic member may be compressed. The at least one fan may include two axial fans provided at a foot of the main frame. At least one heater may be provided in the supply duct to heat air discharged through the air dispenser.

Embodiments disclosed herein may be implemented as a bed comprising a main frame having a first frame rotatably coupled to a second frame such that a posture of the main frame may be adjustable, a plurality of cushions provided above the main frame and having at least one elastic member, at least one drive configured to adjust a firmness of at least some of the plurality of cushions, a support provided on a floor surface and configured to support the main frame, the support having an inner space provided under the main frame, at least one fan provided in the inner space of the support to suction air, at least one supply duct coupled to an outlet of the fan and having at least one section extending in a longitudinal direction of the main frame, at least one pop-up duct configured to discharge air received from the supply duct, and a motor configured to raise the pop-up duct during a drying operation and lower the pop-up duct after a drying operation.

Embodiments disclosed herein may be implemented as a method of controlling mattress humidity comprising sensing a humidity at a plurality of points on a mattress, determining at least one average humidity value based on the sensed humidity at the plurality of points, and performing a drying operation based on the determined average humidity values. Performing the drying operation may include operating at least one fan provided below the mattress to suction air and discharge air toward the mattress to dry the mattress. Performing the drying operation may further include operating at least one heater to heat air discharged to the mattress.

The mattress may include a plurality of regions. Determining the at least one average humidity value may include determining an average humidity value for each region of the mattress. Performing the drying operation further may include operating at least one damper to control a region to be dried during the drying operation. Performing the drying operation further may include operating a motor to raise at least one air dispenser.

A humidifying sensing sheet may be provided on the mattress to sense the humidity at the plurality of points. The humidifying sensing sheet may have a plurality of electrode lines configured to measure humidity or moisture.

The method may further comprise processing the average humidity values, generating an image based on the processed average pressure values, and outputting the image on a display. A user interface configured to receive at least one of an automatic command or a manual command is provided on a remote controller having a display.

Upon receiving an automatic command based on a user input into a user interface, the step of performing the drying operation may include comparing the determined average humidity value to a predetermined humidity range. The step of performing the drying operation may include operating the fan for a predetermined time period if the determined average humidity value exceeds the predetermined humidity range. After the predetermined time period, sensing the humidity, determining the average humidity value, and performing the drying operation may be repeated until the determined average humidity value is inside the predetermined humidity range.

The method may further comprise determining a season of the year. Upon receiving an automatic command based on a user input into a user interface, the step of performing the drying operation may include comparing the determined average humidity value to a predetermined humidity range for the determined season. The step of performing the drying operation may include operating the fan for a predetermined time period if the determined average humidity value exceeds the predetermined humidity range for the determined season.

The method may further comprise sensing a temperature of the mattress and determining a predetermined temperature range in which the sensed temperature is provided. Upon receiving an automatic command based on a user input into a user interface, the step of performing the drying operation may include comparing the determined average humidity value to a predetermined humidity range for the predetermined temperature range. The step of performing the drying operation may include operating the fan for a predetermined time period if the determined average humidity value exceeds the predetermined humidity range for the predetermined temperature range.

Upon receiving a manual command based on a user input into a user interface, the step of performing the drying operation may include selecting a desired humidity value via the user interface, comparing the determined average humidity value with the desired humidity value, and operating the fan for a predetermined time period if the determined average humidity value exceeds the desired humidity value.

The method may further comprise sensing a temperature and operating a heater for a predetermined time if the sensed temperature is less than a predetermined temperature.

Embodiments disclosed herein may be implemented as a method of controlling a mattress humidity comprising receiving a command to adjust a firmness of the mattress, performing a humidity scan of the mattress, storing data from the humidity scan, processing the stored data, determining, using the stored data, humidity values corresponding a plurality of regions of the mattress, generating, via the processed data, a humidity image reflecting the humidity values at the plurality of regions, outputting the humidity image on a display, comparing the determined humidity values to predetermined humidity values, and performing a drying operation to dry the mattress based on the comparison between the determined humidity values and the predetermined humidity values.

The predetermined humidity values may be selected based on a user selection via a user interface provided on a remote controller, the remote controller having the display.

The predetermined humidity values may be determined based on at least one of past user selections provided via a user interface, a season of year, an ambient temperature, or a comparison of all of the determined humidity values to each other.

Performing the humidity scan may include repeatedly sensing the humidity, determining a difference between a current sensed humidity and a previous sensed humidity, comparing the determined difference to a predetermined error range, when the determined difference is within the predetermined error range for a first predetermined time period, proceeding to the step of determining the average humidity value, and when the determined difference is not within the predetermined error range for a second predetermined time period, stopping sensing for a third predetermined time period, and repeating the step of repeatedly sensing the humidity after the third predetermined time period.

Performing the drying operation may include operating at least one of a fan or a heater. Performing the drying operation may include operating at least one fan to suction and discharge air and at least one damper to control a region of the mattress where air is supplied. Performing the humidity scan may include sensing a plurality of pressures using a pressure sensor sheet provided on the mattress.

Embodiments disclosed herein may be implemented as a bed comprising a mattress and a dryer configured to support and dry the mattress. The dryer may include an edge frame having a side wall, a top plate seated on top of the edge frame and supporting the mattress, a bottom plate provided under the edge frame to space the edge frame apart from a floor surface, at least one fan provided inside of the edge frame, the fan having an inlet to suction air and at least one outlet to discharge air, at least one supply duct coupled to the outlet of the fan, and at least one air dispenser coupled to an outlet of the supply duct, the air dispenser being provided at a position outside of the mattress to discharge air toward the mattress.

An inlet hole may be formed in a bottom of the edge frame at a position outside of the bottom plate such that the bottom plate does not interfere with a flow of air through the inlet. A filter slot may be formed in the side wall. A filter may be configured to be inserted into the filter slot and above the inlet. The filter slot may be inclined such that the filter may be configured to be inserted at an angle covering the inlet.

The filter may include a frame, a plurality of ribs extending across the frame, and a mesh material provided in the frame and supported by the ribs. An outer edge of the filter may include a handle to pull the filter out of the filter slot.

A discharge hole formed in the side wall. An outer side of the side wall may include a recess in which a grill may be provided, the grill covering the discharge hole. The discharge hole may be inclined upward toward an upper corner of the edge frame. The air dispenser may be provided in the discharge hole such that a first section may be seated in the discharge hole and a second section may extend to an outside of the edge frame.

A heater may heat air to be discharged through the air dispenser. An inner side of the air dispenser may include a recess in which the heater may be provided. The heater may be provided inside of a heater housing. The supply duct may be coupled to an inlet of the heater housing. An outlet of the heater housing may be coupled to an inlet of the air dispenser.

The air dispenser may include an inner wall and an outer wall defining a discharge passage leading to an upper opening. Inner surfaces of the inner and outer wall are configured such that a cross-sectional area of the discharge passage increases in a direction toward the upper opening. An inner surface of the outer wall may include an air guide having an inclined surface provided at the upper opening, a thickness of the inclined surface in a direction between the inner and outer walls decreasing in a downward direction.

Embodiments disclosed herein may be implemented as a bed comprising a mattress and a dryer configured to support and dry the mattress. The dryer may include at least one fan provided under the mattress, the fan having an inlet to suction air and at least one outlet to discharge air, at least one supply duct coupled to the outlet of the fan, and at least one air dispenser coupled to an outlet of the supply duct, the air dispenser having an outlet provided at a position outside of the mattress to discharge air upward at a side of the mattress.

A side of the mattress adjacent to the outlet of the air dispenser may have a convex curvature such that a flow of air upward clings to a side of the mattress. The air dispenser may have a thickness in a direction away from the mattress such that, when a blanket may be provided on the mattress, an end of the blanket may cover the outlet of the air dispenser such that air discharged from the air dispenser may be guided to a space between the blanket and the mattress. A heater may be adjacent to an inlet of the air dispenser.

It will be understood that when an element or layer is referred to as being "on" another element or layer, the element or layer can be directly on another element or layer or intervening elements or layers. In contrast, when an element is referred to as being "directly on" another element or layer, there are no intervening elements or layers present. As used herein, the term "and/or" includes any and all combinations of one or more of the associated listed items.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section could be termed a second element, component, region, layer or section without departing from the teachings of the present invention.

Spatially relative terms, such as "lower", "upper" and the like, may be used herein for ease of description to describe the relationship of one element or feature to another element(s) or feature(s) as illustrated in the figures. It will be understood that the spatially relative terms are intended to encompass different orientations of the device in use or operation, in addition to the orientation depicted in the figures. For example, if the device in the figures is turned over, elements described as "lower" relative to other elements or features would then be oriented "upper" relative to the other elements or features. Thus, the exemplary term "lower" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the disclosure are described herein with reference to cross-section illustrations that are schematic illustrations of idealized embodiments (and intermediate structures) of the disclosure. As such, variations from the shapes of the illustrations as a result, for example, of manufacturing techniques and/or tolerances, are to be expected. Thus, embodiments of the disclosure should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Any reference in this specification to "one embodiment," "an embodiment," "example embodiment," etc., means that a particular feature, structure, or characteristic described in connection with the embodiment is included in at least one embodiment of the invention. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A bed, comprising:
   a mattress; and
   a dryer configured to support and dry the mattress, the dryer including:

a support having a top plate supporting the mattress and a side wall extending downward from the top plate and provided on a floor surface, the side wall spacing the top plate apart from the floor surface and having at least one side opening to allow a flow of air into the support;

a fan provided inside of the support, the fan having an inlet to suction air to the fan and at least one outlet to discharge air from the fan;

at least one supply duct coupled to the outlet of the fan to receive the air from the fan; and a discharge duct coupled to an outlet of the supply duct through which air is discharged upward from the supply duct to a base of the discharge duct, the discharge duct being exposed through a plurality of top openings formed in the top plate of the support so that discharged air flows upward from the supply duct by passing through the discharge duct in a direction toward the mattress and then through at least one of the top openings in the top plate, wherein the at least one supply duct is coupled to the outlet of the fan and is coupled to the base of the discharge duct.

2. The bed of claim 1, further comprising a suction duct coupled to the inlet of the fan and having at least one suction port exposed through the side opening of the support to suction air through the suction port.

3. The bed of claim 2, wherein the inlet of the fan is provided at a bottom of the fan, and a top of the suction port is formed with a mounting hole in which the bottom of the fan is mounted.

4. The bed of claim 2, wherein the side wall of the support includes two short sides facing each other and two long sides facing each other and extending between the two short sides, the at least one side opening includes two side openings formed in the long sides to face each other, and the suction duct includes two suction ducts provided at the two side openings, respectively, such that the suction duct extends in a direction parallel to the short sides.

5. The bed of claim 2, further comprising a filter provided at the suction port or the side opening to filter foreign matter from air suctioned into the suction duct.

6. The bed of claim 1, wherein the fan is provided under a center of the top plate of the support, the at least one outlet of the fan includes a plurality of outlets provided at a side of the fan and spaced apart in a circumferential direction of the fan, and the at least one supply duct includes a plurality of supply ducts coupled to the plurality of outlets and extending toward corners of the support in an X shape.

7. The bed of claim 6, wherein an arrangement of the supply ducts and the fan is symmetrical across a first central axis parallel to a longitudinal direction of the support, and is symmetrical across a second central axis perpendicular to the first central axis.

8. The bed of claim 1, wherein the supply duct has a first section extending along a diagonal direction of the bed and a second section extending in a longitudinal direction of the support.

9. The bed of claim 1, wherein the mattress includes a top layer made of elastic foam.

10. The bed of claim 1, wherein the mattress includes a plurality of springs and a plurality of motors configured to adjust a firmness of the mattress by adjusting heights of some of the springs.

11. The bed of claim 1, further comprising a plurality of frames and at least one drive, the frames being hinged to each other and adjacent in a longitudinal direction of the support, and the drive configured to move at least one frame to cause the frame to rotate such that a posture of the mattress is changed.

12. The bed of claim 11, wherein the mattress includes an elastic foam cushion extending in a width direction of the mattress above where the frames are hinged to each other.

13. The bed of claim 1, wherein the mattress includes a guard surrounding a vertical side of the mattress.

14. The bed of claim 1, wherein a cover is provided around the mattress, and a bottom surface of the cover is formed with a plurality of bottom holes that align with the plurality of top openings of the support to allow a flow of air into the mattress.

15. The bed of claim 1, further comprising a damper provided in the supply duct to control a flow of air discharged out of the discharge duct.

16. A bed, comprising:
a mattress; and
a dryer configured to support and dry the mattress, the dryer including:
a support having a top plate supporting the mattress and a plurality of legs extending downward from the top plate, the plurality of legs spacing the top plate apart from a floor surface;
a fan provided at a bottom surface of the top plate, the fan having an inlet to suction air to the fan and at least one outlet to discharge air from the fan;
at least one supply duct coupled to the outlet of the fan to receive the air from the fan; and
a discharge duct coupled to an outlet of the supply duct through which air is discharged upward from the supply duct to a base of the discharge duct, the discharge duct being exposed through a plurality of top openings formed in the top plate of the support so that discharged air flows upward from the supply duct by passing through the discharge duct in a direction toward the mattress and then through at least one of the top openings in the top plate,
wherein the at least one supply duct is coupled to the outlet of the fan and is coupled to the base of the discharge duct.

17. The bed of claim 16, wherein the discharge duct includes a discharge slot through which air is discharged, the discharge slot being exposed through the plurality of top openings formed in the top plate of the support.

18. The bed of claim 16, further comprising a filter provided at the inlet of the fan.

19. A bed, comprising:
a main frame having a first frame rotatably coupled to a second frame such that a posture of the main frame is adjustable;
a plurality of cushions provided above the main frame, each cushion having at least one elastic member;
at least one drive configured to adjust a firmness of at least some of the plurality of cushions;
a support configured to support the main frame and provided on a floor surface, the support having an inner space provided under the main frame;
at least one fan provided in the inner space of the support to suction air;
at least one supply duct coupled to an outlet of the fan to receive the air from the fan, and having at least one section extending in a longitudinal direction of the main frame; and
at least one discharge duct coupled to the supply duct through which air is discharged upward from the supply duct to a base of the discharge duct and then through holes formed in the support,
wherein the at least one supply duct is coupled to the outlet of the fan and to the base of the discharge duct.

20. The bed of claim 1, wherein a vertical side of the support, the floor surface, and a top of the support define the inner space, and at least one opening is formed in the vertical side of the support to allow air into the inlet of the fan.

\* \* \* \* \*